United States Patent
Martin et al.

(10) Patent No.: US 10,557,145 B2
(45) Date of Patent: Feb. 11, 2020

(54) FLAGELLIN-SENSING 3 ('FLS3') PROTEIN AND METHODS OF USE

(71) Applicant: BOYCE THOMPSON INSTITUTE FOR PLANT RESEARCH, Ithaca, NY (US)

(72) Inventors: Gregory B. Martin, Ithaca, NY (US); Sarah R. Hind, Ithaca, NY (US); Susan R. Strickler, Ithaca, NY (US)

(73) Assignee: BOYCE THOMPSON INSTITUTE FOR PLANT RESEARCH, INC., Ithaca, NY (US)

( * ) Notice: Subject to any disclaimer, the term of this patent is extended or adjusted under 35 U.S.C. 154(b) by 12 days.

(21) Appl. No.: 15/324,389

(22) PCT Filed: Jul. 8, 2015

(86) PCT No.: PCT/US2015/039520
§ 371 (c)(1),
(2) Date: Jan. 6, 2017

(87) PCT Pub. No.: WO2016/007606
PCT Pub. Date: Jan. 14, 2016

(65) Prior Publication Data
US 2018/0023092 A1    Jan. 25, 2018

Related U.S. Application Data

(60) Provisional application No. 62/021,995, filed on Jul. 8, 2014.

(51) Int. Cl.
*C12N 15/82* (2006.01)
*C07K 14/415* (2006.01)
*C12Q 1/6895* (2018.01)

(52) U.S. Cl.
CPC ........ *C12N 15/8279* (2013.01); *C07K 14/415* (2013.01); *C12N 15/8218* (2013.01); *C12Q 1/6895* (2013.01); *C12Q 2600/13* (2013.01); *C12Q 2600/158* (2013.01)

(58) Field of Classification Search
CPC .................................................. C12N 15/8279
USPC ......................................................... 800/279
See application file for complete search history.

(56) References Cited

U.S. PATENT DOCUMENTS

2008/0307539 A1    12/2008  Zipfel et al.
2012/0005785 A1     1/2012  Frankard et al.
2012/0137392 A1*    5/2012  De Lorenzo ......... C12N 9/1205
                                                             800/301

OTHER PUBLICATIONS

Ma et al. 2012 GenBank Access No. XM_004237116.1.*
Uniprot Accession ID K4BPB9_SOLLC, 2 pages (Nov. 28, 2012).
Clarke et al., "Allelic Variation in Two Distinct Pseudomonas Syringae Flagellin Epitopes Modulates the Strength of Plant Immune Responses But Not Bacterial Motility," New Phytologist 200:847-860 (2013).
NCBI Reference Sequence: XM_004237116, Predicted: Solanum Lycopersicum Probable LRR Receptor-like Serine/Threonine-protein Kinase At3g47570-like (LOC101248095), mRNA, 2 pages (Mar. 12, 2013).
PCT International Search Report for corresponding PCT/US2015/039520, 7 pages (dated Jan. 6, 2016).
PCT Written Opinion for corresponding PCT/US2015/039520, 13 pages (dated Jan. 6, 2016).
Hind et al., "The Tomato Receptor FLAGELLIN-SENSING 3 Perceives flgII-28 and Activates Immune Signaling," Oral Presentation at Keystone Symposia Conference, Plant Receptor Kinases: From Molecules to Environment, Taos, New Mexico (Feb. 2015).
Hind et al., "The Tomato Receptor FLAGELLIN-SENSING 3 Perceives flgII-28 and Activates Immune Signaling," Poster Presentation at Keystone Symposia Conference, Plant Receptor Kinases: From Molecules to Environment, Taos, New Mexico (Feb. 2015).
Hind et al., "The Tomato Receptor FLAGELLIN-SENSING 3 Perceives flgII-28 and Activates Immune Signaling," Oral Presentation at the Department of Plant Pathology and Plant-Microbe Biology, Cornell University, Ithaca, NY (Mar. 2015).
Hind et al., "Identification of the flgII-28 Receptor FLS3 Using Natural Variation in Tomato" XVI International Conference of Molecular Plant-Microbe Interactions, Rhodes, Greece (Jul. 9, 2014).
PCT International Report on Patentability for corresponding PCT/US2015/039520, 14 pages (dated Jan. 10, 2017).
Hind et al., "Tomato Receptor FLAGELLIN-SENSING 3 Binds FlgII-28 and Activates the Plant Immune System," Nature Plants 2:16128 (2016).

* cited by examiner

*Primary Examiner* — Li Zheng
(74) *Attorney, Agent, or Firm* — Pepper Hamilton LLP

(57) ABSTRACT

One aspect of the present invention relates to a nucleic acid construct that includes a nucleic acid molecule that encodes FLAGELLIN-SENSING 3 ("FLS3") protein; a 5' heterologous DNA promoter sequence; and a 3' terminator sequence, where the nucleic acid molecule, the DNA promoter sequence, and the terminator sequence are operatively coupled to permit transcription of the nucleic acid molecule. The present invention also relates to a method of imparting disease resistance to a plant. This method involves transforming a plant or a plant seed with a nucleic acid molecule that increases expression of an FLS3 protein, where said transforming is effective in imparting disease resistance to the transformed plant or to a transgenic plant produced from the transformed plant seed. The present invention also relates to methods of expressing a nucleic acid molecule in a plant, identifying a candidate plant suitable for breeding that displays enhanced disease resistance, and enhancing efficiency of transformation of a plant by *Agrobacterium*.

28 Claims, 21 Drawing Sheets

Specification includes a Sequence Listing.

```
Solyc02g070890.2.1/1-1170    1 - - -MMMLKTVVYALAIFSITF-LI-PLSS- -GQNPRFEVEVAALKAFKSSISDDP  48
Solyc04g009640.2.1/1-1136    1 MEKHIFL- -LI- -LAIL-VQFYFVSSISATISSN- - -ETDQEALLAFRNLVTSDS  47

Solyc02g070890.2.1/1-1170   49 - -FSALV-DWTDVNHHCNWSGII CDPSSNHVINISLIETQLKGEISPFLGNLSKL 100
Solyc04g009640.2.1/1-1136   48 SHF- -LANNWTKNTSFCSWFGVTCSPKRQRVVALTLPNLQGTISPSLANL- - -  97

Solyc02g070890.2.1/1-1170  101 QVLDLTLNSFTGNIPPQLGHCTDLVELVFYQNSLFGEIPAELGNLKKLQLIDFGN 155
Solyc04g009640.2.1/1-1136   98 - - - - - -SF- - - - - - - -LIELNLANNLHSEIPDGIGRLPRLRVIDIQN 131

Solyc02g070890.2.1/1-1170  156 NFLNGSIPDSI- -CNCTELLLVGFNN- - -NNFTGK- -LPSEIGNLANLQLFVAYT 203
Solyc04g009640.2.1/1-1136  132 NQLHGSIPTSLFQHGSVQIISLAFNKLGGEMWNGTWYVP-EL-RVLNLR- - - -  -N 179

Solyc02g070890.2.1/1-1170  204 NNLVGFMPTSIGMLTALHTDLSENQLSGPIPPEIGNLSSLGILQLHL- -NSLSG 256
Solyc04g009640.2.1/1-1136  180 NTITGVIPPSIGNATKLMNFSLNGNRINGNIPMEIGNLSQL- -VELSLSRNQLTG 232

Solyc02g070890.2.1/1-1170  257 KIPSELGLCI-NLFTLNM-YTNQFTGSI-PPELGNL- -ENLQMLRL-YNNKLNSS 305
Solyc04g009640.2.1/1-1136  233 SIPSTL-FNISSLLVVSLAY-NSLSGPLFPDDRRNVLSSNLEHIGVSY-NQITGH 284

Solyc02g070890.2.1/1-1170  306 IPASIFHLKSLTHLGLSQNELTGNIPPQLGSLTSLEVLTLHSNKLSGEIPSTITN 360
Solyc04g009640.2.1/1-1136  285 IPSNICQFTALRVLSISYNNITGEIPRNIGCLAKLEEFYIGYNAINGTIPASLGN 339

Solyc02g070890.2.1/1-1170  361 LANLTYLSLGFNLLTGSLPSEFGLLYNLK- -NLTANNLLEGSIPLSIINCSHLL 413
Solyc04g009640.2.1/1-1136  340 ISTLQNLHCGSNHMEGELPPELGKLSNLRQINFEENVNLI-GEIPNTIFNISSLE 393
```

*FIG. 2D*

```
Solyc02g070890.2.1/1-1170   414  VLSLTFNRITGEIPNGLGQLSNLTFLSLGSNKMMGEIPDDLFNSSMLEVLDLSDN  468
Solyc04g009640.2.1/1-1136   394  FIAFFNYLSGRIPN-LLHLPNLIQLLANNQLEGEIPRYITNATNLELELSDN    447

Solyc02g070890.2.1/1-1170   469  NFSGKLKPM-IGRLAKLRVLRAHSNSF--LG----------------P---  497
Solyc04g009640.2.1/1-1136   448  LLTGTI-PNDLGNLRELRDLFHHNQLTELGFFDSLVKCRMLRYVQVGSNPLNDV  501

Solyc02g070890.2.1/1-1170   498  IPPEIGKLSQLLDLALH--KNSFSGAIPPEISMLSNLQGLLLSDNKLEGELPVQL  550
Solyc04g009640.2.1/1-1136   502  LPSSIGNLSSTVEY-FHIGDAQINGFIPTSTGNMTGLTTLVFQDNSLTGNIPREI  555

Solyc02g070890.2.1/1-1170   551  FELKQLNELRLKNNNFFGPIPHISKLESLSLMDLSGNKLNGTIPE---SMTSLR  602
Solyc04g009640.2.1/1-1136   556  RKLKQLQGLFLVNNGLQGDIAEVVCDLSNLVRLALSENELSGVIPECLGNLTMLQ  610

Solyc02g070890.2.1/1-1170   603  RLMTVDLSHNLLTGTLPRAVLA--SMRSMQLYLNVSSNLLHGEIPDEIGVLEMVQ  655
Solyc04g009640.2.1/1-1136   611  QLF---LGSNKFESKLP--LSFWKMSSL-LYLNMSRNSIKGEVPSDIGELKAIV  658

Solyc02g070890.2.1/1-1170   656  EIDMSNNNLSGSIPRSLERCKNLFSLDLSGNMLSGPAPGEILTKLSELVFLNLSR  710
Solyc04g009640.2.1/1-1136   659  AIDISGNHFSGSIP------SNL-----------GELQT----LKLLSLSN    688

Solyc02g070890.2.1/1-1170   711  NRLEGSLP-EIAGLSHLSSLDVSQNKFKGIIPERFANMTALKYLNLSFNQLEGHI  764
Solyc04g009640.2.1/1-1136   689  NSFSGPIPFSFSNLKSLEFLDLSLNNLSGTIPKSFEKLLYLTSINVSFNVLEGEI  743

Solyc02g070890.2.1/1-1170   765  PKGGVFNNIRLEDLLGNPSLCGKFLS-P-CHIKR-NRTSSHGFSKKTWIILAAL  816
Solyc04g009640.2.1/1-1136   744  PSGGVFANSTLQSFSGNKGLGGRQILEVPACAITTPEQQSK--SKK--LVLKIV  794
```

FIG. 2D (cont.)

```
Solyc02g070890.2.1/1-1170    817 GSV---FSLI-LLVGIFLFHRYMKKK-KVNDTEFTNPKCTAALSLQRFYQKDLE 866
Solyc04g009640.2.1/1-1136    795 TPMVISFFLIFLLVVSIWIMKR--KKKGKSKDVE-KVPEMR-TYQLISYH--EIQ 843

Solyc02g070890.2.1/1-1170    867 HATNNFRPENIIGASSLSTVYKGTLEDGKIVAVKKLNHQFSAESGKCFDREVKTL 921
Solyc04g009640.2.1/1-1136    844 RATNNFDESNLIGVGGSGVYKATLASGIVVAIKVLDLE-NEEVCKRFDTECEVM 897

Solyc02g070890.2.1/1-1170    922 SQLRHRNLVKVLGYAWESKKLRALVLEYMENGNLDNMIYGQVED-DWTLSNRIDI 975
Solyc04g009640.2.1/1-1136    898 RNVRHKNLVSVITTC-SSEHIRAFVLQYMPNGSLDNWLYK--EDRHLKLRQRVTI 949

Solyc02g070890.2.1/1-1170    976 LVSVASGLSYLHSGYDFPIVHCDMKPSNILLDKNMEAHVSDFGTARMLGIHLQDG 1030
Solyc04g009640.2.1/1-1136    950 MLDVAMAIEYLHGNDTPIVHCDLKPANVLLDEDMVARVGDFGISKILAV---S 1000

Solyc02g070890.2.1/1-1170   1031 SSTSSASAFEGTIGYMAPELAYMRK--VTTKVDVFSFGVIVMEIITKRRPTSLTG 1083
Solyc04g009640.2.1/1-1136   1001 KSMAHTKTL-GTLGYIAPE-YGSEGIVSTRGDVYSYGIMLMEVLAKRRP---TG 1049

Solyc02g070890.2.1/1-1170   1084 ADEL--PITLHQIVQNALANGINKLVQIVDPNL---ASYVSKKQDV-VEGLLNL 1131
Solyc04g009640.2.1/1-1136   1050 -EEIFNENLGLREWITRAFP---RTMMEVVDADMFHDGEKITSESEICILSMIEL 1100

Solyc02g070890.2.1/1-1170   1132 ALSCTSPDPEDRPDMEQVLSSLSKLSKMDCMPSHL-VKD*                1170
Solyc04g009640.2.1/1-1136   1101 ALDCTKATPESRITMKDVVKRLNKI-K-NTF-GNIEVN-*                1136
```

FIG. 2D (cont.)

CLUSTAL W(1.83) MULTIPLE SEQUENCE ALIGNMENT

```
Heinz1706_   MEKHIFLLILAILVQFYFVSSISATISSNETDQEALLAFRNLVTSDSSHFLANNWTKN-T   59
LA1589_      MEKHIFLLILAILVQFYFVSSISATISSNETDQEALLAFRNLVTSDSSHFLANNWTKN-T   59
Pepper_      MEKHIFLLILFLVQVYAVASILV-TSSNETDQEALLAFRNLIRSDSSHFLANNWTKNST   59
Potato_      MEKHIFLILAILVQFYFVSSISATIFSNETDQEALLAFRNLVTSDSSQFLANNWTKN-T   59
             ********:*:**:*.:**  *:********** :*:**.***:********  *

Heinz1706_   SFCSWFGVTCSPKRQRVVALTLPNLQLQGTISPSLANLSFLIELNLANNNLHSEIPDGIG  119
LA1589_      SFCSWFGVTCSPKRQRVVALTLPNLQLQGTISPSLANLSFLIELNLANNNLHSEIPDGIG  119
Pepper_      SFCSWFGVTCSPRRQRVVALNLPDLQLPGTISPSLANLSFLRELNLGNNSFHGNIPYGIG  119
Potato_      SFCSWFGVTCSPKRQRVVALTLPNLQLQGTISPSLANLSFLIELNLTNNNFHGNIPYGIG  119
             ************:*******.**:***.*************. ****.:*.:.* *:***

Heinz1706_   RLPRLRVIDIQNNQLHGSIPTSLFQHGSVQIISLAFNKLGGEMWNGTWYVPELRVLNLRN  179
LA1589_      RLPRLRVIDIQNNQLHGSIPTSLFQHGSVQIISLAFNKLGGEMWNGTWYVPELRVLNLRN  179
Pepper_      NLPRLRVIDIQNNQLQGSIPASLFQHRVQIISLAFNKLSGEMWNGTWYVPELRVLNLRN  179
Potato_      HLPRLRVIDIQNNQLQGSIPTSLFQHRSVQIISLAFNKLGGEMWNGTWYVPELRVLNLRN  179
             .**************:***:*****.*********.***************

Heinz1706_   NTITGVIPPSIGNATKLMNFSLNGNRINGNIPMEIGNLSQLVELSLSRNQLTGSIPSTLF  239
LA1589_      NTITGVIPPSIGNATKLMNFSLNGNRINGNIPMEIGNLSQLVELSLSRNQLTGSIPSTLF  239
Pepper_      NLTGRIPPSIGNATKLMNFSLHGNRISGNIPKEIGNLSQLAELFLSRNQLTGSIPTTLF  239
Potato_      NTITGRIPPSIGNATKLMNISLNWNRINGNIPMEIGNLSQLVELSLSRNQLTGSIPSTLF  239
             * *. ***************::**.***.***:*******.** ***********:***
```

FIG. 2F

```
Heinz1706_   NISSLLVVSLAYNSLSGPLFPDDRRNVLSSNLEHIGVSYNQITGHIPSNICQFTALRVLS  299
LA1589_      NISSLLVVSLAYNSLSGPLFPDDRRNVLSSNLEHIGVSYNQITGHIPSNICQFTALRVLS  299
Pepper_      NISSLLVASLAFNSLSGPLLGEG--NILSNLEHLGMSYNQISGRIPSNICQLKELKVLS   297
Potato_      NISSLLVVSLAYNSLSGPLFLDDRRNVLSSNLEHIGVSYNQITGHISSNICQFKALKVLS  299
             ******* **:***:****:  : *:****:**.****:** *:.****:*:.*:***

Heinz1706_   ISYNNITGEIPRNIGCLAKLEEFYIGYNAINGTIPASLGNISTLQNLHCGSNHMEGELPP  359
LA1589_      ISYNNITGEIPRNIGCLAKLEEFYIGYNAINGTIPASLGNISTLQNLHCGSNHMEGELPP  359
Pepper_      ISFNNITGEMPRNVGCLTKLEELYIGYNPINGRIPTSLGNISTLQKLHCGNNSMIGEIPP  357
Potato_      ISYNNITGEIPRNIGCLAKLEELYIGYNAIDGTIPTSLGNISTLQKLHCGNNHMEGELPP  359
             **:******:*** **:****:*****.*:*.**.******:*****.:. *** ***

Heinz1706_   ELGKLSNLRQINFEENYNLIGEIPNTIFNISSLEFIAFTFNYLSGRIPNLLHLPNLIQLL  419
LA1589_      ELGKLSNLRQINFEENYNLIGEIPNTIFNISSLEFIAFTFNYLSGRIPNLLHLPNLIQLL  419
Pepper_      ELGKLSNLREIDFSENYNLTGEIPNSIFNISLEFIVFSFNYLSGRIPVLLHFPNLIQLF   417
Potato_      ELGKLSNLRQINFEENYNLIGEIPNAIFNISSLEFIAFTFNYLSGRIPNLLHLPNLIQLL  419
             ********:*:.***** ******:*****.***.*:*********.***:*****:

Heinz1706_   LANNQLEGEIPRYITNATNLELELELSDNLLTGTIPNDLGNLRELRDLFLHHNQLTELGFF  479
LA1589_      LANNQLEGEIPRYITNATNLELELELSDNLLTGTIPNDLGNLRELRDLFLHHNQLTELGFF  479
Pepper_      LANNQLEGEIPRYITNATKLESIDLSVNRLTGTIPNNLGNLRKLKQLFLHHNQLIELGFF   477
Potato_      LANNQLEGEIPRYITNATNLELELSDNLLTGSIPYDLGNLRELQELFLHHNQLTELGFF   479
             ******************:**.:: **:* ** :**  ****:*::**:***** *****

Heinz1706_   DSLVKCRMLRYVQVGSNPLNDVLPSSIGNLSSTVEYFHIGDAQINGFIPTSTGNMTGLTT  539
LA1589_      DSLVKCRMLRYVQVGSNPLNDVLPSSIGNLSSTVEYFHIGDAQINGFIPTSTGNMTGLTT  539
Pepper_      DSLVNCRMLQYVQVGSNPLNGVLPSSNVEVFHIGDAQISGFIPTSTGNMSGLTT       537
Potato_      DSLVKCRMLRYVQVGSNPLNGVLPSSIGNLSSTVEYFHIGDAQINGFIPTSTGNMSGLTT  539
             ****:****:**********:******.:.:****:**********.*********.***
```

```
Heinz1706_    LVFQDNSLTGNIPREIRKLKQLQGLFLVNNGLQGDIAEVVCDLSNLVRLALSENELSGVI    599
LA1589_       LVFQDNSLTGNIPREIGKLKQLQGLFLVNNGLQGDIAEVVCDLSNLVRLALSENELSGVI    599
Pepper_       LVFQDNNLTGNIPREIGRLKQLQGLFLINNELQGDITAVVCDLSNLVRLSLSDNELSGVI    597
Potato_       LVLQDNNLTGNIPREIGKLKQLQGLFLVNNELQGDIAEVVCDLSNLVRLALSENELSGVI    599
              **:***:*******.:*****:*****:**:****::.*********:*:*:*******

Heinz1706_    PECLGNLTMLQQLFLGSNKFESKLPLSFWKMSSLLYLNMSRNSIKGEVPSDIGELKAIVA    659
LA1589_       PECLGNLTMLQQLFLGSNKFESKLPLSFWKMSSLLYLNMSRNSIKGEVPSDIGELKAIVA    659
Pepper_       PNCIGNLSMLQQLFLGSNNFGSELPLSIWKMRGLLFVNISLNSLEGEVPSDIGELKAIVE    657
Potato_       PECLGSLTMLQHLFLGSNKFESKLPLSFWKMSSLLYVNMSRNSIEGEVPSDIGELKAIVA    659
              *.*:*.*:***:******:*.*:****:***..**:.: ..**:: ************

Heinz1706_    IDISGNHFSGSIPSNLGELQTLKLLSLSNNSFSGPIPFSFSNLKSLEFLDLSINNLSGTI    719
LA1589_       IDISGNHFSGSIPSNLGELQTLKLLSLSNNSFSGPIPFSFSNLKSLEFLDLSINNLSGTI    719
Pepper_       IDISGNHFSGMIPSNLGELQNLQLLSLSNNSFSGPIPLSFSNLISLEILDLSINNLSGTI    717
Potato_       IEISGNHFSGMIPSNLGELQNLKLLSLSNNSFSGPIPLSFSNLKSLEFLDLSINNLSGTI    719
              *:********.*********:*:**************:****:***:*************

Heinz1706_    PKSFEKLLYLTSINVSFNVLEGEIPSGGVFANSTLQSFSGNKGLCGRQILEVPACAITTP    779
LA1589_       PKSFEKLLYLTSINVSFNVLEGEIPSGGVFANSTLQSFSGNKGLCGRQILEVPACAITTP    779
Pepper_       PKSFEKLSYLQSINVSFNALEGEIPSGGVFANSTLQSFLGNKGLCGRNISEVPACAITNP    777
Potato_       PKSFEKLLYLTSINVSFNVLEGEIPSGGVFANSTLQSFRGNKGLCGRQILEVPACAVTTP    779
              ******* ** *******.****************** ********:*.*******:*.*

Heinz1706_    EQQQSKKKLVLKIVTPMVISFFLIFLLVVSIWIMKRKKKGKSKDVEKVPEMRTYQLISY    839
LA1589_       EQQQSKSKKLVLKIVTPMVISFFLIFLLVVSIWIMKRKKKGKSKDVEKVPEMRTYQLISY    839
Pepper_       EQQ-AKSKKLALKIVTLVVSFFLILLVISIWIKKKRKNGKSKDVEKVPEMRTYQLISY    836
Potato_       EQQQPKSKRLVLKIVTPVVISFFLIFLVVSIWIMKRKKKGKSKDIEKVPEMRTYQLISY    839
              ***  *.*:*.****  *****::* ::***** *:*:.********::*********
```

*FIG. 2F (cont.)*

| | | |
|---|---|---|
| Heinz1706_ | HEIQRATNNFDESNLIGVGGGSGSVYKATLASGIVVAIKVLDLENEEVCKRFDTECEVMRN | 899 |
| LA1589_ | HEIQRATNNFDESNLIGVGGGSGSVYKATLASGIVVAIKVLDLENEEVCKRFDTECEVMRN | 899 |
| Pepper_ | HEIQRATNNFDGSNLIGVGGGSGSVYKGTLPSGIVVAIKVLDLHHEEVCKRFDTECEVMRN | 896 |
| Potato_ | HEIQRATNNFDESNLIGVGGGSGSVYKATLPSGIVVAIKVLDLENEEVCKRFDTECEVVRN | 899 |
| | **********:***************:*:*********:: *****: | |
| Heinz1706_ | VRHKNLVSVITTCSSEHIRAFVLQYMPNGSLDNWLYKEDRHLKLRQRVTIMLDVAMAIEY | 959 |
| LA1589_ | VRHKNLVSVITTCSSEHIRAFVLQYMPNGSLDNWLYKEDRHLKLRQRVTIMLDVAMAIEY | 959 |
| Pepper_ | VRHKNIVSVITTCSSQHIRAFVLQYMPNGSLDNWLYKEDRHLNLLQRVTIMLDTAMAIEY | 956 |
| Potato_ | VRHRNLVSVITTCSSDHIRAFVLQYMPNGSLDNWLYKEDRHLNLRQRVTIMLDVAMAIEY | 959 |
| | ***:*:*******.***********************: :***.*** | |
| Heinz1706_ | LHHGNDTPIVHCDLKPANVLLDEDMVARVGDFGISKILAVSKSMAHTKTLGTLGYIAPEY | 1019 |
| LA1589_ | LHHGNDTPIVHCDLKPANVLLDEDMVARVGDFGISKILAVSKSMAHTKTLGTLGYIAPEY | 1019 |
| Pepper_ | LHHGNDTQIVHCDLKPANVLDDDMVAHVGDFGISKILAVSKFMSHTKTLGTLGYIAPEY | 1016 |
| Potato_ | LHHGNDTPIVHCDLKPANVLLDEDMVARVGDFGISKILAVSKSMAHTKTLGTLGYIAPEY | 1019 |
| | *****.*********.*:**:*********.:.************ | |
| Heinz1706_ | GSEGIVSTRGDVYSYGIMLMEVLAKRRPTGEEIFNENLGLREWITRAFPRTMMEVVDADM | 1079 |
| LA1589_ | GSEGIVSTRGDVYSYGIMLMEVLAKRRPTGEEIFNENLGLREWITRAFPRTMMEVVDADM | 1079 |
| Pepper_ | GSEGIVSTSGDVYSYGIMLMEVLAKRRPTDEEISNENLGLREWITRAFPRTIMEVVDADI | 1076 |
| Potato_ | GSEGIVSTRGDVYSYGIMLMEVLAKRRPTGEEIFNENLGLREWITRAFPRTMMEVVDADI | 1079 |
| | ******.****************.*.:*************:*****: | |
| Heinz1706_ | FHDGEKITSESEICILSMIELALDCTKATPESRITMKDVVKRLNKIKNTFGNIEVN- | 1135 |
| LA1589_ | FHDGEKITSESEICILSMIELALDCTKATPESRITMKDVVKRLNKIKNTFGNIEVN- | 1135 |
| Pepper_ | FHDEENIASKSEICILSMIEVALDCTKEMPESRMTMNDVVKRLYKIKNTFMETEKLV | 1133 |
| Potato_ | FHDGEKITSKSELCILSMIELALDCTKATPESRITMKDVVKRLNKIKNTFLET---- | 1132 |
| | ***..:*:*:*:****::*. ::***** ***: : | |

IDENTICAL POSITIONS 1938
IDENTITY 82.498%
SIMILAR POSITIONS 124
PROGRAM CLUSTALO

*FIG. 2F (cont.)*

| | | |
|---|---|---|
| Heinz1706_ | 1 | MEKHIFLLILAILVQFYFVSSISATISSNETDQEALLAFRNLVTSDSSHFLANNWTKN-T 59 |
| LA1589_ | 1 | MEKHIFLLILAILVQFYFVSSISATISSNETDQEALLAFRNLVTSDSSHFLANNWTKN-T 59 |
| Pepper_ | 1 | MEKHIFLLILLFLVQVYAVASILV-TSSNETDQEALLAFRNLIRSDSSHFLANNWTKNST 59 |
| Potato_ | 1 | MEKHIFLLILAILVQFYFVSSISATIFSNETDQEALLAFRNLVTSDSSQFLANNWTKN-T 59 |
| | | :***** :*::**: ****:::* .:****:* |
| Heinz1706_ | 60 | SFCSWFGVTCSPKRQRVVALTLPNLQLQGTISPSLANLSFLIELNLANNNLHSEIPDGIG 119 |
| LA1589_ | 60 | SFCSWFGVTCSPKRQRVVALTLPNLQLQGTISPSLANLSFLIELNLANNNLHSEIPDGIG 119 |
| Pepper_ | 60 | SFCSWFGVTCSPRRQRVVALNLPDLQLPGTISPSLANLSFLRELNLIGNNSFHGNIPYGIG 119 |
| Potato_ | 60 | SFCSWFGVTCSPKRQRVVALTLPNLQLQGTISPSLANLSFLIELNLTNNNFHGNIPYGIG 119 |
| | | **********:**** :*: ********** *: ** . *:* *** |
| Heinz1706_ | 120 | RLPRLRVIDIQNNQLHGSIPTSLFQHGSVQIISLAFNKLGGEMWNGTWYVPELRVLNLRN 179 |
| LA1589_ | 120 | RLPRLRVIDIQNNQLHGSIPTSLFQHGSVQIISLAFNKLGGEMWNGTWYVPELRVLNLRN 179 |
| Pepper_ | 120 | NLPRLRVIDIQNNQLQGSIPASLFQHQRVQIISLAFNKLSGEMWNGTWYVPELRVLNLRN 179 |
| Potato_ | 120 | HLPRLRVIDIQNNQLQGSIPTSLFQHRSVQIISLAFNKLGGEMWNGTWYVPELRVLNLRN 179 |
| | | :***********::* .*****.************ |
| Heinz1706_ | 180 | NTITGVIPPSIGNATKLMNFSLNGNRINGNIPMEIGNLSQLVELSLSRNQLTGSIPSTLF 239 |
| LA1589_ | 180 | NTITGVIPPSIGNATKLMNFSLNGNRINGNIPMEIGNLSQLVELSLSRNQLTGSIPSTLF 239 |
| Pepper_ | 180 | NTLTGRIPPSIGNATKLMNFSLHGNRISGNIPKEIGNLSQLAELFLSRNQLTGSIPTTLF 239 |
| Potato_ | 180 | NTITGRIPPSIGNATKLMNISLNWNRINGNIPMEIGNLSQLVELSLSRNQLTGSIPSTLF 239 |
| | | : **********: *.*:*****. *********:* |
| Heinz1706_ | 240 | NISSLLVVSLAYNSLSGPLFPDDRRNVLSSNLEHIGVSYNQITGHIPSNICQFTALRVLS 299 |
| LA1589_ | 240 | NISSLLVVSLAYNSLSGPLFPDDRRNVLSSNLEHIGVSYNQITGHIPSNICQFTALRVLS 299 |
| Pepper_ | 240 | NISSLLVASLAFNSLSGPLLLGEG--NILSNLEHLGMSYNQISGRIPSNICQLKELKVLS 297 |
| Potato_ | 240 | NISSLLVVSLAYNSLSGPLFDDRRNVLSSNLEHIGVSYNQITGHISSNICQFKALKVLS 299 |
| | | *****.*:****:: :: **:*:*:*****:*:* *****: * :*** |

FIG. 2F (cont.)

```
Heinz1706_   300  ISYNNITGEIPRNIGCLAKLEEFYIGYNAINGTIPASLGNISTLQNLHCGSNHMEGELPP  359
LA1589_      300  ISYNNITGEIPRNIGCLAKLEEFYIGYNAINGTIPASLGNISTLQNLHCGSNHMEGELPP  359
Pepper_      298  ISFNNITGEMPRNVGCLTKLEELYIGYNPINGRIPTSLGNISTLQKLHCGNNSMIGEIPP  357
Potato_      300  ISYNNITGEIPRNIGCLAKLEEFYIGYNAIDGTIPTSLGNISTLQKLHCGNNHMEGELPP  359
                  **:*****:*** *****.**:*:*:****.:*****:*****:***.*.:*:*:*.**

Heinz1706_   360  ELGKLSNLRQINFEENYNLIGEIPNTIFNISSLEFIAFTENYLSGRIPNLLHLPNLIQLL  419
LA1589_      360  ELGKLSNLRQINFEENYNLIGEIPNTIFNISSLEFIAFTENYLSGRIPNLLHLPNLIQLL  419
Pepper_      358  ELGKLSNLREIDFSENYNLTGEIPNSIFNISLEFIVFSFNYLSGRIPVLLHFPNLIQLF  417
Potato_      360  ELGKLSNLRQINFEENYNLIGEIPNAIFNISSLEFIAFTENYLSGRIPNLLHLPNLIQLL  419
                  ********:*::*.**** ****:******:****.*: *****:*.**:****:

Heinz1706_   420  LANNQLEGEIPRYITNATNLELELSDNLLTGTIPNDLGNLRELRDLFLHHNQLTELGFF  479
LA1589_      420  LANNQLEGEIPRYITNATNLELELSDNLLTGTIPNDLGNLRELRDLFLHHNQLTELGFF  479
Pepper_      418  LANNQLEGEIPRYITNATKLESLDLSVNRLTGTIPNNLGNLRKLKQLFLHHNQLIELGFF  477
Potato_      420  LANNQLEGEIPRYITNATNLELELSDNLLTGSIPYDLGNLRELQELFLHHNQLTELGFF  479
                  ****************.**. :*::*..***:**.:*****:*::*******:*****

Heinz1706_   480  DSLVKCRMLRYVQVGSNPLNDVLPSSIGNLSSTVEYFHIGDAQINGFIPTSTGNMTGLTT  539
LA1589_      480  DSLVKCRMLRYVQVGSNPLNDVLPSSIGNLSSTVEYFHIGDAQINGFIPTSTGNMTGLTT  539
Pepper_      478  DSLVNCRMLQYVQVGSNPLNGVLPSSIGNLSSNVEYFHIGDAQISGFIPTSTGNMSGLTT  537
Potato_      480  DSLVKCRMLRYVQVGSNPLNGVLPSSIGNLSSTVEYFHIGDAQINGFIPTSTGNMSGLTT  539
                  ****:****:**********.****************:********:*****

Heinz1706_   540  LVFQDNSLTGNIPREIRKLKQLQGLFLVNNGLQGLFLVNNGLQDIAEVVCDLSNLVRLALSENELSGVI  599
LA1589_      540  LVFQDNSLTGNIPREIGKLKQLQGLFLVNNGLQDIAEVVCDLSNLVRLALSENELSGVI  599
Pepper_      538  LVFQDNNLTGNIPREIGRLKQLQGLFLINNELQGDITAVVCDLSNLVRLSLSDNELSGVI  597
Potato_      540  LVLQDNNLTGNIPREIGKLKQLQGLFLVNNELQGDIAEVVCDLSNLVRLALSENELSGVI  599
                  **:***.******** :*********:**.**::*: ****************
```

```
Heinz1706_  600  PECLGNLTMLQQLFLGSNKFESKLPLSFWKMSSLLYLNMSRNSIKGEVPSDIGELKAIVA  659
LA1589_     600  PECLGNLTMLQQLFLGSNKFESKLPLSFWKMSSLLYLNMSRNSIKGEVPSDIGELKAIVA  659
Pepper_     598  PNCIGNLSMLQQLFLGSNNFGSELPLSIWKMRGLLFVNISLNSLEGEVPSDIGELKAIVE  657
Potato_     600  PECLGSLTMLQHLFLGSNKFESKLPLSFWKMSSLLYVNMSRNSIEGEVPSDIGELKAIVA  659
                 *:*:**::***:*:*****:*.*******:******.**:**:::**:********:**

Heinz1706_  660  IDISGNHFSGSIPSNLGELQTLKLLSLSNNSFSGPIPFSFSNLKSLEFLDLSLNNLSGTI  719
LA1589_     660  IDISGNHFSGSIPSNLGELQTLKLLSLSNNSFSGPIPFSFSNLKSLEFLDLSLNNLSGTI  719
Pepper_     658  IDISGNHFSGMIPSNLGELQNLQLLKLLSLSNNSFSGPIPLSFSNLISLEILDLSLNNLSGTI  717
Potato_     660  IEISGNHFSGPIPSNLGELQNLKLLSLSNNSFSGPIPLSFSNLKSLEFLDLSLNNLSGTI  719
                 *:***********:*****:* :*:*******.* ****:*.****************

Heinz1706_  720  PKSFEKLLYLTSINVSFNVLEGEIPSGGVFANSTLQSFSGNKGLCGRQILEVPACAITTP  779
LA1589_     720  PKSFEKLLYLTSINVSFNVLEGEIPSGGVFANSTLQSFSGNKGLCGRQILEVPACAITTP  779
Pepper_     718  PKSFEKLSYLQSINVSFNALEGEIPSGGVFANSTLQSFLGNKGLCGRNISEVPACAITNP  777
Potato_     720  PKSFEKLLYLTSINVSFNVLEGEIPSGGVFANSTLQSFRGNKGLCGRQILEVPACAVTTP  779
                 *******.**.*******.***************** ********:*.*******.*.*

Heinz1706_  780  EQQQSKSKKLVLKIVTPMVISFFLIFLLVVSIWIMKRKKKGKSKDVEKVPEMRTYQLISY  839
LA1589_     780  EQQQSKSKKLVLKIVTPMVISFFLIFLLVVSIWIMKRKKKGKSKDVEKVPEMRTYQLISY  839
Pepper_     778  EQQ-AKSKKLALKIVTLVVISFFLILLLVISIWIKRKKKNGKSKDVEKVPEMRTYQLISY  836
Potato_     780  EQQQPKSKRLVLKIVTPVVISFFLIFLLVVSIWIMKRKKKGKDIEKVPEMRTYQLISY  839
                 ***  :***:*.**** :******:*** ***** ****:*..******:*********

Heinz1706_  840  HEIQRATNNFDESNLIGVGGSGSSVYKATLASGIVVAIKVLDLENEEVCKRFDTECEVMRN  899
LA1589_     840  HEIQRATNNFDESNLIGVGGSGSSVYKATLASGIVVAIKVLDLENEEVCKRFDTECEVMRN  899
Pepper_     837  HEIQRATNNFDGSNLIGVGGSGSSVYKGTLPSGIVVAIKVLDLHHEEVCKRFDTECEVVRN  896
Potato_     840  HEIQRATNNFDESNLIGVGGSGSSVYKATLPSGIVVAIKVLDLENEEVCKRFDTECEVVRN  899
                 *********** *************** ** ************ :***********:**
```

*FIG. 2F (cont.)*

```
Heinz1706_   900  VRHKNLVSVITTCSSEHIRAFVLQYMPNGSLDNWLYKEDRHLKLRQRVTIMLDVAMAIEY   959
LA1589_      900  VRHKNLVSVITTCSSEHIRAFVLQYMPNGSLDNWLYKEDRHLKLRQRVTIMLDVAMAIEY   959
Pepper_      897  VRHKNIVSVITTCSSQHIRAFVLQYMPNGSLDNWLYKEDRHLNLLQRVTIMLDTAMAIEY   956
Potato_      900  VRHRNLVSVITTCSSDHIRAFVLQYMPNGSLDNWLYKEDRHLNLRQRVTIMLDVAMAIEY   959
                  ***:*:*********.*****************************:* **********

Heinz1706_   960  LHHGNDTPIVHCDLKPANVLLDEDMVARVGDFGISKILAVSKSMAHTKTLGTLGYIAPEY  1019
LA1589_      960  LHHGNDTPIVHCDLKPANVLLDEDMVARVGDFGISKILAVSKSMAHTKTLGTLGYIAPEY  1019
Pepper_      957  LHHGNDTQIVHCDLKPANVLLDDDMVAHVGDFGISKILAVSKFMSHTKTLGTLGYIAPEY  1016
Potato_      960  LHHGNDTPIVHCDLKPANVLLDEDMVARVGDFGISKILAVSKSMAHTKTLGTLGYIAPEY  1019
                  *******  ************:****:**************  *:*************

Heinz1706_  1020  GSEGIVSTRGDVYSYGIMLMEVLAKRRPTGEEIFNENLGLREWITRAFPRTMMEVVDADM  1079
LA1589_     1020  GSEGIVSTRGDVYSYGIMLMEVLAKRRPTGEEIFNENLGLREWITRAFPRTMMEVVDADM  1079
Pepper_     1017  GSEGIVSTSGDVYSYGIMLMEVLAKRRPTDEEIFNENLGLREWITRAFPRTMEVVDADI  1076
Potato_     1020  GSEGIVSTRGDVYSYGIMLMEVLAKRRPTGEEIFNENLGLREWITRAFPRTMMEVVDADI  1079
                  ******** ********************:***.**********************:

Heinz1706_  1080  FHDGEKITSESEICILSMIELALDCTKATPESRITMKDVVKRLNKIKNTFGNIEVN-     1135
LA1589_     1080  FHDGEKITSESEICILSMIELALDCTKATPESRITMKDVVKRLNKIKNTFGNIEVN-     1135
Pepper_     1077  FHDEENIASKSEICILSMIEVALDCTKEMPESRMTMNDVVKRLYKIKNTFMETEKLV     1133
Potato_     1080  FHDGEKITSKSELCILSMIELALDCTKATPESRITMKDVVKRLNKIKNTFLET---      1132
                  *** .:*:*:**:*******:****** ***** **:***** ******  *    
```

FIG. 2F (cont.)

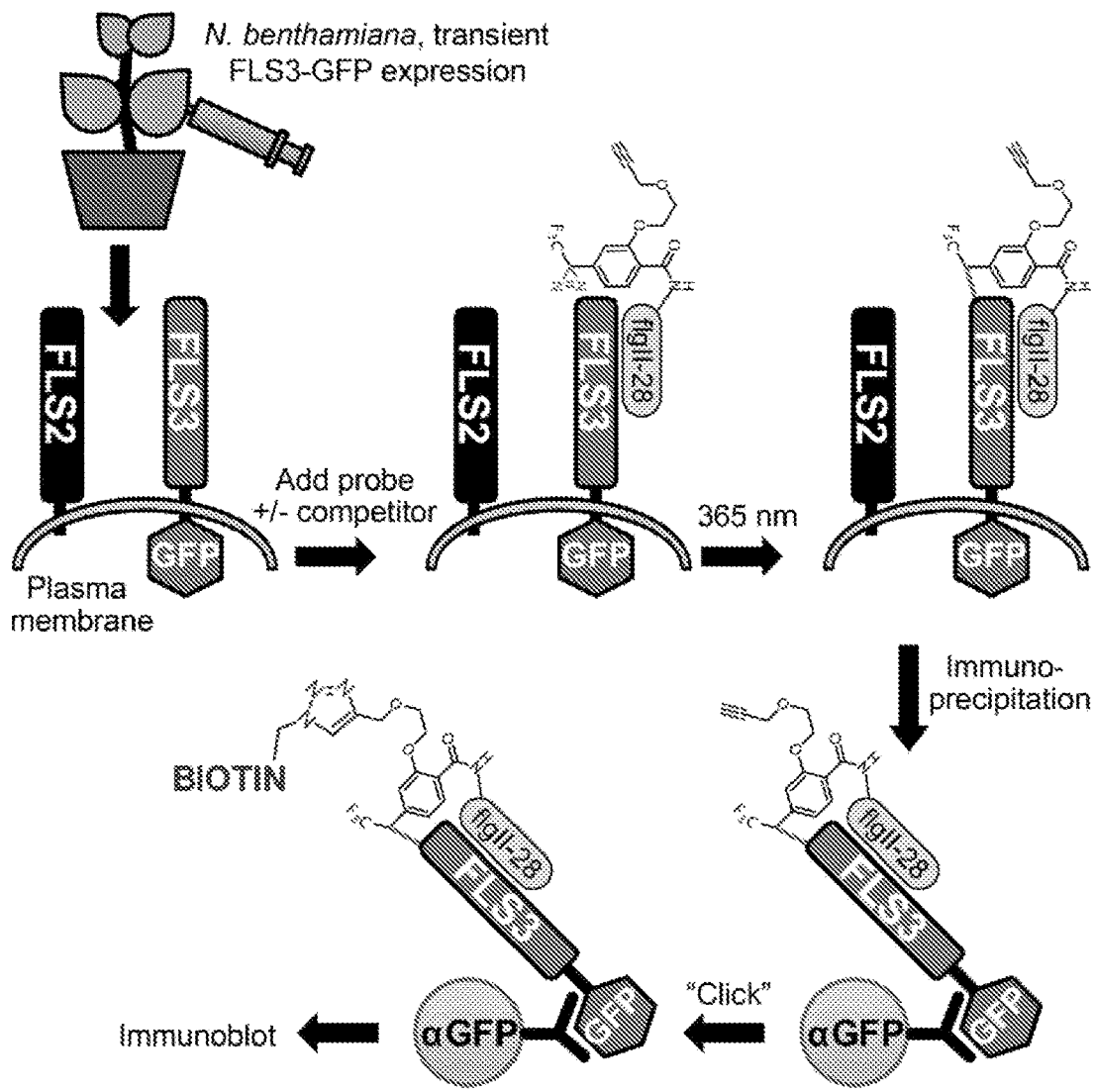
*FIG. 4A*
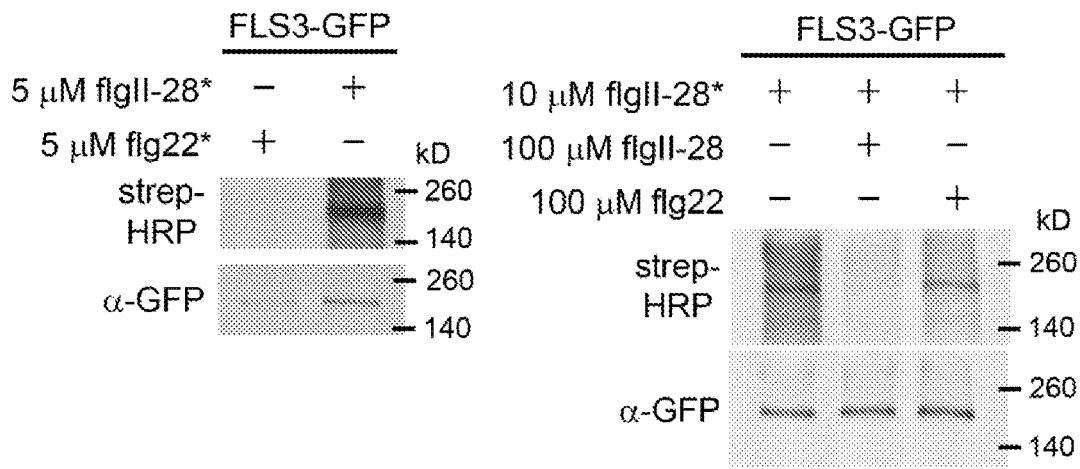
*FIG. 4B*  *FIG. 4C*

SEQUENCE LISTING

```
<160> NUMBER OF SEQ ID NOS: 22

<210> SEQ ID NO 1
<211> LENGTH: 3408
<212> TYPE: DNA
<213> ORGANISM: Solanum lycopersicum

<400> SEQUENCE: 1
atggagaaac acattttctt attgatactt gctatcttag ttcaatttta ctttgtttct      60
tctatatcag ctactatttc ctcaaatgag actgatcaag aagctctact agcttttcga     120
aaccttgtta cgagtgattc tagtcatttt ttagccaata attggacaaa aaacacttca     180
ttttgctctt ggtttggtgt cacttgtagt ccaaaaaggc aaagggttgt agccttgact     240
cttcctaatt tgcaacttca aggcacaatt tcgccgtctt tggccaatct atcttttctc     300
atagagctaa atctcgcaaa caacaactta cacagtgaaa tccctgatgg cattggccgc     360
ttgcctcgtc tacgagtgat tgatattcag aacaatcagc tgcatggaag tattccaaca     420
agtctatttc aacacggag tgttcaaatc atttcattgg ctttcaataa actcggtggt     480
gaaatgtgga acggtacatg gtatgtaccc gaactcagag tcttaaatct caggaacaat     540
accattacag gtgtgatccc tccttctatt ggaaatgcca caaagttgat gaacttcagt     600
ttgaatggga atagaatcaa cggcaacatt ccaatggaga ttggtaatct aagccaactt     660
gttgagttgt cgttgtctcg taatcaatta acaggttcca ttccttcaac attgtttaat     720
atctcctccc ttctcgtcgt gtctctggca tacaatagcc tttcaggtcc tctgtttcct     780
gatgatcgac gtaacgttct ttcatcaaac ctcgagcata taggtgtatc atacaatcaa     840
atcactggtc acattccttc caacatctgt caattcacag ctctcagagt tctgtccata     900
tcatacaaca acataactgg agaaataccg agaaatattg gttgtttagc caagctcgaa     960
```

```
gagtttttata tcggttataa tgcaataaat ggaacaattc ctgcttcatt aggcaatatt    1020
tcaactcttc aaaatcttca ttgcggaagc aatcacatgg agggagaact tcctccagaa    1080
ttaggaaagc tatcaaactt aagacaaatc aatttcgaag aaaattataa tcttattggt    1140
gaaattccga atactatttt caacatatct tctttggagt tcattgcttt cacttttcaac   1200 tacctttcag gtagaattcc gaatcttctt caccttccaa atcttataca acttctctta    1260
gcaaacaatc agctcgaagg tgaaattcct cggtacatca caaatgctac gaatcttgag    1320
ctgttagagc tatcagataa ccttctcaca ggtactattc ctaatgattt aggaaatctt    1380
cgcgagctgc gagatctttt cctacatcat aatcaactta ctgagttggg attctttgat    1440
tctttggtga aatgtaggat gttgagatat gtacaagtgg atcgaatcc gttgaatgat     1500 gttctgccaa gtagtattgg caatctttca tctactgttg aatactttca tattggagat    1560
gcacaaatca atggattcat tcccactagt acaggcaaca tgaccggtct tacaacgcta    1620 gttttttcaag ataacagttt gacaggaaac attcctcgtg agatccgtaa gcttaaacaa   1680
ctccaaggtt tatttctagt taacaatgga ctacaggggg acatagcaga ggtagtatgt    1740
gatttatcga atttggttcg attagctctg tctgaaaatg agctctcggg ggtgattccg    1800
gaatgtttag gaaatcttac catgctacaa caacttttttt taggttctaa caagtttgaa   1860
tcaaagctac ctttaagctt ttggaagatg agtagtcttc tatatttaaa catgtcgcgt    1920
aattctataa agggagaagt tccatcagat atcggagaac ttaaagctat tgtagcaatc    1980
gatatctctg gtaaccattt ctcggggtcg ataccaagca atttggggga acttcaaacc    2040
ttgaagttac tttccttatc gaacaattcg ttttcaggtc caattccatt tcctttttca    2100
aacttgaaaa gcttggaatt cttggatttg tctttgaata acttgtcagg tactattcct    2160
aagtctttcg aaaagctttt gtaccttaca agcatcaacg tctcgtttaa tgttttagaa    2220
ggtgaaatac ctagtggtgg tgtgtttgca aactccaccc tgcaatcatt tagtgggaac    2280
aaaggtctat gtggaaggca aatattggag gttcctgctt gtgctatcac tactcctgaa    2340
caacaacaat caaaatcgaa gaagcttgtg ctaaaaattg tcactccgat ggttatttca    2400
ttctttctga tattcttgtt ggttgtctcg atttggataa tgaaacgaaa gaagaaaggg    2460
aagtccaaag atgttgaaaa ggttccggag atgaggactt atcaattgat ttcttatcat    2520
gagattcaac gagcaactaa caattttgat gaatccaatt tgattggcgt gggaggttct    2580
ggctctgtgt acaaagccac attagctagt ggaattgtgg ttgcaattaa ggtactggat    2640
ttggaaaatg aggaagtatg caaaaggttt gatactgaat gcgaagtgat gagaaatgtt    2700
agacacaaaa accttgtttc ggtgatcact acgtgttcta gtgaacacat aagagccttt    2760
gttctgcagt atatgcccaa cggaagtctt gacaattggt tgtacaaaga agatcgccac    2820
ttaaaacttc gtcaaagagt caccataatg cttgatgtag ctatggcaat tgaatatcta    2880
catcatggta atgacacccc aatagttcat tgtgacctca agccagccaa cgttcttttg    2940
gatgaagata tggtggcgcg tgttggtgat tttggcatct caaagatttt agctgtaagc    3000
aaatccatgg cacatacaaa gacattaggc actcttggat atattgcacc agaatatggc    3060
tcggagggaa tagtgtccac tcgtggtgat gtttacagtt atggcatcat gctgatggag    3120
gttttggcaa aagaaggcc aacaggtgaa gagatattca acgaaaatct tggcttgagg    3180
gagtggataa cgcgagcatt tccaagaact atgatggaag ttgtgacgc ggatatgttt     3240 catgatggag aaaaaattac ttccgaaagt gaaatatgca tactctccat gatagaactg    3300
```

-continued

```
gctttagatt gcacaaaggc aacaccagaa tcaaggataa ccatgaaaga tgtagtcaag    3360
aggcttaaca aaataaagaa cacatttgga aacatagaag taaattag                 3408
```

<210> SEQ ID NO 2
<211> LENGTH: 1135
<212> TYPE: PRT
<213> ORGANISM: Solanum lycopersicum

<400> SEQUENCE: 2

```
Met Glu Lys His Ile Phe Leu Leu Ile Leu Ala Ile Leu Val Gln Phe
1               5                   10                  15

Tyr Phe Val Ser Ser Ile Ser Ala Thr Ile Ser Ser Asn Glu Thr Asp
            20                  25                  30

Gln Glu Ala Leu Leu Ala Phe Arg Asn Leu Val Thr Ser Asp Ser Ser
        35                  40                  45

His Phe Leu Ala Asn Asn Trp Thr Lys Asn Thr Ser Phe Cys Ser Trp
    50                  55                  60

Phe Gly Val Thr Cys Ser Pro Lys Arg Gln Arg Val Val Ala Leu Thr
65                  70                  75                  80

Leu Pro Asn Leu Gln Leu Gln Gly Thr Ile Ser Pro Ser Leu Ala Asn
                85                  90                  95

Leu Ser Phe Leu Ile Glu Leu Asn Leu Ala Asn Asn Asn Leu His Ser
            100                 105                 110

Glu Ile Pro Asp Gly Ile Gly Arg Leu Pro Arg Leu Arg Val Ile Asp
        115                 120                 125

Ile Gln Asn Asn Gln Leu His Gly Ser Ile Pro Thr Ser Leu Phe Gln
    130                 135                 140

His Gly Ser Val Gln Ile Ile Ser Leu Ala Phe Asn Lys Leu Gly Gly
145                 150                 155                 160

Glu Met Trp Asn Gly Thr Trp Tyr Val Pro Glu Leu Arg Val Leu Asn
                165                 170                 175

Leu Arg Asn Asn Thr Ile Thr Gly Val Ile Pro Pro Ser Ile Gly Asn
            180                 185                 190

Ala Thr Lys Leu Met Asn Phe Ser Leu Asn Gly Asn Arg Ile Asn Gly
        195                 200                 205

Asn Ile Pro Met Glu Ile Gly Asn Leu Ser Gln Leu Val Glu Leu Ser
    210                 215                 220

Leu Ser Arg Asn Gln Leu Thr Gly Ser Ile Pro Ser Thr Leu Phe Asn
225                 230                 235                 240

Ile Ser Ser Leu Leu Val Val Ser Leu Ala Tyr Asn Ser Leu Ser Gly
                245                 250                 255

Pro Leu Phe Pro Asp Asp Arg Arg Asn Val Leu Ser Ser Asn Leu Glu
            260                 265                 270

His Ile Gly Val Ser Tyr Asn Gln Ile Thr Gly His Ile Pro Ser Asn
        275                 280                 285

Ile Cys Gln Phe Thr Ala Leu Arg Val Leu Ser Ile Ser Tyr Asn Asn
    290                 295                 300

Ile Thr Gly Glu Ile Pro Arg Asn Ile Gly Cys Leu Ala Lys Leu Glu
305                 310                 315                 320

Glu Phe Tyr Ile Gly Tyr Asn Ala Ile Asn Gly Thr Ile Pro Ala Ser
                325                 330                 335

Leu Gly Asn Ile Ser Thr Leu Gln Asn Leu His Cys Gly Ser Asn His
            340                 345                 350

Met Glu Gly Glu Leu Pro Pro Glu Leu Gly Lys Leu Ser Asn Leu Arg
```

```
            355                 360                 365
Gln Ile Asn Phe Glu Glu Asn Tyr Asn Leu Ile Gly Glu Ile Pro Asn
        370                 375                 380

Thr Ile Phe Asn Ile Ser Ser Leu Glu Phe Ile Ala Phe Thr Phe Asn
385                 390                 395                 400

Tyr Leu Ser Gly Arg Ile Pro Asn Leu Leu His Leu Pro Asn Leu Ile
            405                 410                 415

Gln Leu Leu Leu Ala Asn Asn Gln Leu Glu Gly Glu Ile Pro Arg Tyr
        420                 425                 430

Ile Thr Asn Ala Thr Asn Leu Glu Leu Glu Leu Ser Asp Asn Leu
            435                 440                 445

Leu Thr Gly Thr Ile Pro Asn Asp Leu Gly Asn Leu Arg Glu Leu Arg
        450                 455                 460

Asp Leu Phe Leu His His Asn Gln Leu Thr Glu Leu Gly Phe Phe Asp
465                 470                 475                 480

Ser Leu Val Lys Cys Arg Met Leu Arg Tyr Val Gln Val Gly Ser Asn
            485                 490                 495

Pro Leu Asn Asp Val Leu Pro Ser Ser Ile Gly Asn Leu Ser Ser Thr
        500                 505                 510

Val Glu Tyr Phe His Ile Gly Asp Ala Gln Ile Asn Gly Phe Ile Pro
            515                 520                 525

Thr Ser Thr Gly Asn Met Thr Gly Leu Thr Thr Leu Val Phe Gln Asp
        530                 535                 540

Asn Ser Leu Thr Gly Asn Ile Pro Arg Glu Ile Arg Lys Leu Lys Gln
545                 550                 555                 560

Leu Gln Gly Leu Phe Leu Val Asn Asn Gly Leu Gln Gly Asp Ile Ala
            565                 570                 575

Glu Val Val Cys Asp Leu Ser Asn Leu Val Arg Leu Ala Leu Ser Glu
        580                 585                 590

Asn Glu Leu Ser Gly Val Ile Pro Glu Cys Leu Gly Asn Leu Thr Met
        595                 600                 605

Leu Gln Gln Leu Phe Leu Gly Ser Asn Lys Phe Glu Ser Lys Leu Pro
        610                 615                 620

Leu Ser Phe Trp Lys Met Ser Ser Leu Leu Tyr Leu Asn Met Ser Arg
625                 630                 635                 640

Asn Ser Ile Lys Gly Glu Val Pro Ser Asp Ile Gly Glu Leu Lys Ala
            645                 650                 655

Ile Val Ala Ile Asp Ile Ser Gly Asn His Phe Ser Gly Ser Ile Pro
            660                 665                 670

Ser Asn Leu Gly Glu Leu Gln Thr Leu Lys Leu Leu Ser Leu Ser Asn
        675                 680                 685

Asn Ser Phe Ser Gly Pro Ile Pro Phe Ser Phe Asn Leu Lys Ser
        690                 695                 700

Leu Glu Phe Leu Asp Leu Ser Leu Asn Asn Leu Ser Gly Thr Ile Pro
705                 710                 715                 720

Lys Ser Phe Glu Lys Leu Leu Tyr Leu Thr Ser Ile Asn Val Ser Phe
            725                 730                 735

Asn Val Leu Glu Gly Glu Ile Pro Ser Gly Val Phe Ala Asn Ser
            740                 745                 750

Thr Leu Gln Ser Phe Ser Gly Asn Lys Gly Leu Cys Gly Arg Gln Ile
            755                 760                 765

Leu Glu Val Pro Ala Cys Ala Ile Thr Thr Pro Glu Gln Gln Gln Ser
        770                 775                 780
```

```
Lys Ser Lys Lys Leu Val Leu Lys Ile Val Thr Pro Met Val Ile Ser
785                 790                 795                 800

Phe Phe Leu Ile Phe Leu Leu Val Val Ser Ile Trp Ile Met Lys Arg
                805                 810                 815

Lys Lys Lys Gly Lys Ser Lys Asp Val Glu Lys Val Pro Glu Met Arg
            820                 825                 830

Thr Tyr Gln Leu Ile Ser Tyr His Glu Ile Gln Arg Ala Thr Asn Asn
            835                 840                 845

Phe Asp Glu Ser Asn Leu Ile Gly Val Gly Gly Ser Gly Ser Val Tyr
850                 855                 860

Lys Ala Thr Leu Ala Ser Gly Ile Val Val Ala Ile Lys Val Leu Asp
865                 870                 875                 880

Leu Glu Asn Glu Glu Val Cys Lys Arg Phe Asp Thr Glu Cys Glu Val
                885                 890                 895

Met Arg Asn Val Arg His Lys Asn Leu Val Ser Val Ile Thr Thr Cys
                900                 905                 910

Ser Ser Glu His Ile Arg Ala Phe Val Leu Gln Tyr Met Pro Asn Gly
            915                 920                 925

Ser Leu Asp Asn Trp Leu Tyr Lys Glu Asp Arg His Leu Lys Leu Arg
930                 935                 940

Gln Arg Val Thr Ile Met Leu Asp Val Ala Met Ala Ile Glu Tyr Leu
945                 950                 955                 960

His His Gly Asn Asp Thr Pro Ile Val His Cys Asp Leu Lys Pro Ala
                965                 970                 975

Asn Val Leu Leu Asp Glu Asp Met Val Ala Arg Val Gly Asp Phe Gly
                980                 985                 990

Ile Ser Lys Ile Leu Ala Val Ser  Lys Ser Met Ala His  Thr Lys Thr
            995                 1000                1005

Leu Gly  Thr Leu Gly Tyr Ile  Ala Pro Glu Tyr Gly  Ser Glu Gly
    1010                1015                1020

Ile Val  Ser Thr Arg Gly Asp  Val Tyr Ser Tyr Gly  Ile Met Leu
    1025                1030                1035

Met Glu  Val Leu Ala Lys Arg  Arg Pro Thr Gly Glu  Glu Ile Phe
    1040                1045                1050

Asn Glu  Asn Leu Gly Leu Arg  Glu Trp Ile Thr Arg  Ala Phe Pro
    1055                1060                1065

Arg Thr  Met Met Glu Val Val  Asp Ala Asp Met Phe  His Asp Gly
    1070                1075                1080

Glu Lys  Ile Thr Ser Glu Ser  Glu Ile Cys Ile Leu  Ser Met Ile
    1085                1090                1095

Glu Leu  Ala Leu Asp Cys Thr  Lys Ala Thr Pro Glu  Ser Arg Ile
    1100                1105                1110

Thr Met  Lys Asp Val Val Lys  Arg Leu Asn Lys Ile  Lys Asn Thr
    1115                1120                1125

Phe Gly  Asn Ile Glu Val Asn
    1130                1135

<210> SEQ ID NO 3
<211> LENGTH: 3525
<212> TYPE: DNA
<213> ORGANISM: Solanum pimpinellifolium

<400> SEQUENCE: 3
atggagaaac acattttctt attgatactt gctatcttag ttcaattttta ctttgtttct    60
```

```
tctatatcag ctactatttc ctcaaatgag actgatcaag aagctctact agcttttcga    120
aaccttgtta cgagtgattc tagtcatttt ttagccaata attggacaaa aaacacttca    180
ttttgctctt ggtttggtgt cacttgtagt ccaaaaaggc aaagggttgt agccttgact    240
cttcctaatt tgcaacttca aggcacaatt tcgccgtctt tggccaatct atcttttctc    300
atagggctaa atctcgcgaa caacaactta cacagtgaaa tccctgatgg cattggccgc    360
ttgcctcgtc tacgagtgat tgatattcag aacaatcagc tgcatggaag tattccaaca    420
agtctatttc aacacgggag tgttcaaatc atttcattgg ctttcaataa actcggtggt    480
gaaatgtgga acgtacatg gtatgtaccc gaactcagag tcttaaatct caggaacaat    540
accattacag gtgtgatccc tccttctatt ggaaatgcca caaagttgat gaacttcagt    600
ttgaatggga atagaatcaa cggcaacatt ccaatggaga ttggtaatct aagccaactt    660
gttgagttat cgttgtctcg taatcaatta acaggttcca ttccttcaac attgtttaat    720
atctcctccc ttctcgtcgt gtctctggca tacaatagcc tttcaggtcc tctgtttcct    780
gatgatcgac gtaacgttct ttcatcaaac ctcgagcata taggtgtatc atacaatcaa    840
atcactggtc acattccttc caacatctgt caattcacag ctctcagagt tctgtccata    900
tcatacaaca cataactgg agaaatacccg agaaatattg gttgtttagc caagctcgaa    960
gagttttata tcggttataa tgcaataaat ggaacaattc ctgcttcatt aggcaatatt    1020
tcaactcttc aaaatcttca ttgcggaagc aatcacatgg agggagaact tcctccggaa    1080
ttaggaaagc tatcaaactt aagcaaaatc aatttcgaag aaaattataa tcttattggt    1140
gaaattccga atactatttt caacatatct tctttggagt tcattgcttt cactttcaac    1200 taccttcag gtagaattcc gaatcttctt caccttccaa atcttataca acttctctta    1260
gcaaacaatc agctcgaagg tgaaattcct cggtacatca caaatgctac gaatcttgag    1320
ctgttagagc tatcagataa ccttctcaca ggtactattc ctaatgattt aggaaatctt    1380
cgcgagctgc gagatctttt cctacatcat aatcaactta ctgagttggg attctttgat    1440
tctttggtga atgtaggat gttgagatat gtacaagtgg gatcgaatcc gttgaatgat    1500
gttctgccaa gtagtattgg caatctttca tctactgttg aatactttca tattggagat    1560
gcacaaatca atggattcat tcccactagt acaggcaaca tgaccggtct tacaacgcta    1620 gttttcaag ataacagttt gacaggaaac attcctcgtg agatcggtaa gcttaaacaa    1680
ctccaaggtt tatttctagt taacaatgga ctacagggg acatagcaga ggtagtatgt    1740
gatttatcga atttggttcg attagctctg tctgaaaatg agctctcggg ggtgattccg    1800
gaatgtttag gaatcttac catgctacaa caactttttt taggttctaa caagtttgaa    1860
tcaaagctac ctttaagctt ttggaagatg agtagtcttc tctatttaaa catgtcgcgt    1920
aattctataa agggagaagt tccatcagat atcggagaac ttaaagctat tgtagcaatc    1980
gatatctctg gtaaccattt ctcggggtcg ataccaagca atttggggga acttcaaacc    2040
ttgaagttac tttccttatc gaacaattcg ttttcaggtc caattccatt ttcctttca     2100 aacttgaaaa gcttggaatt cttggatttg tctttgaata acttgtcagg tactattcct    2160
aagtctttcg aaaagctttt gtaccttaca agcatcaacg tctcgtttaa tgttttagaa    2220
ggtgaaatac ctagtggtgg tgtgtttgca aactccaccc tgcaatcatt tagtgggaac    2280
aaaggtctat gtggaaggca atattggag gttcctgctt gtgctatcac tactcctgaa    2340
caacaacaat caaaatcgaa gaagcttgtg ctaaaaattg tcactccgat ggttatttca    2400
```

```
ttctttctga tattcttgtt ggttgtctcg atttggataa tgaaacgaaa gaagaaaggg    2460
aagtccaaag atgttgaaaa ggttccggag atgaggactt atcaattgat ttcttatcat    2520
gagattcaac gagcaactaa caattttgat gaatccaatt tgattggcgt gggaggttct    2580
ggctctgtgt acaaagccac attagctagt ggaattgtgg ttgcaattaa ggtactggat    2640
ttggaaaatg aggaagtatg caaaaggttt gatactgaat gcgaagtgat gagaaatgtt    2700
agacacaaaa accttgtttc ggtgatcact acgtgttcta gtaacacat aagagccttt     2760 gttctgcagt atatgcccaa cggaagtctt gacaattggt tgtacaaaga agatcgccac    2820
ttaaaacttc gtcaaagagt caccataatg cttgatgtag ctatggcaat tgaatatcta    2880
catcatggta atgacacccc aatagttcat tgtgacctca agccagccaa cgttctttg    2940 gatgaagata tggtggcgcg tgttggtgat tttggcatct caaagatttt agctgtaagc    3000
aaatccatgg cacatacaaa gacattaggc actcttggat atattgcacc aggtatatat    3060
actactatac tagtctcttt ccatttcatt tatgtatcga agacctttcg ttattgttat    3120
atcagatgag tatttgagta atacttttt tcattttcgt tcttttaaga atatggctcg     3180
gagggaatag tgtccactcg tggtgatgtt tacagttatg gcatcatgct gatggaggtt    3240
ttggcaaaaa gaaggccaac aggtgaagag atattcaacg aaaatcttgg cttgagggag    3300
tggataacgc gagcatttcc aagaactatg atggaagttg tggacgcgga tatgtttcat    3360
gatggagaaa aaattacttc cgaaagtgaa atatgcatac tctccatgat agaactggct    3420
ttagattgca caaaggcaac accagaatca aggataacca tgaaagatgt agtcaagagg    3480
cttaacaaaa taaagaacac atttggaaac atagaagtaa attag                   3525
```

<210> SEQ ID NO 4
<211> LENGTH: 1135
<212> TYPE: PRT
<213> ORGANISM: Solanum pimpinellifolium

<400> SEQUENCE: 4

```
Met Glu Lys His Ile Phe Leu Leu Ile Leu Ala Ile Leu Val Gln Phe
1               5                   10                  15

Tyr Phe Val Ser Ser Ile Ser Ala Thr Ile Ser Ser Asn Glu Thr Asp
                20                  25                  30

Gln Glu Ala Leu Leu Ala Phe Arg Asn Leu Val Thr Ser Asp Ser Ser
            35                  40                  45

His Phe Leu Ala Asn Asn Trp Thr Lys Asn Thr Ser Phe Cys Ser Trp
        50                  55                  60

Phe Gly Val Thr Cys Ser Pro Lys Arg Gln Arg Val Val Ala Leu Thr
65                  70                  75                  80

Leu Pro Asn Leu Gln Leu Gln Gly Thr Ile Ser Pro Ser Leu Ala Asn
                85                  90                  95

Leu Ser Phe Leu Ile Gly Leu Asn Leu Ala Asn Asn Asn Leu His Ser
            100                 105                 110

Glu Ile Pro Asp Gly Ile Gly Arg Leu Pro Arg Leu Arg Val Ile Asp
        115                 120                 125

Ile Gln Asn Asn Gln Leu His Gly Ser Ile Pro Thr Ser Leu Phe Gln
    130                 135                 140

His Gly Ser Val Gln Ile Ile Ser Leu Ala Phe Asn Lys Leu Gly Gly
145                 150                 155                 160

Glu Met Trp Asn Gly Thr Trp Tyr Val Pro Glu Leu Arg Val Leu Asn
                165                 170                 175
```

```
Leu Arg Asn Asn Thr Ile Thr Gly Val Ile Pro Ser Ile Gly Asn
            180                 185                 190

Ala Thr Lys Leu Met Asn Phe Ser Leu Asn Gly Asn Arg Ile Asn Gly
        195                 200                 205

Asn Ile Pro Met Glu Ile Gly Asn Leu Ser Gln Leu Val Glu Leu Ser
    210                 215                 220

Leu Ser Arg Asn Gln Leu Thr Gly Ser Ile Pro Ser Thr Leu Phe Asn
225                 230                 235                 240

Ile Ser Ser Leu Leu Val Val Ser Leu Ala Tyr Asn Ser Leu Ser Gly
                245                 250                 255

Pro Leu Phe Pro Asp Asp Arg Arg Asn Val Leu Ser Ser Asn Leu Glu
            260                 265                 270

His Ile Gly Val Ser Tyr Asn Gln Ile Thr Gly His Ile Pro Ser Asn
        275                 280                 285

Ile Cys Gln Phe Thr Ala Leu Arg Val Leu Ser Ile Ser Tyr Asn Asn
    290                 295                 300

Ile Thr Gly Glu Ile Pro Arg Asn Ile Gly Cys Leu Ala Lys Leu Glu
305                 310                 315                 320

Glu Phe Tyr Ile Gly Tyr Asn Ala Ile Asn Gly Thr Ile Pro Ala Ser
                325                 330                 335

Leu Gly Asn Ile Ser Thr Leu Gln Asn Leu His Cys Gly Ser Asn His
            340                 345                 350

Met Glu Gly Glu Leu Pro Pro Glu Leu Gly Lys Leu Ser Asn Leu Arg
        355                 360                 365

Gln Ile Asn Phe Glu Glu Asn Tyr Asn Leu Ile Gly Glu Ile Pro Asn
    370                 375                 380

Thr Ile Phe Asn Ile Ser Ser Leu Glu Phe Ile Ala Phe Thr Phe Asn
385                 390                 395                 400

Tyr Leu Ser Gly Arg Ile Pro Asn Leu Leu His Leu Pro Asn Leu Ile
                405                 410                 415

Gln Leu Leu Leu Ala Asn Asn Gln Leu Glu Gly Glu Ile Pro Arg Tyr
            420                 425                 430

Ile Thr Asn Ala Thr Asn Leu Glu Leu Leu Glu Leu Ser Asp Asn Leu
        435                 440                 445

Leu Thr Gly Thr Ile Pro Asn Asp Leu Gly Asn Leu Arg Glu Leu Arg
    450                 455                 460

Asp Leu Phe Leu His His Asn Gln Leu Thr Glu Leu Gly Phe Phe Asp
465                 470                 475                 480

Ser Leu Val Lys Cys Arg Met Leu Arg Tyr Val Gln Val Gly Ser Asn
                485                 490                 495

Pro Leu Asn Asp Val Leu Pro Ser Ser Ile Gly Asn Leu Ser Ser Thr
            500                 505                 510

Val Glu Tyr Phe His Ile Gly Asp Ala Gln Ile Asn Gly Phe Ile Pro
        515                 520                 525

Thr Ser Thr Gly Asn Met Thr Gly Leu Thr Thr Leu Val Phe Gln Asp
    530                 535                 540

Asn Ser Leu Thr Gly Asn Ile Pro Arg Glu Ile Gly Lys Leu Lys Gln
545                 550                 555                 560

Leu Gln Gly Leu Phe Leu Val Asn Asn Gly Leu Gln Gly Asp Ile Ala
                565                 570                 575

Glu Val Val Cys Asp Leu Ser Asn Leu Val Arg Leu Ala Leu Ser Glu
            580                 585                 590

Asn Glu Leu Ser Gly Val Ile Pro Glu Cys Leu Gly Asn Leu Thr Met
```

-continued

```
            595                 600                 605
Leu Gln Gln Leu Phe Leu Gly Ser Asn Lys Phe Glu Ser Lys Leu Pro
            610                 615                 620
Leu Ser Phe Trp Lys Met Ser Ser Leu Leu Tyr Leu Asn Met Ser Arg
625                 630                 635                 640
Asn Ser Ile Lys Gly Glu Val Pro Ser Asp Ile Gly Glu Leu Lys Ala
                    645                 650                 655
Ile Val Ala Ile Asp Ile Ser Gly Asn His Phe Ser Gly Ser Ile Pro
                    660                 665                 670
Ser Asn Leu Gly Glu Leu Gln Thr Leu Lys Leu Leu Ser Leu Ser Asn
                    675                 680                 685
Asn Ser Phe Ser Gly Pro Ile Pro Phe Ser Phe Ser Asn Leu Lys Ser
            690                 695                 700
Leu Glu Phe Leu Asp Leu Ser Leu Asn Asn Leu Ser Gly Thr Ile Pro
705                 710                 715                 720
Lys Ser Phe Glu Lys Leu Leu Tyr Leu Thr Ser Ile Asn Val Ser Phe
                    725                 730                 735
Asn Val Leu Glu Gly Glu Ile Pro Ser Gly Gly Val Phe Ala Asn Ser
                    740                 745                 750
Thr Leu Gln Ser Phe Ser Gly Asn Lys Gly Leu Cys Gly Arg Gln Ile
            755                 760                 765
Leu Glu Val Pro Ala Cys Ala Ile Thr Thr Pro Glu Gln Gln Gln Ser
            770                 775                 780
Lys Ser Lys Lys Leu Val Leu Lys Ile Val Thr Pro Met Val Ile Ser
785                 790                 795                 800
Phe Phe Leu Ile Phe Leu Leu Val Val Ser Ile Trp Ile Met Lys Arg
                    805                 810                 815
Lys Lys Lys Gly Lys Ser Lys Asp Val Glu Lys Val Pro Glu Met Arg
                    820                 825                 830
Thr Tyr Gln Leu Ile Ser Tyr His Glu Ile Gln Arg Ala Thr Asn Asn
            835                 840                 845
Phe Asp Glu Ser Asn Leu Ile Gly Val Gly Gly Ser Gly Ser Val Tyr
            850                 855                 860
Lys Ala Thr Leu Ala Ser Gly Ile Val Val Ala Ile Lys Val Leu Asp
865                 870                 875                 880
Leu Glu Asn Glu Glu Val Cys Lys Arg Phe Asp Thr Glu Cys Glu Val
                    885                 890                 895
Met Arg Asn Val Arg His Lys Asn Leu Val Ser Val Ile Thr Thr Cys
                    900                 905                 910
Ser Ser Glu His Ile Arg Ala Phe Val Leu Gln Tyr Met Pro Asn Gly
            915                 920                 925
Ser Leu Asp Asn Trp Leu Tyr Lys Glu Asp Arg His Leu Lys Leu Arg
            930                 935                 940
Gln Arg Val Thr Ile Met Leu Asp Val Ala Met Ala Ile Glu Tyr Leu
945                 950                 955                 960
His His Gly Asn Asp Thr Pro Ile Val His Cys Asp Leu Lys Pro Ala
                    965                 970                 975
Asn Val Leu Leu Asp Glu Asp Met Val Ala Arg Val Gly Asp Phe Gly
                    980                 985                 990
Ile Ser Lys Ile Leu Ala Val Ser  Lys Ser Met Ala His  Thr Lys Thr
            995                 1000                1005
Leu Gly  Thr Leu Gly Tyr Ile  Ala Pro Glu Tyr Gly  Ser Glu Gly
            1010                1015                1020
```

```
Ile Val Ser Thr Arg Gly Asp Val Tyr Ser Tyr Gly Ile Met Leu
1025                1030                1035

Met Glu Val Leu Ala Lys Arg Arg Pro Thr Gly Glu Glu Ile Phe
1040                1045                1050

Asn Glu Asn Leu Gly Leu Arg Glu Trp Ile Thr Arg Ala Phe Pro
1055                1060                1065

Arg Thr Met Met Glu Val Val Asp Ala Asp Met Phe His Asp Gly
1070                1075                1080

Glu Lys Ile Thr Ser Glu Ser Glu Ile Cys Ile Leu Ser Met Ile
1085                1090                1095

Glu Leu Ala Leu Asp Cys Thr Lys Ala Thr Pro Glu Ser Arg Ile
1100                1105                1110

Thr Met Lys Asp Val Val Lys Arg Leu Asn Lys Ile Lys Asn Thr
1115                1120                1125

Phe Gly Asn Ile Glu Val Asn
1130                1135

<210> SEQ ID NO 5
<211> LENGTH: 1135
<212> TYPE: PRT
<213> ORGANISM: Artificial
<220> FEATURE:
<223> OTHER INFORMATION: Conserved protein sequence for FLS3
<220> FEATURE:
<221> NAME/KEY: MISC_FEATURE
<222> LOCATION: (102)..(102)
<223> OTHER INFORMATION: Xaa at position 102 is Glu or Gly
<220> FEATURE:
<221> NAME/KEY: MISC_FEATURE
<222> LOCATION: (556)..(556)
<223> OTHER INFORMATION: Xaa at position 556 is Arg or Gly

<400> SEQUENCE: 5

Met Glu Lys His Ile Phe Leu Leu Ile Leu Ala Ile Leu Val Gln Phe
1               5                   10                  15

Tyr Phe Val Ser Ser Ile Ser Ala Thr Ile Ser Ser Asn Glu Thr Asp
                20                  25                  30

Gln Glu Ala Leu Leu Ala Phe Arg Asn Leu Val Thr Ser Asp Ser Ser
            35                  40                  45

His Phe Leu Ala Asn Asn Trp Thr Lys Asn Thr Ser Phe Cys Ser Trp
        50                  55                  60

Phe Gly Val Thr Cys Ser Pro Lys Arg Gln Arg Val Val Ala Leu Thr
65                  70                  75                  80

Leu Pro Asn Leu Gln Leu Gln Gly Thr Ile Ser Pro Ser Leu Ala Asn
                85                  90                  95

Leu Ser Phe Leu Ile Xaa Leu Asn Leu Ala Asn Asn Asn Leu His Ser
                100                 105                 110

Glu Ile Pro Asp Gly Ile Gly Arg Leu Pro Arg Leu Arg Val Ile Asp
            115                 120                 125

Ile Gln Asn Asn Gln Leu His Gly Ser Ile Pro Thr Ser Leu Phe Gln
        130                 135                 140

His Gly Ser Val Gln Ile Ile Ser Leu Ala Phe Asn Lys Leu Gly Gly
145                 150                 155                 160

Glu Met Trp Asn Gly Thr Trp Tyr Val Pro Glu Leu Arg Val Leu Asn
                165                 170                 175

Leu Arg Asn Asn Thr Ile Thr Gly Val Ile Pro Pro Ser Ile Gly Asn
                180                 185                 190
```

-continued

```
Ala Thr Lys Leu Met Asn Phe Ser Leu Asn Gly Asn Arg Ile Asn Gly
            195                 200                 205

Asn Ile Pro Met Glu Ile Gly Asn Leu Ser Gln Leu Val Glu Leu Ser
        210                 215                 220

Leu Ser Arg Asn Gln Leu Thr Gly Ser Ile Pro Ser Thr Leu Phe Asn
225                 230                 235                 240

Ile Ser Ser Leu Leu Val Val Ser Leu Ala Tyr Asn Ser Leu Ser Gly
                245                 250                 255

Pro Leu Phe Pro Asp Asp Arg Arg Asn Val Leu Ser Ser Asn Leu Glu
            260                 265                 270

His Ile Gly Val Ser Tyr Asn Gln Ile Thr Gly His Ile Pro Ser Asn
        275                 280                 285

Ile Cys Gln Phe Thr Ala Leu Arg Val Leu Ser Ile Ser Tyr Asn Asn
    290                 295                 300

Ile Thr Gly Glu Ile Pro Arg Asn Ile Gly Cys Leu Ala Lys Leu Glu
305                 310                 315                 320

Glu Phe Tyr Ile Gly Tyr Asn Ala Ile Asn Gly Thr Ile Pro Ala Ser
                325                 330                 335

Leu Gly Asn Ile Ser Thr Leu Gln Asn Leu His Cys Gly Ser Asn His
            340                 345                 350

Met Glu Gly Glu Leu Pro Pro Glu Leu Gly Lys Leu Ser Asn Leu Arg
        355                 360                 365

Gln Ile Asn Phe Glu Glu Asn Tyr Asn Leu Ile Gly Glu Ile Pro Asn
    370                 375                 380

Thr Ile Phe Asn Ile Ser Ser Leu Glu Phe Ile Ala Phe Thr Phe Asn
385                 390                 395                 400

Tyr Leu Ser Gly Arg Ile Pro Asn Leu Leu His Leu Pro Asn Leu Ile
                405                 410                 415

Gln Leu Leu Leu Ala Asn Asn Gln Leu Glu Gly Glu Ile Pro Arg Tyr
            420                 425                 430

Ile Thr Asn Ala Thr Asn Leu Glu Leu Leu Glu Leu Ser Asp Asn Leu
        435                 440                 445

Leu Thr Gly Thr Ile Pro Asn Asp Leu Gly Asn Leu Arg Glu Leu Arg
    450                 455                 460

Asp Leu Phe Leu His His Asn Gln Leu Thr Glu Leu Gly Phe Phe Asp
465                 470                 475                 480

Ser Leu Val Lys Cys Arg Met Leu Arg Tyr Val Gln Val Gly Ser Asn
                485                 490                 495

Pro Leu Asn Asp Val Leu Pro Ser Ser Ile Gly Asn Leu Ser Ser Thr
            500                 505                 510

Val Glu Tyr Phe His Ile Gly Asp Ala Gln Ile Asn Gly Phe Ile Pro
        515                 520                 525

Thr Ser Thr Gly Asn Met Thr Gly Leu Thr Thr Leu Val Phe Gln Asp
    530                 535                 540

Asn Ser Leu Thr Gly Asn Ile Pro Arg Glu Ile Xaa Lys Leu Lys Gln
545                 550                 555                 560

Leu Gln Gly Leu Phe Leu Val Asn Asn Gly Leu Gln Gly Asp Ile Ala
                565                 570                 575

Glu Val Val Cys Asp Leu Ser Asn Leu Val Arg Leu Ala Leu Ser Glu
            580                 585                 590

Asn Glu Leu Ser Gly Val Ile Pro Glu Cys Leu Gly Asn Leu Thr Met
        595                 600                 605

Leu Gln Gln Leu Phe Leu Gly Ser Asn Lys Phe Glu Ser Lys Leu Pro
```

-continued

```
                610                 615                 620
Leu Ser Phe Trp Lys Met Ser Ser Leu Leu Tyr Leu Asn Met Ser Arg
625                 630                 635                 640

Asn Ser Ile Lys Gly Glu Val Pro Ser Asp Ile Gly Glu Leu Lys Ala
                645                 650                 655

Ile Val Ala Ile Asp Ile Ser Gly Asn His Phe Ser Gly Ser Ile Pro
                660                 665                 670

Ser Asn Leu Gly Glu Leu Gln Thr Leu Lys Leu Leu Ser Leu Ser Asn
                675                 680                 685

Asn Ser Phe Ser Gly Pro Ile Pro Phe Ser Phe Ser Asn Leu Lys Ser
                690                 695                 700

Leu Glu Phe Leu Asp Leu Ser Leu Asn Asn Leu Ser Gly Thr Ile Pro
705                 710                 715                 720

Lys Ser Phe Glu Lys Leu Leu Tyr Leu Thr Ser Ile Asn Val Ser Phe
                725                 730                 735

Asn Val Leu Glu Gly Glu Ile Pro Ser Gly Gly Val Phe Ala Asn Ser
                740                 745                 750

Thr Leu Gln Ser Phe Ser Gly Asn Lys Gly Leu Cys Gly Arg Gln Ile
                755                 760                 765

Leu Glu Val Pro Ala Cys Ala Ile Thr Thr Pro Glu Gln Gln Gln Ser
770                 775                 780

Lys Ser Lys Lys Leu Val Leu Lys Ile Val Thr Pro Met Val Ile Ser
785                 790                 795                 800

Phe Phe Leu Ile Phe Leu Leu Val Val Ser Ile Trp Ile Met Lys Arg
                805                 810                 815

Lys Lys Lys Gly Lys Ser Lys Asp Val Glu Lys Val Pro Glu Met Arg
                820                 825                 830

Thr Tyr Gln Leu Ile Ser Tyr His Glu Ile Gln Arg Ala Thr Asn Asn
                835                 840                 845

Phe Asp Glu Ser Asn Leu Ile Gly Val Gly Gly Ser Gly Ser Val Tyr
                850                 855                 860

Lys Ala Thr Leu Ala Ser Gly Ile Val Val Ala Ile Lys Val Leu Asp
865                 870                 875                 880

Leu Glu Asn Glu Glu Val Cys Lys Arg Phe Asp Thr Glu Cys Glu Val
                885                 890                 895

Met Arg Asn Val Arg His Lys Asn Leu Val Ser Val Ile Thr Thr Cys
                900                 905                 910

Ser Ser Glu His Ile Arg Ala Phe Val Leu Gln Tyr Met Pro Asn Gly
                915                 920                 925

Ser Leu Asp Asn Trp Leu Tyr Lys Glu Asp Arg His Leu Lys Leu Arg
930                 935                 940

Gln Arg Val Thr Ile Met Leu Asp Val Ala Met Ala Ile Glu Tyr Leu
945                 950                 955                 960

His His Gly Asn Asp Thr Pro Ile Val His Cys Asp Leu Lys Pro Ala
                965                 970                 975

Asn Val Leu Leu Asp Glu Asp Met Val Ala Arg Val Gly Asp Phe Gly
                980                 985                 990

Ile Ser Lys Ile Leu Ala Val Ser Lys Ser Met Ala His Thr Lys Thr
                995                 1000                1005

Leu Gly Thr Leu Gly Tyr Ile Ala Pro Glu Tyr Gly Ser Glu Gly
    1010                1015                1020

Ile Val Ser Thr Arg Gly Asp Val Tyr Ser Tyr Gly Ile Met Leu
    1025                1030                1035
```

```
Met Glu Val Leu Ala Lys Arg Arg Pro Thr Gly Glu Glu Ile Phe
    1040                1045                1050

Asn Glu Asn Leu Gly Leu Arg Glu Trp Ile Thr Arg Ala Phe Pro
    1055                1060                1065

Arg Thr Met Met Glu Val Val Asp Ala Asp Met Phe His Asp Gly
    1070                1075                1080

Glu Lys Ile Thr Ser Glu Ser Glu Ile Cys Ile Leu Ser Met Ile
    1085                1090                1095

Glu Leu Ala Leu Asp Cys Thr Lys Ala Thr Pro Glu Ser Arg Ile
    1100                1105                1110

Thr Met Lys Asp Val Val Lys Arg Leu Asn Lys Ile Lys Asn Thr
    1115                1120                1125

Phe Gly Asn Ile Glu Val Asn
    1130                1135

<210> SEQ ID NO 6
<211> LENGTH: 1169
<212> TYPE: PRT
<213> ORGANISM: Solanum lycopersicum

<400> SEQUENCE: 6

Met Met Met Leu Lys Thr Val Val Tyr Ala Leu Ala Ile Phe Ser Ile
1               5                   10                  15

Thr Phe Leu Ile Pro Leu Ser Ser Gly Gln Asn Pro Arg Phe Glu Val
            20                  25                  30

Glu Val Ala Ala Leu Lys Ala Phe Lys Ser Ser Ile Ser Asp Asp Pro
        35                  40                  45

Phe Ser Ala Leu Val Asp Trp Thr Asp Val Asn His His Cys Asn Trp
    50                  55                  60

Ser Gly Ile Ile Cys Asp Pro Ser Ser Asn His Val Ile Asn Ile Ser
65                  70                  75                  80

Leu Ile Glu Thr Gln Leu Lys Gly Glu Ile Ser Pro Phe Leu Gly Asn
                85                  90                  95

Leu Ser Lys Leu Gln Val Leu Asp Leu Thr Leu Asn Ser Phe Thr Gly
            100                 105                 110

Asn Ile Pro Pro Gln Leu Gly His Cys Thr Asp Leu Val Glu Leu Val
        115                 120                 125

Phe Tyr Gln Asn Ser Leu Phe Gly Glu Ile Pro Ala Glu Leu Gly Asn
    130                 135                 140

Leu Lys Lys Leu Gln Leu Ile Asp Phe Gly Asn Asn Phe Leu Asn Gly
145                 150                 155                 160

Ser Ile Pro Asp Ser Ile Cys Asn Cys Thr Glu Leu Leu Val Gly
                165                 170                 175

Phe Asn Asn Asn Asn Phe Thr Gly Lys Leu Pro Ser Glu Ile Gly Asn
            180                 185                 190

Leu Ala Asn Leu Gln Leu Phe Val Ala Tyr Thr Asn Asn Leu Val Gly
        195                 200                 205

Phe Met Pro Thr Ser Ile Gly Met Leu Thr Ala Leu His Thr Leu Asp
    210                 215                 220

Leu Ser Glu Asn Gln Leu Ser Gly Pro Ile Pro Glu Ile Gly Asn
225                 230                 235                 240

Leu Ser Ser Leu Gly Ile Leu Gln Leu His Leu Asn Ser Leu Ser Gly
                245                 250                 255

Lys Ile Pro Ser Glu Leu Gly Leu Cys Ile Asn Leu Phe Thr Leu Asn
```

```
                260             265             270
Met Tyr Thr Asn Gln Phe Thr Gly Ser Ile Pro Pro Glu Leu Gly Asn
                275                     280             285
Leu Glu Asn Leu Gln Met Leu Arg Leu Tyr Asn Asn Lys Leu Asn Ser
        290                     295             300
Ser Ile Pro Ala Ser Ile Phe His Leu Lys Ser Leu Thr His Leu Gly
305                     310             315                     320
Leu Ser Gln Asn Glu Leu Thr Gly Asn Ile Pro Pro Gln Leu Gly Ser
                325                     330             335
Leu Thr Ser Leu Glu Val Leu Thr Leu His Ser Asn Lys Leu Ser Gly
        340                     345             350
Glu Ile Pro Ser Thr Ile Thr Asn Leu Ala Asn Leu Thr Tyr Leu Ser
            355                 360             365
Leu Gly Phe Asn Leu Leu Thr Gly Ser Leu Pro Ser Glu Phe Gly Leu
            370                 375             380
Leu Tyr Asn Leu Lys Asn Leu Thr Ala Asn Asn Leu Leu Glu Gly
385                     390             395             400
Ser Ile Pro Leu Ser Ile Ile Asn Cys Ser His Leu Leu Val Leu Ser
                405                 410                 415
Leu Thr Phe Asn Arg Ile Thr Gly Glu Ile Pro Asn Gly Leu Gly Gln
                420                 425                 430
Leu Ser Asn Leu Thr Phe Leu Ser Leu Gly Ser Asn Lys Met Met Gly
        435                 440                 445
Glu Ile Pro Asp Asp Leu Phe Asn Ser Ser Met Leu Glu Val Leu Asp
        450                 455                 460
Leu Ser Asp Asn Asn Phe Ser Gly Lys Leu Lys Pro Met Ile Gly Arg
465                 470                 475                 480
Leu Ala Lys Leu Arg Val Leu Arg Ala His Ser Asn Ser Phe Leu Gly
                485                 490                 495
Pro Ile Pro Pro Glu Ile Gly Lys Leu Ser Gln Leu Leu Asp Leu Ala
                500                 505                 510
Leu His Lys Asn Ser Phe Ser Gly Ala Ile Pro Pro Glu Ile Ser Met
        515                 520                 525
Leu Ser Asn Leu Gln Gly Leu Leu Leu Ser Asp Asn Lys Leu Glu Gly
        530                 535                 540
Glu Leu Pro Val Gln Leu Phe Glu Leu Lys Gln Leu Asn Glu Leu Arg
545                 550                 555                 560
Leu Lys Asn Asn Asn Phe Phe Gly Pro Ile Pro His His Ile Ser Lys
                565                 570                 575
Leu Glu Ser Leu Ser Leu Met Asp Leu Ser Gly Asn Lys Leu Asn Gly
            580                 585                 590
Thr Ile Pro Glu Ser Met Thr Ser Leu Arg Arg Leu Met Thr Val Asp
                595                 600                 605
Leu Ser His Asn Leu Leu Thr Gly Thr Leu Pro Arg Ala Val Leu Ala
            610                 615                 620
Ser Met Arg Ser Met Gln Leu Tyr Leu Asn Val Ser Ser Asn Leu Leu
625                 630                 635                 640
His Gly Glu Ile Pro Asp Glu Ile Gly Val Leu Glu Met Val Gln Glu
                645                 650                 655
Ile Asp Met Ser Asn Asn Asn Leu Ser Gly Ser Ile Pro Arg Ser Leu
            660                 665                 670
Glu Arg Cys Lys Asn Leu Phe Ser Leu Asp Leu Ser Gly Asn Met Leu
            675                 680                 685
```

```
Ser Gly Pro Ala Pro Gly Glu Ile Leu Thr Lys Leu Ser Glu Leu Val
    690             695                 700

Phe Leu Asn Leu Ser Arg Asn Arg Leu Glu Gly Ser Leu Pro Glu Ile
705             710                 715                 720

Ala Gly Leu Ser His Leu Ser Ser Leu Asp Val Ser Gln Asn Lys Phe
                725                 730                 735

Lys Gly Ile Ile Pro Glu Arg Phe Ala Asn Met Thr Ala Leu Lys Tyr
            740                 745                 750

Leu Asn Leu Ser Phe Asn Gln Leu Glu Gly His Ile Pro Lys Gly Gly
        755                 760                 765

Val Phe Asn Asn Ile Arg Leu Glu Asp Leu Leu Gly Asn Pro Ser Leu
    770                 775                 780

Cys Gly Lys Lys Phe Leu Ser Pro Cys His Ile Lys Arg Asn Arg Thr
785             790                 795                 800

Ser Ser His Gly Phe Ser Lys Lys Thr Trp Ile Ile Leu Ala Ala Leu
                805                 810                 815

Gly Ser Val Phe Ser Leu Ile Leu Leu Val Leu Gly Ile Phe Leu Phe
                820                 825                 830

His Arg Tyr Met Lys Lys Lys Val Asn Asp Thr Glu Phe Thr Asn
            835                 840                 845

Pro Lys Cys Thr Ala Ala Leu Ser Leu Gln Arg Phe Tyr Gln Lys Asp
    850                 855                 860

Leu Glu His Ala Thr Asn Asn Phe Arg Pro Glu Asn Ile Ile Gly Ala
865             870                 875                 880

Ser Ser Leu Ser Thr Val Tyr Lys Gly Thr Leu Glu Asp Gly Lys Ile
                885                 890                 895

Val Ala Val Lys Lys Leu Asn His Gln Phe Ser Ala Glu Ser Gly Lys
    900                 905                 910

Cys Phe Asp Arg Glu Val Lys Thr Leu Ser Gln Leu Arg His Arg Asn
            915                 920                 925

Leu Val Lys Val Leu Gly Tyr Ala Trp Glu Ser Lys Lys Leu Arg Ala
        930                 935                 940

Leu Val Leu Glu Tyr Met Glu Asn Gly Asn Leu Asp Asn Met Ile Tyr
945             950                 955                 960

Gly Gln Val Glu Asp Asp Trp Thr Leu Ser Asn Arg Ile Asp Ile Leu
                965                 970                 975

Val Ser Val Ala Ser Gly Leu Ser Tyr Leu His Ser Gly Tyr Asp Phe
            980                 985                 990

Pro Ile Val His Cys Asp Met Lys Pro Ser Asn Ile Leu Leu Asp Lys
        995                 1000                1005

Asn Met Glu Ala His Val Ser Asp Phe Gly Thr Ala Arg Met Leu
    1010                1015                1020

Gly Ile His Leu Gln Asp Gly Ser Ser Thr Ser Ser Ala Ser Ala
    1025                1030                1035

Phe Glu Gly Thr Ile Gly Tyr Met Ala Pro Glu Leu Ala Tyr Met
    1040                1045                1050

Arg Lys Val Thr Thr Lys Val Asp Val Phe Ser Phe Gly Val Ile
    1055                1060                1065

Val Met Glu Ile Ile Thr Lys Arg Arg Pro Thr Ser Leu Thr Gly
    1070                1075                1080

Ala Asp Glu Leu Pro Ile Thr Leu His Gln Ile Val Gln Asn Ala
    1085                1090                1095
```

| Leu | Ala | Asn | Gly | Ile | Asn | Lys | Leu | Val | Gln | Ile | Val | Asp | Pro | Asn |
|-----|-----|-----|-----|-----|-----|-----|-----|-----|-----|-----|-----|-----|-----|-----|
| 1100 | | | | | 1105 | | | | | 1110 | | | | |

| Leu | Ala | Ser | Tyr | Val | Ser | Lys | Lys | Gln | Asp | Val | Val | Glu | Gly | Leu |
|-----|-----|-----|-----|-----|-----|-----|-----|-----|-----|-----|-----|-----|-----|-----|
| 1115 | | | | | 1120 | | | | | 1125 | | | | |

| Leu | Asn | Leu | Ala | Leu | Ser | Cys | Thr | Ser | Pro | Asp | Pro | Glu | Asp | Arg |
|-----|-----|-----|-----|-----|-----|-----|-----|-----|-----|-----|-----|-----|-----|-----|
| 1130 | | | | | 1135 | | | | | 1140 | | | | |

| Pro | Asp | Met | Glu | Gln | Val | Leu | Ser | Ser | Leu | Ser | Lys | Leu | Ser | Lys |
|-----|-----|-----|-----|-----|-----|-----|-----|-----|-----|-----|-----|-----|-----|-----|
| 1145 | | | | | 1150 | | | | | 1155 | | | | |

| Met | Asp | Cys | Met | Pro | Ser | His | Leu | Val | Lys | Asp |
|-----|-----|-----|-----|-----|-----|-----|-----|-----|-----|-----|
| 1160 | | | | | 1165 | | | | | |

<210> SEQ ID NO 7
<211> LENGTH: 3402
<212> TYPE: DNA
<213> ORGANISM: Capsicum annum

<400> SEQUENCE: 7

| | |
|---|---|
| atggagaaac acattttctt attgatactt ctcttcctag ttcaagttta cgctgttgcg | 60 |
| tcgatattgg ttacttcctc taatgaaaca gaccaagagg ctctactagc ttttcgaaat | 120 |
| cttattagaa gtgattctag tcattttttg gctaataatt ggaccaagaa tagtacttca | 180 |
| ttttgctctt ggttcggtgt cacttgtagt cccagaaggc aaagggttgt ggccttgaat | 240 |
| cttccggatt tgcaacttcc aggcacaatt tcgccgtcct tggccaattt gtcctttctc | 300 |
| agggagctca atcttggaaa caacagcttc cacggtaaca tcccttatgg cataggcaac | 360 |
| ttgcctcgct tgcgagtgat tgatattcaa acaaccagc tccaaggaag tattccagca | 420 |
| agtctatttc aacaccaaag agttcaaatc atttcattgg ctttcaataa actcagtggt | 480 |
| gaaatgtgga acgtacatg gtatgtaccg gaactcagag tcttaaatct caggaacaat | 540 |
| actctcaccg ggagaatccc tccttctatt ggaaatgcca caaaattgat gaacttcagt | 600 |
| ttgcatggga atagaatcag tggcaatatt ccaaaggaaa ttgtaatct gagccaactt | 660 |
| gcagagctgt tcttgtcgcg taaccagttg acaggttcca ttcccacaac attgtttaat | 720 |
| atctcttccc ttcttgtcgc gtctctggca tttaatagcc tttctggtcc tctcttgctt | 780 |
| ggtgaaggca atattttatc aaatctcgag catctaggta tgtcttacaa tcaaatttct | 840 |
| ggtcgcattc cttccaacat ctgtcaactc aaagagctca agttttgtc catatctttc | 900 |
| aacaacataa ctggggaaat gcccagaaat gttggttgtt taaccaagct cgaggagttg | 960 |
| tatattggtt ataatccaat aaatggtaga attcctacct cattgggcaa tatttccact | 1020 |
| ctgcaaaaac ttcattgtgg aaataatagc atgattgggg aaattcctcc ggaattgggg | 1080 |
| aagctatcaa atttaagaga aatagatttt tcagaaaatt ataatcttac aggtgagatt | 1140 |
| ccaaattcta ttttcaacat atcttcgttg gaatttattg ttttcagttt caactacctc | 1200 |
| tcaggtagga ttccggttct tcttcatttt ccaaacctta caactttt cttggcaaac | 1260 |
| aatcagctcg aagggaaat tcctcggtac ataacaaatg ctacaaagct tgagtcattg | 1320 |
| gacctatcag taaaccgtct cacgggcacc attcctaata atttaggaaa tcttcgcaag | 1380 |
| ctgaaacaac tgttccttca tcataatcaa cttattgagt tgggattctt cgattctttg | 1440 |
| gtgaattgta ggatgttgca atatgtacaa gtgggatcga atccattgaa tggagttttg | 1500 |
| cccagtagta ttggaaatct ttcgtctaat gttgaatact tcatattgg agatgcacaa | 1560 |
| atcagtggat tcattcccac tagtacaggc aacatgagcg tcttacaac cttagttttt | 1620 |
| caagataaca acttgaccgg aaatattcct cgtgagatcg gtaggcttaa acaactccaa | 1680 |

-continued

```
ggtctatttc taattaacaa tgaactacag ggggatatta cggcggtagt atgtgattta      1740
tctaatttgg ttcgattaag tctatctgat aatgagctct ccgggggtgat tccaaattgt     1800 atagggaatc ttagcatgct gcaacaactt tttttgggtt ctaacaattt tggatcagag      1860
cttcctttaa gcatttggaa gatgagaggt ttactctttg taaacatttc gctaaattct      1920
ctagagggag aagttccatc agatatcgga gaacttaaag ccattgtaga gatcgatatt      1980
tctggtaacc acttttcagg gatgatacca agcaatttgg gtgaactcca aaatttgcag      2040
ttactttccc tatcgaacaa ttcatttca ggtccaattc cattatcctt ttcaaacttg       2100
ataagcttgg agatcttgga tttgtcttta ataacttgt caggtactat tcctaagtct       2160
tttgaaaagc tctcatacct tcaaagcatc aatgtttcgt ttaatgcttt agagggtgaa      2220
atacctagtg gtggtgtgtt tgcgaattcc actctgcaat catttcttgg gaacaaaggt      2280
ctttgtggaa ggaacatatc ggaggttcct gcttgtgcta ttactaatcc tgaacaacaa      2340
gcaaaatcta agaagcttgc actgaaaatt gttactctgg tagttatttc attctttctg      2400
atattgttgt tggtcatctc aatttggata agaaacgaa agaagaatgg gaagtccaaa       2460
gatgttgaaa aggttccaga gatgaggact tatcaattga tttcttatca tgagattcaa      2520
cgagcaacaa ataattttga tggatccaat ttaattggcg tgggcggttc tggctctgtg      2580
tacaaaggca cattgccgag cggaattgtg gttgcaataa aggttctgga tttgcatcat     2640
gaggaagtat gcaaaaggtt tgacactgaa tgtgaagtga tgagaaatgt tagacataaa     2700
aatattgttt cggtgatcac tacgtgctca agccaacaca tacgagcctt tgttctgcaa     2760
tatatgccca atggaagtct tgacaattgg ttgtacaaag aagatcgcca cttaaacctt     2820
cttcaaagag ttaccataat gcttgacaca gccatggcaa ttgaatatct acatcatggt     2880
aatgacaccc aaatagttca ttgtgatcta aagccagcca acgttctttt ggatgatgat     2940
atggtggctc atgtaggtga ttttggcatc tctaagattt tagcagtaag caagttcatg    3000
tcacatacaa agacattggg cactcttgga tatattgcac cagaatatgg ctcggaggga    3060
atagtgtcta ctagtggtga tgtttacagt tatggcatca tgttgatgga agttttggca    3120
aaaagaaggc caacagatga agagatatcc aatgaaaatc ttggcttgag ggagtggata    3180
acgcgagcat ttccaagaac tataatggaa gttgtggatg ctgatatttt tcatgatgag    3240
gaaaatatcg cttcgaaaag tgaaatctgc atactttcca tgataaaagt ggctttggat    3300
tgcacaaagg aaatgccgga atctagaatg accatgaatg atgtagtcaa gaggctttac    3360
aaaattaaga acacatttat ggaaacggag aagttagtgt ga                        3402
```

<210> SEQ ID NO 8
<211> LENGTH: 1133
<212> TYPE: PRT
<213> ORGANISM: Capsicum annum

<400> SEQUENCE: 8

Met Glu Lys His Ile Phe Leu Leu Ile Leu Leu Phe Leu Val Gln Val
1               5                   10                  15

Tyr Ala Val Ala Ser Ile Leu Val Thr Ser Ser Asn Glu Thr Asp Gln
            20                  25                  30

Glu Ala Leu Leu Ala Phe Arg Asn Leu Ile Arg Ser Asp Ser Ser His
        35                  40                  45

Phe Leu Ala Asn Asn Trp Thr Lys Asn Ser Thr Ser Phe Cys Ser Trp
    50                  55                  60

Phe Gly Val Thr Cys Ser Pro Arg Arg Gln Arg Val Val Ala Leu Asn

-continued

```
            65                  70                  75                  80
Leu Pro Asp Leu Gln Leu Pro Gly Thr Ile Ser Pro Ser Leu Ala Asn
                85                  90                  95
Leu Ser Phe Leu Arg Glu Leu Asn Leu Gly Asn Asn Ser Phe His Gly
               100                 105                 110
Asn Ile Pro Tyr Gly Ile Gly Asn Leu Pro Arg Leu Arg Val Ile Asp
               115                 120                 125
Ile Gln Asn Asn Gln Leu Gln Gly Ser Ile Pro Ala Ser Leu Phe Gln
               130                 135                 140
His Gln Arg Val Gln Ile Ile Ser Leu Ala Phe Asn Lys Leu Ser Gly
145                 150                 155                 160
Glu Met Trp Asn Gly Thr Trp Tyr Val Pro Glu Leu Arg Val Leu Asn
               165                 170                 175
Leu Arg Asn Asn Thr Leu Thr Gly Arg Ile Pro Pro Ser Ile Gly Asn
               180                 185                 190
Ala Thr Lys Leu Met Asn Phe Ser Leu His Gly Asn Arg Ile Ser Gly
               195                 200                 205
Asn Ile Pro Lys Glu Ile Gly Asn Leu Ser Gln Leu Ala Glu Leu Phe
               210                 215                 220
Leu Ser Arg Asn Gln Leu Thr Gly Ser Ile Pro Thr Thr Leu Phe Asn
225                 230                 235                 240
Ile Ser Ser Leu Leu Val Ala Ser Leu Ala Phe Asn Ser Leu Ser Gly
               245                 250                 255
Pro Leu Leu Gly Glu Gly Asn Ile Leu Ser Asn Leu Glu His Leu
               260                 265                 270
Gly Met Ser Tyr Asn Gln Ile Ser Gly Arg Ile Pro Ser Asn Ile Cys
               275                 280                 285
Gln Leu Lys Glu Leu Lys Val Leu Ser Ile Ser Phe Asn Asn Ile Thr
               290                 295                 300
Gly Glu Met Pro Arg Asn Val Gly Cys Leu Thr Lys Leu Glu Glu Leu
305                 310                 315                 320
Tyr Ile Gly Tyr Asn Pro Ile Asn Gly Arg Ile Pro Thr Ser Leu Gly
               325                 330                 335
Asn Ile Ser Thr Leu Gln Lys Leu His Cys Gly Asn Asn Ser Met Ile
               340                 345                 350
Gly Glu Ile Pro Pro Glu Leu Gly Lys Leu Ser Asn Leu Arg Glu Ile
               355                 360                 365
Asp Phe Ser Glu Asn Tyr Asn Leu Thr Gly Glu Ile Pro Asn Ser Ile
               370                 375                 380
Phe Asn Ile Ser Ser Leu Glu Phe Ile Val Phe Ser Phe Asn Tyr Leu
385                 390                 395                 400
Ser Gly Arg Ile Pro Val Leu Leu His Phe Pro Asn Leu Ile Gln Leu
               405                 410                 415
Phe Leu Ala Asn Asn Gln Leu Glu Gly Glu Ile Pro Arg Tyr Ile Thr
               420                 425                 430
Asn Ala Thr Lys Leu Glu Ser Leu Asp Leu Ser Val Asn Arg Leu Thr
               435                 440                 445
Gly Thr Ile Pro Asn Asn Leu Gly Asn Leu Arg Lys Leu Lys Gln Leu
               450                 455                 460
Phe Leu His His Asn Gln Leu Ile Glu Leu Gly Phe Phe Asp Ser Leu
465                 470                 475                 480
Val Asn Cys Arg Met Leu Gln Tyr Val Gln Val Gly Ser Asn Pro Leu
               485                 490                 495
```

```
Asn Gly Val Leu Pro Ser Ser Ile Gly Asn Leu Ser Ser Asn Val Glu
            500                 505                 510

Tyr Phe His Ile Gly Asp Ala Gln Ile Ser Gly Phe Ile Pro Thr Ser
            515                 520                 525

Thr Gly Asn Met Ser Gly Leu Thr Thr Leu Val Phe Gln Asp Asn Asn
            530                 535                 540

Leu Thr Gly Asn Ile Pro Arg Glu Ile Gly Arg Leu Lys Gln Leu Gln
545                 550                 555                 560

Gly Leu Phe Leu Ile Asn Asn Glu Leu Gln Gly Asp Ile Thr Ala Val
                565                 570                 575

Val Cys Asp Leu Ser Asn Leu Val Arg Leu Ser Leu Ser Asp Asn Glu
            580                 585                 590

Leu Ser Gly Val Ile Pro Asn Cys Ile Gly Asn Leu Ser Met Leu Gln
            595                 600                 605

Gln Leu Phe Leu Gly Ser Asn Asn Phe Gly Ser Glu Leu Pro Leu Ser
            610                 615                 620

Ile Trp Lys Met Arg Gly Leu Leu Phe Val Asn Ile Ser Leu Asn Ser
625                 630                 635                 640

Leu Glu Gly Glu Val Pro Ser Asp Ile Gly Glu Leu Lys Ala Ile Val
                645                 650                 655

Glu Ile Asp Ile Ser Gly Asn His Phe Ser Gly Met Ile Pro Ser Asn
            660                 665                 670

Leu Gly Glu Leu Gln Asn Leu Gln Leu Leu Ser Leu Ser Asn Asn Ser
            675                 680                 685

Phe Ser Gly Pro Ile Pro Leu Ser Phe Ser Asn Leu Ile Ser Leu Glu
            690                 695                 700

Ile Leu Asp Leu Ser Leu Asn Asn Leu Ser Gly Thr Ile Pro Lys Ser
705                 710                 715                 720

Phe Glu Lys Leu Ser Tyr Leu Gln Ser Ile Asn Val Ser Phe Asn Ala
                725                 730                 735

Leu Glu Gly Glu Ile Pro Ser Gly Gly Val Phe Ala Asn Ser Thr Leu
            740                 745                 750

Gln Ser Phe Leu Gly Asn Lys Gly Leu Cys Gly Arg Asn Ile Ser Glu
            755                 760                 765

Val Pro Ala Cys Ala Ile Thr Asn Pro Glu Gln Gln Ala Lys Ser Lys
770                 775                 780

Lys Leu Ala Leu Lys Ile Val Thr Leu Val Val Ile Ser Phe Phe Leu
785                 790                 795                 800

Ile Leu Leu Leu Val Ile Ser Ile Trp Ile Lys Lys Arg Lys Lys Asn
                805                 810                 815

Gly Lys Ser Lys Asp Val Glu Lys Val Pro Glu Met Arg Thr Tyr Gln
            820                 825                 830

Leu Ile Ser Tyr His Glu Ile Gln Arg Ala Thr Asn Asn Phe Asp Gly
            835                 840                 845

Ser Asn Leu Ile Gly Val Gly Gly Ser Gly Val Tyr Lys Gly Thr
            850                 855                 860

Leu Pro Ser Gly Ile Val Val Ala Ile Lys Val Leu Asp Leu His
865                 870                 875                 880

Glu Glu Val Cys Lys Arg Phe Asp Thr Glu Cys Glu Val Met Arg Asn
                885                 890                 895

Val Arg His Lys Asn Ile Val Ser Val Ile Thr Thr Cys Ser Ser Gln
            900                 905                 910
```

His Ile Arg Ala Phe Val Leu Gln Tyr Met Pro Asn Gly Ser Leu Asp
            915                 920                 925

Asn Trp Leu Tyr Lys Glu Asp Arg His Leu Asn Leu Leu Gln Arg Val
        930                 935                 940

Thr Ile Met Leu Asp Thr Ala Met Ala Ile Glu Tyr Leu His His Gly
945                 950                 955                 960

Asn Asp Thr Gln Ile Val His Cys Asp Leu Lys Pro Ala Asn Val Leu
                965                 970                 975

Leu Asp Asp Asp Met Val Ala His Val Gly Asp Phe Gly Ile Ser Lys
            980                 985                 990

Ile Leu Ala Val Ser Lys Phe Met Ser His Thr Lys Thr Leu Gly Thr
        995                 1000                1005

Leu Gly Tyr Ile Ala Pro Glu Tyr Gly Ser Glu Gly Ile Val Ser
    1010                1015                1020

Thr Ser Gly Asp Val Tyr Ser Tyr Gly Ile Met Leu Met Glu Val
    1025                1030                1035

Leu Ala Lys Arg Arg Pro Thr Asp Glu Glu Ile Ser Asn Glu Asn
    1040                1045                1050

Leu Gly Leu Arg Glu Trp Ile Thr Arg Ala Phe Pro Arg Thr Ile
    1055                1060                1065

Met Glu Val Val Asp Ala Asp Ile Phe His Asp Glu Glu Asn Ile
    1070                1075                1080

Ala Ser Lys Ser Glu Ile Cys Ile Leu Ser Met Ile Glu Val Ala
    1085                1090                1095

Leu Asp Cys Thr Lys Glu Met Pro Glu Ser Arg Met Thr Met Asn
    1100                1105                1110

Asp Val Val Lys Arg Leu Tyr Lys Ile Lys Asn Thr Phe Met Glu
    1115                1120                1125

Thr Glu Lys Leu Val
    1130

<210> SEQ ID NO 9
<211> LENGTH: 3410
<212> TYPE: DNA
<213> ORGANISM: Solanum tuberosum

<400> SEQUENCE: 9

```
atggagaaac acattttctt attgatactt gctatcttag ttcaatttta ctttgtttct      60
tctatatcag ctactatttt ctcaaatgag actgatcaag aagctctatt agcttttcga     120
aatcttgtta cgagtgattc tagtcaattt ttagccaata attggaccaa aaatacttca     180
ttttgctctt ggtttggtgt cacttgtagt ccaaaaaggc aaagggttgt agccttgact     240
cttcctaatt tgcaacttca aggcacaatt tcgccttctt tggccaatct atcctttctc     300
atagagctaa atctcacgaa caacaacttc catggtaaca tcccttatgg cattggccac     360
ttgcctcgtt tacgagtgat tgatattcag aacaaccagc tccaaggtag tattccaaca     420
agtctatttc aacaccggag tgttcaaatc atttcattgg ctttcaataa actcggtggt     480
gaaatgtgga acgtacatg gtatgtaccg gaactcagag tcttaaatct caggaacaat     540
accatcacag gtagaatccc tccttctatt ggaaatgcca caagttgat gaacatcagt     600
ttgaattgga atagaatcaa cggcaacatt ccaatggaga tcggtaatct aagccaactt     660
gtagagttgt cgttgtctcg taatcaatta acaggttcca ttccttcaac attgtttaat     720
atctcctccc ttctcgtcgt gtctctggca tacaatagcc tttcaggtcc tctgtttctt     780
```

```
gatgatcgac gtaatgttct ttcatcaaac ctcgagcata taggtgtatc atacaatcaa    840
atcactggtc acatttcttc caacatctgc caattcaaag ctctcaaagt cttgtccata    900
tcatacaaca acataactgg agaaataccg agaaatattg gttgtttagc caagctcgaa    960
gagctttata tcggttataa tgcaatagat ggaacaattc ctacttcatt aggcaatatt   1020
tccactcttc aaaaacttca ttgtggaaac aatcacatgg agggagaact tcctccggaa   1080
ttaggaaagc tatcaaactt aagacaaatc aatttcgaag aaattataa tcttataggt    1140 gaaattccaa atgctatttt caacatatct tctttggaat tcattgcttt cactttcaac   1200
tacctctcag gtagaattcc aaatcttctt catcttccaa accttataca acttctctta   1260
gcaaacaatc agctcgaagg tgaaattcct cggtacatca caaatgctac caatcttgag   1320
ctattggaac tatcagataa ccttctcaca ggcagtattc cttatgattt aggaaatctt   1380
cgcgagctgc aagaactttt cctacatcat aatcaactta ctgagttggg attctttgat   1440
tctttggtga atgtaggat gttgagatat gtacaagtgg gatcgaatcc gttgaatggt    1500
gttctgccaa gtagtattgg caatctttca tctactgttg aatactttca tattggagat   1560
gcacaaatca atggattcat tcccactagt acaggcaaca tgagtggtct acaacgcta    1620 gttcttcaag ataacaattt gacaggaaac attcctcgtg atcggtaa gcttaaacaa     1680 ctccaaggtt tatttctagt taacaatgaa ctgcaggggg atatagcaga ggtagtatgt   1740
gatttatcga atttggttcg attagctctg tctgaaaatg agctctcggg ggtgattccg   1800
gaatgtctag gaagtcttac catgctacaa cacctttttt taggttctaa caagtttgaa   1860
tcaaagcttc ctttaagctt ttggaagatg agtagtcttc tctatgtaaa catgtcgcgt   1920
aattctatag agggagaagt tccatcagat atcggagaac ttaaagctat tgtagcaatt   1980
gaaatctctg gtaaccactt ttcggggatg ataccaagca attttgggga acttcaaaac   2040
ttgaagttac tttccttatc gaacaattcg ttttcaggtc caattccatt atccttttca   2100
aacttgaaaa gcttggaatt cttggatttg tctttgaata acttgtcagg tactattcct   2160
aagtctttcg aaaagctttt gtaccttaca agcatcaacg tctcgtttaa tgttttagaa   2220
ggtgaaatac ctagtggtgg tgtgtttgca aactccaccc tgcaatcatt tcgcgggaac   2280
aaaggtctat gtggaaggca aatattggag gttcctgctt gtgctgtcac tactcctgaa   2340
caacaacaac aaaatcgaa gaggcttgtg ctaaaaattg tcactccggt ggttatttca    2400
ttctttctga tattcttgtt ggttgtctca atttggataa tgaaacgaaa gaagaaagga   2460
aagtccaaag atattgaaaa ggttccggag atgaggactt atcaattgat ttcttatcat   2520
gagattcaac gagcaacaaa caattttgat gaatccaatt tgattggcgt gggaggttct   2580
ggctctgtgt acaaagccac attacctagt ggaattgtgg ttgcaataaa ggtactggat   2640
ttggaaaatg aggaagtatg caaaaggttt gatactgaat gtgaagtggt gagaaatgtt   2700
agacacagaa atcttgtttc ggtgatcact acgtgttcta gtgatcacat aagagccttc   2760
gttctgcaat atatgcccaa cggaagtctt gacaattggt tgtacaaaga agatcgccac   2820
ttaaaccttc gtcaaagagt caccataatg cttgatgtag ctatggcaat tgaatatcta   2880
catcatggta atgacacccc tatagttcat tgtgacctca agccagccaa cgttcttttg   2940
gatgaagata tggtggcgcg tgttggtgat tttggcatct caaagatttt agctgtaagc   3000
aagtctatgg cacatacaaa gacattaggc actcttggat atattgcacc agaatatggc   3060
tcggagggaa tagtgtccac tcgtggtgat gtttacagtt atggcatcat gttgatggag   3120
gttttggcaa aagaaggcc aacaggtgaa gagatattca acgaaaatct tggtttgagg   3180
```

```
gagtggataa cgcgagcatt tccaagaact atgatggaag ttgtggacgc ggatattttt    3240
catgatggag aaaaaatcac ttccaaaagt gaactctgca tactttccat gatagaactg    3300
gctttagatt gcacaaaggc aacaccagaa tcaaggataa ccatgaaaga tgtagtcaag    3360
aggcttaaca aaattaagaa cacattttg gaaacgtaga agttagttag                3410
```

<210> SEQ ID NO 10
<211> LENGTH: 1132
<212> TYPE: PRT
<213> ORGANISM: Solanum tuberosum

<400> SEQUENCE: 10

```
Met Glu Lys His Ile Phe Leu Leu Ile Leu Ala Ile Leu Val Gln Phe
1               5                   10                  15

Tyr Phe Val Ser Ser Ile Ser Ala Thr Ile Phe Ser Asn Glu Thr Asp
            20                  25                  30

Gln Glu Ala Leu Leu Ala Phe Arg Asn Leu Val Thr Ser Asp Ser Ser
        35                  40                  45

Gln Phe Leu Ala Asn Asn Trp Thr Lys Asn Thr Ser Phe Cys Ser Trp
    50                  55                  60

Phe Gly Val Thr Cys Ser Pro Lys Arg Gln Arg Val Val Ala Leu Thr
65                  70                  75                  80

Leu Pro Asn Leu Gln Leu Gln Gly Thr Ile Ser Pro Ser Leu Ala Asn
                85                  90                  95

Leu Ser Phe Leu Ile Glu Leu Asn Leu Thr Asn Asn Asn Phe His Gly
            100                 105                 110

Asn Ile Pro Tyr Gly Ile Gly His Leu Pro Arg Leu Arg Val Ile Asp
        115                 120                 125

Ile Gln Asn Asn Gln Leu Gln Gly Ser Ile Pro Thr Ser Leu Phe Gln
    130                 135                 140

His Arg Ser Val Gln Ile Ile Ser Leu Ala Phe Asn Lys Leu Gly Gly
145                 150                 155                 160

Glu Met Trp Asn Gly Thr Trp Tyr Val Pro Glu Leu Arg Val Leu Asn
                165                 170                 175

Leu Arg Asn Asn Thr Ile Thr Gly Arg Ile Pro Ser Ile Gly Asn
            180                 185                 190

Ala Thr Lys Leu Met Asn Ile Ser Leu Asn Trp Asn Arg Ile Asn Gly
        195                 200                 205

Asn Ile Pro Met Glu Ile Gly Asn Leu Ser Gln Leu Val Glu Leu Ser
    210                 215                 220

Leu Ser Arg Asn Gln Leu Thr Gly Ser Ile Pro Ser Thr Leu Phe Asn
225                 230                 235                 240

Ile Ser Ser Leu Leu Val Val Ser Leu Ala Tyr Asn Ser Leu Ser Gly
                245                 250                 255

Pro Leu Phe Leu Asp Asp Arg Arg Asn Val Leu Ser Ser Asn Leu Glu
            260                 265                 270

His Ile Gly Val Ser Tyr Asn Gln Ile Thr Gly His Ile Ser Ser Asn
        275                 280                 285

Ile Cys Gln Phe Lys Ala Leu Lys Val Leu Ser Ile Ser Tyr Asn Asn
    290                 295                 300

Ile Thr Gly Glu Ile Pro Arg Asn Ile Gly Cys Leu Ala Lys Leu Glu
305                 310                 315                 320

Glu Leu Tyr Ile Gly Tyr Asn Ala Ile Asp Gly Thr Ile Pro Thr Ser
                325                 330                 335
```

```
Leu Gly Asn Ile Ser Thr Leu Gln Lys Leu His Cys Gly Asn Asn His
            340                 345                 350

Met Glu Gly Glu Leu Pro Pro Glu Leu Gly Lys Leu Ser Asn Leu Arg
            355                 360                 365

Gln Ile Asn Phe Glu Glu Asn Tyr Asn Leu Ile Gly Glu Ile Pro Asn
370                 375                 380

Ala Ile Phe Asn Ile Ser Ser Leu Glu Phe Ile Ala Phe Thr Phe Asn
385                 390                 395                 400

Tyr Leu Ser Gly Arg Ile Pro Asn Leu Leu His Leu Pro Asn Leu Ile
            405                 410                 415

Gln Leu Leu Ala Asn Asn Gln Leu Glu Gly Glu Ile Pro Arg Tyr
            420                 425                 430

Ile Thr Asn Ala Thr Asn Leu Glu Leu Leu Glu Leu Ser Asp Asn Leu
            435                 440                 445

Leu Thr Gly Ser Ile Pro Tyr Asp Leu Gly Asn Leu Arg Glu Leu Gln
            450                 455                 460

Glu Leu Phe Leu His His Asn Gln Leu Thr Glu Leu Gly Phe Phe Asp
465                 470                 475                 480

Ser Leu Val Lys Cys Arg Met Leu Arg Tyr Val Gln Val Gly Ser Asn
            485                 490                 495

Pro Leu Asn Gly Val Leu Pro Ser Ser Ile Gly Asn Leu Ser Ser Thr
            500                 505                 510

Val Glu Tyr Phe His Ile Gly Asp Ala Gln Ile Asn Gly Phe Ile Pro
            515                 520                 525

Thr Ser Thr Gly Asn Met Ser Gly Leu Thr Thr Leu Val Leu Gln Asp
            530                 535                 540

Asn Asn Leu Thr Gly Asn Ile Pro Arg Glu Ile Gly Lys Leu Lys Gln
545                 550                 555                 560

Leu Gln Gly Leu Phe Leu Val Asn Asn Glu Leu Gln Gly Asp Ile Ala
            565                 570                 575

Glu Val Val Cys Asp Leu Ser Asn Leu Val Arg Leu Ala Leu Ser Glu
            580                 585                 590

Asn Glu Leu Ser Gly Val Ile Pro Glu Cys Leu Gly Ser Leu Thr Met
            595                 600                 605

Leu Gln His Leu Phe Leu Gly Ser Asn Lys Phe Glu Ser Lys Leu Pro
            610                 615                 620

Leu Ser Phe Trp Lys Met Ser Ser Leu Leu Tyr Val Asn Met Ser Arg
625                 630                 635                 640

Asn Ser Ile Glu Gly Glu Val Pro Ser Asp Ile Gly Glu Leu Lys Ala
            645                 650                 655

Ile Val Ala Ile Glu Ile Ser Gly Asn His Phe Ser Gly Met Ile Pro
            660                 665                 670

Ser Asn Leu Gly Glu Leu Gln Asn Leu Lys Leu Leu Ser Leu Ser Asn
            675                 680                 685

Asn Ser Phe Ser Gly Pro Ile Pro Leu Ser Phe Ser Asn Leu Lys Ser
            690                 695                 700

Leu Glu Phe Leu Asp Leu Ser Leu Asn Asn Leu Ser Gly Thr Ile Pro
705                 710                 715                 720

Lys Ser Phe Glu Lys Leu Leu Tyr Leu Thr Ser Ile Asn Val Ser Phe
            725                 730                 735

Asn Val Leu Glu Gly Glu Ile Pro Ser Gly Gly Val Phe Ala Asn Ser
            740                 745                 750
```

Thr Leu Gln Ser Phe Arg Gly Asn Lys Gly Leu Cys Gly Arg Gln Ile
        755                 760                 765

Leu Glu Val Pro Ala Cys Ala Val Thr Thr Pro Glu Gln Gln Gln Pro
770                 775                 780

Lys Ser Lys Arg Leu Val Leu Lys Ile Val Thr Pro Val Val Ile Ser
785                 790                 795                 800

Phe Phe Leu Ile Phe Leu Leu Val Val Ser Ile Trp Ile Met Lys Arg
            805                 810                 815

Lys Lys Lys Gly Lys Ser Lys Asp Ile Glu Lys Val Pro Glu Met Arg
            820                 825                 830

Thr Tyr Gln Leu Ile Ser Tyr His Glu Ile Gln Arg Ala Thr Asn Asn
        835                 840                 845

Phe Asp Glu Ser Asn Leu Ile Gly Val Gly Gly Ser Gly Ser Val Tyr
850                 855                 860

Lys Ala Thr Leu Pro Ser Gly Ile Val Val Ala Ile Lys Val Leu Asp
865                 870                 875                 880

Leu Glu Asn Glu Glu Val Cys Lys Arg Phe Asp Thr Glu Cys Glu Val
            885                 890                 895

Val Arg Asn Val Arg His Arg Asn Leu Val Ser Val Ile Thr Thr Cys
        900                 905                 910

Ser Ser Asp His Ile Arg Ala Phe Val Leu Gln Tyr Met Pro Asn Gly
        915                 920                 925

Ser Leu Asp Asn Trp Leu Tyr Lys Glu Asp Arg His Leu Asn Leu Arg
        930                 935                 940

Gln Arg Val Thr Ile Met Leu Asp Val Ala Met Ala Ile Glu Tyr Leu
945                 950                 955                 960

His His Gly Asn Asp Thr Pro Ile Val His Cys Asp Leu Lys Pro Ala
            965                 970                 975

Asn Val Leu Leu Asp Glu Asp Met Val Ala Arg Val Gly Asp Phe Gly
            980                 985                 990

Ile Ser Lys Ile Leu Ala Val Ser Lys Ser Met Ala His Thr Lys Thr
            995                 1000                1005

Leu Gly Thr Leu Gly Tyr Ile Ala Pro Glu Tyr Gly Ser Glu Gly
    1010                1015                1020

Ile Val Ser Thr Arg Gly Asp Val Tyr Ser Tyr Gly Ile Met Leu
    1025                1030                1035

Met Glu Val Leu Ala Lys Arg Arg Pro Thr Gly Glu Glu Ile Phe
    1040                1045                1050

Asn Glu Asn Leu Gly Leu Arg Glu Trp Ile Thr Arg Ala Phe Pro
    1055                1060                1065

Arg Thr Met Met Glu Val Val Asp Ala Asp Ile Phe His Asp Gly
    1070                1075                1080

Glu Lys Ile Thr Ser Lys Ser Glu Leu Cys Ile Leu Ser Met Ile
    1085                1090                1095

Glu Leu Ala Leu Asp Cys Thr Lys Ala Thr Pro Glu Ser Arg Ile
    1100                1105                1110

Thr Met Lys Asp Val Val Lys Arg Leu Asn Lys Ile Lys Asn Thr
    1115                1120                1125

Phe Leu Glu Thr
    1130

<210> SEQ ID NO 11
<211> LENGTH: 1138
<212> TYPE: PRT

-continued

```
<213> ORGANISM: Artificial
<220> FEATURE:
<223> OTHER INFORMATION: Conserved protein sequence for FLS3
<220> FEATURE:
<221> NAME/KEY: MISC_FEATURE
<222> LOCATION: (11)..(11)
<223> OTHER INFORMATION: Xaa at position 11 is Ala or Leu
<220> FEATURE:
<221> NAME/KEY: MISC_FEATURE
<222> LOCATION: (12)..(12)
<223> OTHER INFORMATION: Xaa at position 12 is Ile or Phe
<220> FEATURE:
<221> NAME/KEY: MISC_FEATURE
<222> LOCATION: (16)..(16)
<223> OTHER INFORMATION: Xaa at position 16 is Phe or Val
<220> FEATURE:
<221> NAME/KEY: MISC_FEATURE
<222> LOCATION: (18)..(18)
<223> OTHER INFORMATION: Xaa at position 18 is Phe or Ala
<220> FEATURE:
<221> NAME/KEY: MISC_FEATURE
<222> LOCATION: (23)..(23)
<223> OTHER INFORMATION: Xaa at position 23 is Ser or Leu
<220> FEATURE:
<221> NAME/KEY: MISC_FEATURE
<222> LOCATION: (24)..(24)
<223> OTHER INFORMATION: Xaa at position 24 is Ala or Val
<220> FEATURE:
<221> NAME/KEY: MISC_FEATURE
<222> LOCATION: (25)..(25)
<223> OTHER INFORMATION: Xaa at position 25 is Thr or absent
<220> FEATURE:
<221> NAME/KEY: MISC_FEATURE
<222> LOCATION: (26)..(26)
<223> OTHER INFORMATION: Xaa at position 26 is Ile or Thr
<220> FEATURE:
<221> NAME/KEY: MISC_FEATURE
<222> LOCATION: (27)..(27)
<223> OTHER INFORMATION: Xaa at position 27 is Ser or Phe
<220> FEATURE:
<221> NAME/KEY: MISC_FEATURE
<222> LOCATION: (43)..(43)
<223> OTHER INFORMATION: Xaa at position 43 is Val or Ile
<220> FEATURE:
<221> NAME/KEY: MISC_FEATURE
<222> LOCATION: (44)..(44)
<223> OTHER INFORMATION: Xaa at position 44 is Arg or Thr
<220> FEATURE:
<221> NAME/KEY: MISC_FEATURE
<222> LOCATION: (49)..(49)
<223> OTHER INFORMATION: Xaa at position 49 is His or Gln
<220> FEATURE:
<221> NAME/KEY: MISC_FEATURE
<222> LOCATION: (59)..(59)
<223> OTHER INFORMATION: Xaa at position 59 is Ser or absent
<220> FEATURE:
<221> NAME/KEY: MISC_FEATURE
<222> LOCATION: (73)..(73)
<223> OTHER INFORMATION: Xaa at position 73 is Lys or Arg
<220> FEATURE:
<221> NAME/KEY: MISC_FEATURE
<222> LOCATION: (81)..(81)
<223> OTHER INFORMATION: Xaa at position 81 is Thr or Asn
<220> FEATURE:
<221> NAME/KEY: MISC_FEATURE
<222> LOCATION: (84)..(84)
<223> OTHER INFORMATION: Xaa at position 84 is Asn or Asp
<220> FEATURE:
<221> NAME/KEY: MISC_FEATURE
<222> LOCATION: (88)..(88)
<223> OTHER INFORMATION: Xaa at position 88 is Gln or Pro
<220> FEATURE:
<221> NAME/KEY: MISC_FEATURE
<222> LOCATION: (102)..(102)
<223> OTHER INFORMATION: Xaa at position 102 is Ile or Arg
<220> FEATURE:
<221> NAME/KEY: MISC_FEATURE
<222> LOCATION: (103)..(103)
<223> OTHER INFORMATION: Xaa at position 103 is Glu or Gly
```

```
<220> FEATURE:
<221> NAME/KEY: MISC_FEATURE
<222> LOCATION: (107)..(107)
<223> OTHER INFORMATION: Xaa at position 107 is Ala, Gly, or Thr
<220> FEATURE:
<221> NAME/KEY: MISC_FEATURE
<222> LOCATION: (110)..(110)
<223> OTHER INFORMATION: Xaa at position 110 is Asn or Ser
<220> FEATURE:
<221> NAME/KEY: MISC_FEATURE
<222> LOCATION: (111)..(111)
<223> OTHER INFORMATION: Xaa at position 111 is Leu or Phe
<220> FEATURE:
<221> NAME/KEY: MISC_FEATURE
<222> LOCATION: (113)..(113)
<223> OTHER INFORMATION: Xaa at position 113 is Ser or Gly
<220> FEATURE:
<221> NAME/KEY: MISC_FEATURE
<222> LOCATION: (114)..(114)
<223> OTHER INFORMATION: Xaa at position 114 is Glu or Asn
<220> FEATURE:
<221> NAME/KEY: MISC_FEATURE
<222> LOCATION: (117)..(117)
<223> OTHER INFORMATION: Xaa at position 117 is Asp or Tyr
<220> FEATURE:
<221> NAME/KEY: MISC_FEATURE
<222> LOCATION: (121)..(121)
<223> OTHER INFORMATION: Xaa at position 121 is Arg, Asn, or His
<220> FEATURE:
<221> NAME/KEY: MISC_FEATURE
<222> LOCATION: (137)..(137)
<223> OTHER INFORMATION: Xaa at position 137 is His or Gln
<220> FEATURE:
<221> NAME/KEY: MISC_FEATURE
<222> LOCATION: (142)..(142)
<223> OTHER INFORMATION: Xaa at position 142 is Thr or Ala
<220> FEATURE:
<221> NAME/KEY: MISC_FEATURE
<222> LOCATION: (148)..(148)
<223> OTHER INFORMATION: Xaa at position 148 is Gly, Gln, or Arg
<220> FEATURE:
<221> NAME/KEY: MISC_FEATURE
<222> LOCATION: (149)..(149)
<223> OTHER INFORMATION: Xaa at position 149 is Ser or Arg
<220> FEATURE:
<221> NAME/KEY: MISC_FEATURE
<222> LOCATION: (161)..(161)
<223> OTHER INFORMATION: Xaa at position 161 is Gly or Ser
<220> FEATURE:
<221> NAME/KEY: MISC_FEATURE
<222> LOCATION: (184)..(184)
<223> OTHER INFORMATION: Xaa at position 184 is Ile or Leu
<220> FEATURE:
<221> NAME/KEY: MISC_FEATURE
<222> LOCATION: (187)..(187)
<223> OTHER INFORMATION: Xaa at position 187 is Val or Arg
<220> FEATURE:
<221> NAME/KEY: MISC_FEATURE
<222> LOCATION: (201)..(201)
<223> OTHER INFORMATION: Xaa at position 201 is Phe or Ile
<220> FEATURE:
<221> NAME/KEY: MISC_FEATURE
<222> LOCATION: (204)..(204)
<223> OTHER INFORMATION: Xaa at position 204 is Asn or His
<220> FEATURE:
<221> NAME/KEY: MISC_FEATURE
<222> LOCATION: (205)..(205)
<223> OTHER INFORMATION: Xaa at position 205 is Gly or Trp
<220> FEATURE:
<221> NAME/KEY: MISC_FEATURE
<222> LOCATION: (209)..(209)
<223> OTHER INFORMATION: Xaa at position 209 is Asn or Ser
<220> FEATURE:
<221> NAME/KEY: MISC_FEATURE
<222> LOCATION: (214)..(214)
<223> OTHER INFORMATION: Xaa at position 214 is Met or Lys
<220> FEATURE:
<221> NAME/KEY: MISC_FEATURE
<222> LOCATION: (223)..(223)
```

```
<223> OTHER INFORMATION: Xaa at position 223 is Val or Ala
<220> FEATURE:
<221> NAME/KEY: MISC_FEATURE
<222> LOCATION: (226)..(226)
<223> OTHER INFORMATION: Xaa at position 226 is Ser or Phe
<220> FEATURE:
<221> NAME/KEY: MISC_FEATURE
<222> LOCATION: (238)..(238)
<223> OTHER INFORMATION: Xaa at position 238 is Ser or Thr
<220> FEATURE:
<221> NAME/KEY: MISC_FEATURE
<222> LOCATION: (249)..(249)
<223> OTHER INFORMATION: Xaa at position 249 is Val or Ala
<220> FEATURE:
<221> NAME/KEY: MISC_FEATURE
<222> LOCATION: (253)..(253)
<223> OTHER INFORMATION: Xaa at position 253 is Tyr or Phe
<220> FEATURE:
<221> NAME/KEY: MISC_FEATURE
<222> LOCATION: (261)..(261)
<223> OTHER INFORMATION: Xaa at position 261 is Phe or Leu
<220> FEATURE:
<221> NAME/KEY: MISC_FEATURE
<222> LOCATION: (262)..(262)
<223> OTHER INFORMATION: Xaa at position 262 is Pro or Leu
<220> FEATURE:
<221> NAME/KEY: MISC_FEATURE
<222> LOCATION: (263)..(263)
<223> OTHER INFORMATION: Xaa at position 263 is Asp or Gly
<220> FEATURE:
<221> NAME/KEY: MISC_FEATURE
<222> LOCATION: (264)..(264)
<223> OTHER INFORMATION: Xaa at position 264 is Asp or Glu
<220> FEATURE:
<221> NAME/KEY: MISC_FEATURE
<222> LOCATION: (265)..(265)
<223> OTHER INFORMATION: Xaa at position 265 is Arg or Gly
<220> FEATURE:
<221> NAME/KEY: MISC_FEATURE
<222> LOCATION: (266)..(266)
<223> OTHER INFORMATION: Xaa at position 266 is Arg or absent
<220> FEATURE:
<221> NAME/KEY: MISC_FEATURE
<222> LOCATION: (267)..(267)
<223> OTHER INFORMATION: Xaa at position 267 is Asn or absent
<220> FEATURE:
<221> NAME/KEY: MISC_FEATURE
<222> LOCATION: (268)..(268)
<223> OTHER INFORMATION: Xaa at position 268 is Val or Asn
<220> FEATURE:
<221> NAME/KEY: MISC_FEATURE
<222> LOCATION: (269)..(269)
<223> OTHER INFORMATION: Xaa at position 269 is Leu or Ile
<220> FEATURE:
<221> NAME/KEY: MISC_FEATURE
<222> LOCATION: (270)..(270)
<223> OTHER INFORMATION: Xaa at position 270 is Ser or Leu
<220> FEATURE:
<221> NAME/KEY: MISC_FEATURE
<222> LOCATION: (276)..(276)
<223> OTHER INFORMATION: Xaa at position 276 is Ile or Leu
<220> FEATURE:
<221> NAME/KEY: MISC_FEATURE
<222> LOCATION: (278)..(278)
<223> OTHER INFORMATION: Xaa at position 278 is Val or Met
<220> FEATURE:
<221> NAME/KEY: MISC_FEATURE
<222> LOCATION: (284)..(284)
<223> OTHER INFORMATION: Xaa at position 284 is Thr or Ser
<220> FEATURE:
<221> NAME/KEY: MISC_FEATURE
<222> LOCATION: (286)..(286)
<223> OTHER INFORMATION: Xaa at position 286 is His or Arg
<220> FEATURE:
<221> NAME/KEY: MISC_FEATURE
<222> LOCATION: (288)..(288)
<223> OTHER INFORMATION: Xaa at position 288 is Pro or Ser
<220> FEATURE:
<221> NAME/KEY: MISC_FEATURE
```

```
<222> LOCATION: (294)..(294)
<223> OTHER INFORMATION: Xaa at position 294 is Phe or Leu
<220> FEATURE:
<221> NAME/KEY: MISC_FEATURE
<222> LOCATION: (295)..(295)
<223> OTHER INFORMATION: Xaa at position 295 is Thr or Lys
<220> FEATURE:
<221> NAME/KEY: MISC_FEATURE
<222> LOCATION: (296)..(296)
<223> OTHER INFORMATION: Xaa at position 296 is Ala or Glu
<220> FEATURE:
<221> NAME/KEY: MISC_FEATURE
<222> LOCATION: (298)..(298)
<223> OTHER INFORMATION: Xaa at position 298 is Arg or Lys
<220> FEATURE:
<221> NAME/KEY: MISC_FEATURE
<222> LOCATION: (304)..(304)
<223> OTHER INFORMATION: Xaa at position 304 is Tyr or Phe
<220> FEATURE:
<221> NAME/KEY: MISC_FEATURE
<222> LOCATION: (311)..(311)
<223> OTHER INFORMATION: Xaa at position 311 is Ile or Met
<220> FEATURE:
<221> NAME/KEY: MISC_FEATURE
<222> LOCATION: (315)..(315)
<223> OTHER INFORMATION: Xaa at position 315 is Ile or Val
<220> FEATURE:
<221> NAME/KEY: MISC_FEATURE
<222> LOCATION: (319)..(319)
<223> OTHER INFORMATION: Xaa at position 319 is Ala or Thr
<220> FEATURE:
<221> NAME/KEY: MISC_FEATURE
<222> LOCATION: (324)..(324)
<223> OTHER INFORMATION: Xaa at position 324 is Phe or Leu
<220> FEATURE:
<221> NAME/KEY: MISC_FEATURE
<222> LOCATION: (330)..(330)
<223> OTHER INFORMATION: Xaa at position 330 is Ala or Pro
<220> FEATURE:
<221> NAME/KEY: MISC_FEATURE
<222> LOCATION: (332)..(332)
<223> OTHER INFORMATION: Xaa at position 332 is Asn or Asp
<220> FEATURE:
<221> NAME/KEY: MISC_FEATURE
<222> LOCATION: (334)..(334)
<223> OTHER INFORMATION: Xaa at position 334 is Thr or Arg
<220> FEATURE:
<221> NAME/KEY: MISC_FEATURE
<222> LOCATION: (337)..(337)
<223> OTHER INFORMATION: Xaa at position 337 is Ala or Thr
<220> FEATURE:
<221> NAME/KEY: MISC_FEATURE
<222> LOCATION: (347)..(347)
<223> OTHER INFORMATION: Xaa at position 347 is Asn or Lys
<220> FEATURE:
<221> NAME/KEY: MISC_FEATURE
<222> LOCATION: (352)..(352)
<223> OTHER INFORMATION: Xaa at position 352 is Ser of Asn
<220> FEATURE:
<221> NAME/KEY: MISC_FEATURE
<222> LOCATION: (354)..(354)
<223> OTHER INFORMATION: Xaa at position 354 is His or Ser
<220> FEATURE:
<221> NAME/KEY: MISC_FEATURE
<222> LOCATION: (356)..(356)
<223> OTHER INFORMATION: Xaa at position 356 is Glu or Ile
<220> FEATURE:
<221> NAME/KEY: MISC_FEATURE
<222> LOCATION: (359)..(359)
<223> OTHER INFORMATION: Xaa at position 359 is Leu or Ile
<220> FEATURE:
<221> NAME/KEY: MISC_FEATURE
<222> LOCATION: (371)..(371)
<223> OTHER INFORMATION: Xaa at position 371 is Gln or Glu
<220> FEATURE:
<221> NAME/KEY: MISC_FEATURE
<222> LOCATION: (373)..(373)
<223> OTHER INFORMATION: Xaa at position 373 is Asn or Asp
<220> FEATURE:
```

```
<221> NAME/KEY: MISC_FEATURE
<222> LOCATION: (375)..(375)
<223> OTHER INFORMATION: Xaa at position 375 is Glu or Ser
<220> FEATURE:
<221> NAME/KEY: MISC_FEATURE
<222> LOCATION: (381)..(381)
<223> OTHER INFORMATION: Xaa at position 381 is Ile or Thr
<220> FEATURE:
<221> NAME/KEY: MISC_FEATURE
<222> LOCATION: (387)..(387)
<223> OTHER INFORMATION: Xaa at position 387 is Thr, Ser, or Ala
<220> FEATURE:
<221> NAME/KEY: MISC_FEATURE
<222> LOCATION: (398)..(398)
<223> OTHER INFORMATION: Xaa at position 398 is Ala or Val
<220> FEATURE:
<221> NAME/KEY: MISC_FEATURE
<222> LOCATION: (400)..(400)
<223> OTHER INFORMATION: Xaa at position 400 is Thr or Ser
<220> FEATURE:
<221> NAME/KEY: MISC_FEATURE
<222> LOCATION: (410)..(410)
<223> OTHER INFORMATION: Xaa at position 410 is Asn or Val
<220> FEATURE:
<221> NAME/KEY: MISC_FEATURE
<222> LOCATION: (414)..(414)
<223> OTHER INFORMATION: Xaa at position 414 is Leu or Phe
<220> FEATURE:
<221> NAME/KEY: MISC_FEATURE
<222> LOCATION: (421)..(421)
<223> OTHER INFORMATION: Xaa at position 421 is Leu or Phe
<220> FEATURE:
<221> NAME/KEY: MISC_FEATURE
<222> LOCATION: (440)..(440)
<223> OTHER INFORMATION: Xaa at position 440 is Asn or Lys
<220> FEATURE:
<221> NAME/KEY: MISC_FEATURE
<222> LOCATION: (443)..(443)
<223> OTHER INFORMATION: Xaa at position 443 is Leu or Ser
<220> FEATURE:
<221> NAME/KEY: MISC_FEATURE
<222> LOCATION: (445)..(445)
<223> OTHER INFORMATION: Xaa at position 445 is Glu or Asp
<220> FEATURE:
<221> NAME/KEY: MISC_FEATURE
<222> LOCATION: (448)..(448)
<223> OTHER INFORMATION: Xaa at position 448 is Asp or Val
<220> FEATURE:
<221> NAME/KEY: MISC_FEATURE
<222> LOCATION: (450)..(450)
<223> OTHER INFORMATION: Xaa at position 450 is Leu or Arg
<220> FEATURE:
<221> NAME/KEY: MISC_FEATURE
<222> LOCATION: (454)..(454)
<223> OTHER INFORMATION: Xaa at position 454 is Thr or Ser
<220> FEATURE:
<221> NAME/KEY: MISC_FEATURE
<222> LOCATION: (457)..(457)
<223> OTHER INFORMATION: Xaa at position 457 is Asn or Tyr
<220> FEATURE:
<221> NAME/KEY: MISC_FEATURE
<222> LOCATION: (458)..(458)
<223> OTHER INFORMATION: Xaa at position 458 is Asp or Asn
<220> FEATURE:
<221> NAME/KEY: MISC_FEATURE
<222> LOCATION: (464)..(464)
<223> OTHER INFORMATION: Xaa at position 464 is Glu or Lys
<220> FEATURE:
<221> NAME/KEY: MISC_FEATURE
<222> LOCATION: (466)..(466)
<223> OTHER INFORMATION: Xaa at position 466 is Arg, Lys, or Gln
<220> FEATURE:
<221> NAME/KEY: MISC_FEATURE
<222> LOCATION: (467)..(467)
<223> OTHER INFORMATION: Xaa at position 467 is Asp, Gln, or Glu
<220> FEATURE:
<221> NAME/KEY: MISC_FEATURE
<222> LOCATION: (476)..(476)
<223> OTHER INFORMATION: Xaa at position 476 is Thr or Ile
```

-continued

```
<220> FEATURE:
<221> NAME/KEY: MISC_FEATURE
<222> LOCATION: (486)..(486)
<223> OTHER INFORMATION: Xaa at position 486 is Lys or Asn
<220> FEATURE:
<221> NAME/KEY: MISC_FEATURE
<222> LOCATION: (491)..(491)
<223> OTHER INFORMATION: Xaa at position 491 is Arg or Gln
<220> FEATURE:
<221> NAME/KEY: MISC_FEATURE
<222> LOCATION: (502)..(502)
<223> OTHER INFORMATION: Xaa at position 502 is Asp or Gly
<220> FEATURE:
<221> NAME/KEY: MISC_FEATURE
<222> LOCATION: (514)..(514)
<223> OTHER INFORMATION: Xaa at position 514 is Thr or Asn
<220> FEATURE:
<221> NAME/KEY: MISC_FEATURE
<222> LOCATION: (526)..(526)
<223> OTHER INFORMATION: Xaa at position 526 is Asn or Ser
<220> FEATURE:
<221> NAME/KEY: MISC_FEATURE
<222> LOCATION: (537)..(537)
<223> OTHER INFORMATION: Xaa at position 537 is Thr or Ser
<220> FEATURE:
<221> NAME/KEY: MISC_FEATURE
<222> LOCATION: (544)..(544)
<223> OTHER INFORMATION: Xaa at position 544 is Phe or Leu
<220> FEATURE:
<221> NAME/KEY: MISC_FEATURE
<222> LOCATION: (548)..(548)
<223> OTHER INFORMATION: Xaa at position 548 is Ser or Asn
<220> FEATURE:
<221> NAME/KEY: MISC_FEATURE
<222> LOCATION: (558)..(558)
<223> OTHER INFORMATION: Xaa at position 558 is Arg or Gly
<220> FEATURE:
<221> NAME/KEY: MISC_FEATURE
<222> LOCATION: (559)..(559)
<223> OTHER INFORMATION: Xaa at position 559 is Lys or Arg
<220> FEATURE:
<221> NAME/KEY: MISC_FEATURE
<222> LOCATION: (569)..(569)
<223> OTHER INFORMATION: Xaa at position 569 is Val or Ile
<220> FEATURE:
<221> NAME/KEY: MISC_FEATURE
<222> LOCATION: (572)..(572)
<223> OTHER INFORMATION: Xaa at position 572 is Gly or Glu
<220> FEATURE:
<221> NAME/KEY: MISC_FEATURE
<222> LOCATION: (578)..(578)
<223> OTHER INFORMATION: Xaa at position 578 is Ala or Thr
<220> FEATURE:
<221> NAME/KEY: MISC_FEATURE
<222> LOCATION: (579)..(579)
<223> OTHER INFORMATION: Xaa at position 579 is Glu or Ala
<220> FEATURE:
<221> NAME/KEY: MISC_FEATURE
<222> LOCATION: (591)..(591)
<223> OTHER INFORMATION: Xaa at position 591 is Ala or Ser
<220> FEATURE:
<221> NAME/KEY: MISC_FEATURE
<222> LOCATION: (594)..(594)
<223> OTHER INFORMATION: Xaa at position 594 is Glu or Asp
<220> FEATURE:
<221> NAME/KEY: MISC_FEATURE
<222> LOCATION: (603)..(603)
<223> OTHER INFORMATION: Xaa at position 603 is Glu or Asn
<220> FEATURE:
<221> NAME/KEY: MISC_FEATURE
<222> LOCATION: (605)..(605)
<223> OTHER INFORMATION: Xaa at position 605 is Leu or Ile
<220> FEATURE:
<221> NAME/KEY: MISC_FEATURE
<222> LOCATION: (607)..(607)
<223> OTHER INFORMATION: Xaa at position 607 is Asn or Ser
<220> FEATURE:
<221> NAME/KEY: MISC_FEATURE
<222> LOCATION: (609)..(609)
```

```
<223> OTHER INFORMATION: Xaa at position 609 is Thr or Ser
<220> FEATURE:
<221> NAME/KEY: MISC_FEATURE
<222> LOCATION: (613)..(613)
<223> OTHER INFORMATION: Xaa at position 613 is Gln or His
<220> FEATURE:
<221> NAME/KEY: MISC_FEATURE
<222> LOCATION: (620)..(620)
<223> OTHER INFORMATION: Xaa at position 620 is Lys or Asn
<220> FEATURE:
<221> NAME/KEY: MISC_FEATURE
<222> LOCATION: (622)..(622)
<223> OTHER INFORMATION: Xaa at position 622 is Glu or Gly
<220> FEATURE:
<221> NAME/KEY: MISC_FEATURE
<222> LOCATION: (624)..(624)
<223> OTHER INFORMATION: Xaa at position 624 is Lys or Glu
<220> FEATURE:
<221> NAME/KEY: MISC_FEATURE
<222> LOCATION: (629)..(629)
<223> OTHER INFORMATION: Xaa at position 629 is Phe or Ile
<220> FEATURE:
<221> NAME/KEY: MISC_FEATURE
<222> LOCATION: (633)..(633)
<223> OTHER INFORMATION: Xaa at position 633 is Ser or Arg
<220> FEATURE:
<221> NAME/KEY: MISC_FEATURE
<222> LOCATION: (634)..(634)
<223> OTHER INFORMATION: Xaa at position 634 is Ser or Gly
<220> FEATURE:
<221> NAME/KEY: MISC_FEATURE
<222> LOCATION: (637)..(637)
<223> OTHER INFORMATION: Xaa at position 637 is Tyr or Phe
<220> FEATURE:
<221> NAME/KEY: MISC_FEATURE
<222> LOCATION: (638)..(638)
<223> OTHER INFORMATION: Xaa at position 638 is Leu or Val
<220> FEATURE:
<221> NAME/KEY: MISC_FEATURE
<222> LOCATION: (640)..(640)
<223> OTHER INFORMATION: Xaa at position 640 is Met or Ile
<220> FEATURE:
<221> NAME/KEY: MISC_FEATURE
<222> LOCATION: (642)..(642)
<223> OTHER INFORMATION: Xaa at position 642 is Arg or Leu
<220> FEATURE:
<221> NAME/KEY: MISC_FEATURE
<222> LOCATION: (645)..(645)
<223> OTHER INFORMATION: Xaa at position 645 is Ile or Leu
<220> FEATURE:
<221> NAME/KEY: MISC_FEATURE
<222> LOCATION: (646)..(646)
<223> OTHER INFORMATION: Xaa at position 646 is Lys or Glu
<220> FEATURE:
<221> NAME/KEY: MISC_FEATURE
<222> LOCATION: (661)..(661)
<223> OTHER INFORMATION: Xaa at position 661 is Ala or Glu
<220> FEATURE:
<221> NAME/KEY: MISC_FEATURE
<222> LOCATION: (663)..(663)
<223> OTHER INFORMATION: Xaa at position 663 is Asp or Glu
<220> FEATURE:
<221> NAME/KEY: MISC_FEATURE
<222> LOCATION: (672)..(672)
<223> OTHER INFORMATION: Xaa at position 672 is Ser or Met
<220> FEATURE:
<221> NAME/KEY: MISC_FEATURE
<222> LOCATION: (682)..(682)
<223> OTHER INFORMATION: Xaa at position 682 is Thr or Asn
<220> FEATURE:
<221> NAME/KEY: MISC_FEATURE
<222> LOCATION: (684)..(684)
<223> OTHER INFORMATION: Xaa at position 684 is Lys or Gln
<220> FEATURE:
<221> NAME/KEY: MISC_FEATURE
<222> LOCATION: (699)..(699)
<223> OTHER INFORMATION: Xaa at position 699 is Phe or Leu
<220> FEATURE:
<221> NAME/KEY: MISC_FEATURE
```

-continued

```
<222> LOCATION: (705)..(705)
<223> OTHER INFORMATION: Xaa at position 705 is Lys or Ile
<220> FEATURE:
<221> NAME/KEY: MISC_FEATURE
<222> LOCATION: (709)..(709)
<223> OTHER INFORMATION: Xaa at position 709 is Phe or Ile
<220> FEATURE:
<221> NAME/KEY: MISC_FEATURE
<222> LOCATION: (729)..(729)
<223> OTHER INFORMATION: Xaa at position 729 is Leu or Ser
<220> FEATURE:
<221> NAME/KEY: MISC_FEATURE
<222> LOCATION: (732)..(732)
<223> OTHER INFORMATION: Xaa at position 732 is Thr or Gln
<220> FEATURE:
<221> NAME/KEY: MISC_FEATURE
<222> LOCATION: (740)..(740)
<223> OTHER INFORMATION: Xaa at position 740 is Val or Ala
<220> FEATURE:
<221> NAME/KEY: MISC_FEATURE
<222> LOCATION: (760)..(760)
<223> OTHER INFORMATION: Xaa at position 760 is Ser, Leu or Arg
<220> FEATURE:
<221> NAME/KEY: MISC_FEATURE
<222> LOCATION: (769)..(769)
<223> OTHER INFORMATION: Xaa at position 769 is Gln or Asn
<220> FEATURE:
<221> NAME/KEY: MISC_FEATURE
<222> LOCATION: (771)..(771)
<223> OTHER INFORMATION: Xaa at position 771 is Leu or Ser
<220> FEATURE:
<221> NAME/KEY: MISC_FEATURE
<222> LOCATION: (778)..(778)
<223> OTHER INFORMATION: Xaa at position 778 is Ile or Val
<220> FEATURE:
<221> NAME/KEY: MISC_FEATURE
<222> LOCATION: (780)..(780)
<223> OTHER INFORMATION: Xaa at position 780 is Thr or Asn
<220> FEATURE:
<221> NAME/KEY: MISC_FEATURE
<222> LOCATION: (785)..(785)
<223> OTHER INFORMATION: Xaa at position 785 is Gln or absent
<220> FEATURE:
<221> NAME/KEY: MISC_FEATURE
<222> LOCATION: (786)..(786)
<223> OTHER INFORMATION: Xaa at position 786 is Ser, Ala, or Pro
<220> FEATURE:
<221> NAME/KEY: MISC_FEATURE
<222> LOCATION: (790)..(790)
<223> OTHER INFORMATION: Xaa at position 790 is Lys or Arg
<220> FEATURE:
<221> NAME/KEY: MISC_FEATURE
<222> LOCATION: (792)..(792)
<223> OTHER INFORMATION: Xaa at position 792 is Val or Ala
<220> FEATURE:
<221> NAME/KEY: MISC_FEATURE
<222> LOCATION: (798)..(798)
<223> OTHER INFORMATION: Xaa at position 798 is Pro or Leu
<220> FEATURE:
<221> NAME/KEY: MISC_FEATURE
<222> LOCATION: (799)..(799)
<223> OTHER INFORMATION: Xaa at position 799 is Met or Val
<220> FEATURE:
<221> NAME/KEY: MISC_FEATURE
<222> LOCATION: (807)..(807)
<223> OTHER INFORMATION: Xaa at position 807 is Phe or Leu
<220> FEATURE:
<221> NAME/KEY: MISC_FEATURE
<222> LOCATION: (811)..(811)
<223> OTHER INFORMATION: Xaa at position 811 is Val or Ile
<220> FEATURE:
<221> NAME/KEY: MISC_FEATURE
<222> LOCATION: (816)..(816)
<223> OTHER INFORMATION: Xaa at position 816 is Met of Lys
<220> FEATURE:
<221> NAME/KEY: MISC_FEATURE
<222> LOCATION: (821)..(821)
<223> OTHER INFORMATION: Xaa at position 821 is Lys or Asn
<220> FEATURE:
```

```
<221> NAME/KEY: MISC_FEATURE
<222> LOCATION: (827)..(827)
<223> OTHER INFORMATION: Xaa at position 827 is Val or Ile
<220> FEATURE:
<221> NAME/KEY: MISC_FEATURE
<222> LOCATION: (853)..(853)
<223> OTHER INFORMATION: Xaa at position 853 is Glu or Gly
<220> FEATURE:
<221> NAME/KEY: MISC_FEATURE
<222> LOCATION: (868)..(868)
<223> OTHER INFORMATION: Xaa at position 868 is Ala or Gly
<220> FEATURE:
<221> NAME/KEY: MISC_FEATURE
<222> LOCATION: (871)..(871)
<223> OTHER INFORMATION: Xaa at position 871 is Ala or Pro
<220> FEATURE:
<221> NAME/KEY: MISC_FEATURE
<222> LOCATION: (884)..(884)
<223> OTHER INFORMATION: Xaa at position 884 is Glu or His
<220> FEATURE:
<221> NAME/KEY: MISC_FEATURE
<222> LOCATION: (885)..(885)
<223> OTHER INFORMATION: Xaa at position 885 is Asn or His
<220> FEATURE:
<221> NAME/KEY: MISC_FEATURE
<222> LOCATION: (899)..(899)
<223> OTHER INFORMATION: Xaa at position 899 is Met or Val
<220> FEATURE:
<221> NAME/KEY: MISC_FEATURE
<222> LOCATION: (905)..(905)
<223> OTHER INFORMATION: Xaa at position 905 is Lys or Arg
<220> FEATURE:
<221> NAME/KEY: MISC_FEATURE
<222> LOCATION: (907)..(907)
<223> OTHER INFORMATION: Xaa at position 907 is Leu or Ile
<220> FEATURE:
<221> NAME/KEY: MISC_FEATURE
<222> LOCATION: (917)..(917)
<223> OTHER INFORMATION: Xaa at position 917 is Glu, Gln or Asp
<220> FEATURE:
<221> NAME/KEY: MISC_FEATURE
<222> LOCATION: (944)..(944)
<223> OTHER INFORMATION: Xaa at position 944 is Lys or Asn
<220> FEATURE:
<221> NAME/KEY: MISC_FEATURE
<222> LOCATION: (946)..(946)
<223> OTHER INFORMATION: Xaa at position 946 is Arg or Leu
<220> FEATURE:
<221> NAME/KEY: MISC_FEATURE
<222> LOCATION: (955)..(955)
<223> OTHER INFORMATION: Xaa at position 955 is Val or Thr
<220> FEATURE:
<221> NAME/KEY: MISC_FEATURE
<222> LOCATION: (969)..(969)
<223> OTHER INFORMATION: Xaa at position 969 is Pro or Gln
<220> FEATURE:
<221> NAME/KEY: MISC_FEATURE
<222> LOCATION: (984)..(984)
<223> OTHER INFORMATION: Xaa at position 984 is Glu or Asp
<220> FEATURE:
<221> NAME/KEY: MISC_FEATURE
<222> LOCATION: (989)..(989)
<223> OTHER INFORMATION: Xaa at position 989 is Arg or His
<220> FEATURE:
<221> NAME/KEY: MISC_FEATURE
<222> LOCATION: (1004)..(1004)
<223> OTHER INFORMATION: Xaa at position 1004 is Ser of Phe
<220> FEATURE:
<221> NAME/KEY: MISC_FEATURE
<222> LOCATION: (1006)..(1006)
<223> OTHER INFORMATION: Xaa at position 1006 is Ala or Ser
<220> FEATURE:
<221> NAME/KEY: MISC_FEATURE
<222> LOCATION: (1030)..(1030)
<223> OTHER INFORMATION: Xaa at position 1030 is Arg or Ser
<220> FEATURE:
<221> NAME/KEY: MISC_FEATURE
<222> LOCATION: (1051)..(1051)
<223> OTHER INFORMATION: Xaa at position 1051 is Gly or Asp
```

-continued

```
<220> FEATURE:
<221> NAME/KEY: MISC_FEATURE
<222> LOCATION: (1055)..(1055)
<223> OTHER INFORMATION: Xaa at position 1055 is Phe or Ser
<220> FEATURE:
<221> NAME/KEY: MISC_FEATURE
<222> LOCATION: (1073)..(1073)
<223> OTHER INFORMATION: Xaa at position 1073 is Met or Ile
<220> FEATURE:
<221> NAME/KEY: MISC_FEATURE
<222> LOCATION: (1081)..(1081)
<223> OTHER INFORMATION: Xaa at position 1081 is Met or Ile
<220> FEATURE:
<221> NAME/KEY: MISC_FEATURE
<222> LOCATION: (1085)..(1085)
<223> OTHER INFORMATION: Xaa at position 1085 is Gly or Glu
<220> FEATURE:
<221> NAME/KEY: MISC_FEATURE
<222> LOCATION: (1087)..(1087)
<223> OTHER INFORMATION: Xaa at position 1087 is Lys or Asn
<220> FEATURE:
<221> NAME/KEY: MISC_FEATURE
<222> LOCATION: (1089)..(1089)
<223> OTHER INFORMATION: Xaa at position 1089 is Thr or Ala
<220> FEATURE:
<221> NAME/KEY: MISC_FEATURE
<222> LOCATION: (1091)..(1091)
<223> OTHER INFORMATION: Xaa at position 1091 is Glu or Lys
<220> FEATURE:
<221> NAME/KEY: MISC_FEATURE
<222> LOCATION: (1094)..(1094)
<223> OTHER INFORMATION: Xaa at position 1094 is Ile or Leu
<220> FEATURE:
<221> NAME/KEY: MISC_FEATURE
<222> LOCATION: (1102)..(1102)
<223> OTHER INFORMATION: Xaa at position 1102 is Leu or Val
<220> FEATURE:
<221> NAME/KEY: MISC_FEATURE
<222> LOCATION: (1109)..(1109)
<223> OTHER INFORMATION: Xaa at position 1109 is Ala or Glu
<220> FEATURE:
<221> NAME/KEY: MISC_FEATURE
<222> LOCATION: (1110)..(1110)
<223> OTHER INFORMATION: Xaa at position 1110 is Thr or Met
<220> FEATURE:
<221> NAME/KEY: MISC_FEATURE
<222> LOCATION: (1115)..(1115)
<223> OTHER INFORMATION: Xaa at position 1115 is Ile or Met
<220> FEATURE:
<221> NAME/KEY: MISC_FEATURE
<222> LOCATION: (1118)..(1118)
<223> OTHER INFORMATION: Xaa at position 1118 is Lys or Asn
<220> FEATURE:
<221> NAME/KEY: MISC_FEATURE
<222> LOCATION: (1125)..(1125)
<223> OTHER INFORMATION: Xaa at position 1125 is Asn or Tyr
<220> FEATURE:
<221> NAME/KEY: MISC_FEATURE
<222> LOCATION: (1132)..(1132)
<223> OTHER INFORMATION: Xaa at position 1132 is Gly, Met, or Leu
<220> FEATURE:
<221> NAME/KEY: MISC_FEATURE
<222> LOCATION: (1133)..(1133)
<223> OTHER INFORMATION: Xaa at position 1133 is Asn or Glu
<220> FEATURE:
<221> NAME/KEY: MISC_FEATURE
<222> LOCATION: (1134)..(1134)
<223> OTHER INFORMATION: Xaa at position 1134 is Ile or Thr
<220> FEATURE:
<221> NAME/KEY: MISC_FEATURE
<222> LOCATION: (1135)..(1135)
<223> OTHER INFORMATION: Xaa at position 1135 is Glu or absent
<220> FEATURE:
<221> NAME/KEY: MISC_FEATURE
<222> LOCATION: (1136)..(1136)
<223> OTHER INFORMATION: Xaa at position 1136 is Val, Lys, or absent
<220> FEATURE:
<221> NAME/KEY: MISC_FEATURE
<222> LOCATION: (1137)..(1137)
```

<223> OTHER INFORMATION: Xaa at position 1137 is Asn, Leu, or absent
<220> FEATURE:
<221> NAME/KEY: MISC_FEATURE
<222> LOCATION: (1138)..(1138)
<223> OTHER INFORMATION: Xaa at position 1138 is Val or absent

<400> SEQUENCE: 11

```
Met Glu Lys His Ile Phe Leu Leu Ile Leu Xaa Xaa Leu Val Gln Xaa
1               5                   10                  15

Tyr Xaa Val Ser Ser Ile Xaa Xaa Xaa Xaa Ser Asn Glu Thr Asp
            20                  25                  30

Gln Glu Ala Leu Leu Ala Phe Arg Asn Leu Xaa Xaa Ser Asp Ser Ser
            35                  40                  45

Xaa Phe Leu Ala Asn Asn Trp Thr Lys Asn Xaa Thr Ser Phe Cys Ser
    50                  55                  60

Trp Phe Gly Val Thr Cys Ser Pro Xaa Arg Gln Arg Val Val Ala Leu
65                  70                  75                  80

Xaa Leu Pro Xaa Leu Gln Leu Xaa Gly Thr Ile Ser Pro Ser Leu Ala
                85                  90                  95

Asn Leu Ser Phe Leu Xaa Xaa Leu Asn Leu Xaa Asn Asn Xaa Xaa His
            100                 105                 110

Xaa Xaa Ile Pro Xaa Gly Ile Gly Xaa Arg Leu Pro Arg Leu Arg Val
        115                 120                 125

Ile Asp Ile Gln Asn Asn Gln Leu Xaa Gly Ser Ile Pro Xaa Ser Leu
130                 135                 140

Phe Gln His Xaa Xaa Val Gln Ile Ile Ser Leu Ala Phe Asn Lys Leu
145                 150                 155                 160

Xaa Gly Glu Met Trp Asn Gly Thr Trp Tyr Val Pro Glu Leu Arg Val
                165                 170                 175

Leu Asn Leu Arg Asn Asn Thr Xaa Thr Gly Xaa Ile Pro Pro Ser Ile
            180                 185                 190

Gly Asn Ala Thr Lys Leu Met Asn Xaa Ser Leu Xaa Xaa Asn Arg Ile
            195                 200                 205

Xaa Gly Asn Ile Pro Xaa Glu Ile Gly Asn Leu Ser Gln Leu Xaa Glu
210                 215                 220

Leu Xaa Leu Ser Arg Asn Gln Leu Thr Gly Ser Ile Pro Xaa Thr Leu
225                 230                 235                 240

Phe Asn Ile Ser Ser Leu Leu Val Xaa Ser Leu Ala Xaa Asn Ser Leu
                245                 250                 255

Ser Gly Pro Leu Xaa Xaa Xaa Xaa Xaa Xaa Xaa Xaa Xaa Ser Asn
            260                 265                 270

Leu Glu His Xaa Gly Xaa Ser Tyr Asn Gln Ile Xaa Gly Xaa Ile Xaa
            275                 280                 285

Ser Asn Ile Cys Gln Xaa Xaa Xaa Leu Xaa Val Leu Ser Ile Ser Xaa
            290                 295                 300

Asn Asn Ile Thr Gly Glu Xaa Pro Arg Asn Xaa Gly Cys Leu Xaa Lys
305                 310                 315                 320

Leu Glu Glu Xaa Tyr Ile Gly Tyr Asn Xaa Ile Xaa Gly Xaa Ile Pro
                325                 330                 335

Xaa Ser Leu Gly Asn Ile Ser Thr Leu Gln Xaa Leu His Cys Gly Xaa
            340                 345                 350

Asn Xaa Met Xaa Gly Glu Xaa Pro Pro Glu Leu Gly Lys Leu Ser Asn
            355                 360                 365

Leu Arg Xaa Ile Xaa Phe Xaa Glu Asn Tyr Asn Leu Xaa Gly Glu Ile
            370                 375                 380
```

```
Pro Asn Xaa Ile Phe Asn Ile Ser Ser Leu Glu Phe Ile Xaa Phe Xaa
385                 390                 395                 400

Phe Asn Tyr Leu Ser Gly Arg Ile Pro Xaa Leu Leu His Xaa Pro Asn
            405                 410                 415

Leu Ile Gln Leu Xaa Leu Ala Asn Asn Gln Leu Glu Gly Glu Ile Pro
            420                 425                 430

Arg Tyr Ile Thr Asn Ala Thr Xaa Leu Glu Xaa Leu Xaa Leu Ser Xaa
            435                 440                 445

Asn Xaa Leu Thr Gly Xaa Ile Pro Xaa Xaa Leu Gly Asn Leu Arg Xaa
            450                 455                 460

Leu Xaa Xaa Leu Phe Leu His His Asn Gln Leu Xaa Glu Leu Gly Phe
465                 470                 475                 480

Phe Asp Ser Leu Val Xaa Cys Arg Met Leu Xaa Tyr Val Gln Val Gly
            485                 490                 495

Ser Asn Pro Leu Asn Xaa Val Leu Pro Ser Ser Ile Gly Asn Leu Ser
            500                 505                 510

Ser Xaa Val Glu Tyr Phe His Ile Gly Asp Ala Gln Ile Xaa Gly Phe
    515                 520                 525

Ile Pro Thr Ser Thr Gly Asn Met Xaa Gly Leu Thr Thr Leu Val Xaa
            530                 535                 540

Gln Asp Asn Xaa Leu Thr Gly Asn Ile Pro Arg Glu Ile Xaa Xaa Leu
545                 550                 555                 560

Lys Gln Leu Gln Gly Leu Phe Leu Xaa Asn Asn Xaa Leu Gln Gly Asp
            565                 570                 575

Ile Xaa Xaa Val Val Cys Asp Leu Ser Asn Leu Val Arg Leu Xaa Leu
            580                 585                 590

Ser Xaa Asn Glu Leu Ser Gly Val Ile Pro Xaa Cys Xaa Gly Xaa Leu
    595                 600                 605

Xaa Met Leu Gln Xaa Leu Phe Leu Gly Ser Asn Xaa Phe Xaa Ser Xaa
    610                 615                 620

Leu Pro Leu Ser Xaa Trp Lys Met Xaa Xaa Leu Leu Xaa Xaa Asn Xaa
625                 630                 635                 640

Ser Xaa Asn Ser Xaa Xaa Gly Glu Val Pro Ser Asp Ile Gly Glu Leu
            645                 650                 655

Lys Ala Ile Val Xaa Ile Xaa Ile Ser Gly Asn His Phe Ser Gly Xaa
            660                 665                 670

Ile Pro Ser Asn Leu Gly Glu Leu Gln Xaa Leu Xaa Leu Leu Ser Leu
            675                 680                 685

Ser Asn Asn Ser Phe Ser Gly Pro Ile Pro Xaa Ser Phe Ser Asn Leu
    690                 695                 700

Xaa Ser Leu Glu Xaa Leu Asp Leu Ser Leu Asn Asn Leu Ser Gly Thr
705                 710                 715                 720

Ile Pro Lys Ser Phe Glu Lys Leu Xaa Tyr Leu Xaa Ser Ile Asn Val
            725                 730                 735

Ser Phe Asn Xaa Leu Glu Gly Glu Ile Pro Ser Gly Gly Val Phe Ala
            740                 745                 750

Asn Ser Thr Leu Gln Ser Phe Xaa Gly Asn Lys Gly Leu Cys Gly Arg
            755                 760                 765

Xaa Ile Xaa Glu Val Pro Ala Cys Ala Xaa Thr Xaa Pro Glu Gln Gln
            770                 775                 780

Xaa Xaa Lys Ser Lys Xaa Leu Xaa Leu Lys Ile Val Thr Xaa Xaa Val
785                 790                 795                 800
```

```
Ile Ser Phe Phe Leu Ile Xaa Leu Leu Val Xaa Ser Ile Trp Ile Xaa
                805                 810                 815

Lys Arg Lys Lys Xaa Gly Lys Ser Lys Asp Xaa Glu Lys Val Pro Glu
        820                 825                 830

Met Arg Thr Tyr Gln Leu Ile Ser Tyr His Glu Ile Gln Arg Ala Thr
        835                 840                 845

Asn Asn Phe Asp Xaa Ser Asn Leu Ile Gly Val Gly Ser Gly Ser
    850                 855                 860

Val Tyr Lys Xaa Thr Leu Xaa Ser Gly Ile Val Ala Ile Lys Val
865                 870                 875                 880

Leu Asp Leu Xaa Xaa Glu Glu Val Cys Lys Arg Phe Asp Thr Glu Cys
                885                 890                 895

Glu Val Xaa Arg Asn Val Arg His Xaa Asn Xaa Val Ser Val Ile Thr
        900                 905                 910

Thr Cys Ser Ser Xaa His Ile Arg Ala Phe Val Leu Gln Tyr Met Pro
        915                 920                 925

Asn Gly Ser Leu Asp Asn Trp Leu Tyr Lys Asp Arg His Leu Xaa
    930                 935                 940

Leu Xaa Gln Arg Val Thr Ile Met Leu Asp Xaa Ala Met Ala Ile Glu
945                 950                 955                 960

Tyr Leu His His Gly Asn Asp Thr Xaa Ile Val His Cys Asp Leu Lys
                965                 970                 975

Pro Ala Asn Val Leu Leu Asp Xaa Asp Met Val Ala Xaa Val Gly Asp
                980                 985                 990

Phe Gly Ile Ser Lys Ile Leu Ala Val Ser Lys Xaa Met Xaa His Thr
                995                 1000                1005

Lys Thr Leu Gly Thr Leu Gly Tyr Ile Ala Pro Glu Tyr Gly Ser
    1010                1015                1020

Glu Gly Ile Val Ser Thr Xaa Gly Asp Val Tyr Ser Tyr Gly Ile
    1025                1030                1035

Met Leu Met Glu Val Leu Ala Lys Arg Arg Pro Thr Xaa Glu Glu
    1040                1045                1050

Ile Xaa Asn Glu Asn Leu Gly Leu Arg Glu Trp Ile Thr Arg Ala
    1055                1060                1065

Phe Pro Arg Thr Xaa Met Glu Val Val Asp Ala Asp Xaa Phe His
    1070                1075                1080

Asp Xaa Glu Xaa Ile Xaa Ser Xaa Ser Glu Xaa Cys Ile Leu Ser
    1085                1090                1095

Met Ile Glu Xaa Ala Leu Asp Cys Thr Lys Xaa Xaa Pro Glu Ser
    1100                1105                1110

Arg Xaa Thr Met Xaa Asp Val Val Lys Arg Leu Xaa Lys Ile Lys
    1115                1120                1125

Asn Thr Phe Xaa Xaa Xaa Xaa Xaa Xaa Xaa
    1130                1135

<210> SEQ ID NO 12
<211> LENGTH: 28
<212> TYPE: PRT
<213> ORGANISM: Artificial
<220> FEATURE:
<223> OTHER INFORMATION: flgII-28 peptide
<220> FEATURE:
<221> NAME/KEY: MISC_FEATURE
<222> LOCATION: (13)..(13)
<223> OTHER INFORMATION: Xaa at position 13 is Ala or Val
<220> FEATURE:
<221> NAME/KEY: MISC_FEATURE
```

```
<222> LOCATION: (16)..(16)
<223> OTHER INFORMATION: Xaa at position 16 is Ser of Phe
<220> FEATURE:
<221> NAME/KEY: MISC_FEATURE
<222> LOCATION: (27)..(27)
<223> OTHER INFORMATION: Xaa at position 27 is Glu or Asp

<400> SEQUENCE: 12

Glu Ser Thr Asn Ile Leu Gln Arg Met Arg Glu Leu Xaa Val Gln Xaa
1               5                   10                  15

Arg Asn Asp Ser Asn Ser Ala Thr Asp Arg Xaa Ala
            20                  25

<210> SEQ ID NO 13
<211> LENGTH: 28
<212> TYPE: PRT
<213> ORGANISM: Artificial
<220> FEATURE:
<223> OTHER INFORMATION: flgII-28 peptide
<220> FEATURE:
<221> NAME/KEY: MISC_FEATURE
<222> LOCATION: (3)..(3)
<223> OTHER INFORMATION: Xaa at position 3 is Thr or Val
<220> FEATURE:
<221> NAME/KEY: MISC_FEATURE
<222> LOCATION: (4)..(4)
<223> OTHER INFORMATION: Xaa at position 4 is Asn or Ser
<220> FEATURE:
<221> NAME/KEY: MISC_FEATURE
<222> LOCATION: (23)..(23)
<223> OTHER INFORMATION: Xaa at position 23 is Ala or Ser
<220> FEATURE:
<221> NAME/KEY: MISC_FEATURE
<222> LOCATION: (24)..(24)
<223> OTHER INFORMATION: Xaa at position 24 is Thr or Glu
<220> FEATURE:
<221> NAME/KEY: MISC_FEATURE
<222> LOCATION: (25)..(25)
<223> OTHER INFORMATION: Xaa at position 25 is Asp or Gly
<220> FEATURE:
<221> NAME/KEY: MISC_FEATURE
<222> LOCATION: (27)..(27)
<223> OTHER INFORMATION: Xaa at position 27 is Glu or Asp

<400> SEQUENCE: 13

Glu Ser Xaa Xaa Ile Leu Gln Arg Met Arg Glu Leu Ala Val Gln Ser
1               5                   10                  15

Arg Asn Asp Ser Asn Ser Xaa Xaa Xaa Arg Xaa Ala
            20                  25

<210> SEQ ID NO 14
<211> LENGTH: 28
<212> TYPE: PRT
<213> ORGANISM: Artificial
<220> FEATURE:
<223> OTHER INFORMATION: flgII-28 peptide

<400> SEQUENCE: 14

Glu Ile Gly Ser Asn Leu Gln Arg Ile Arg Glu Leu Ser Val Gln Ser
1               5                   10                  15

Ser Asn Ala Thr Asn Ser Ala Ser Asp Arg Asp Ala
            20                  25

<210> SEQ ID NO 15
<211> LENGTH: 28
<212> TYPE: PRT
<213> ORGANISM: Artificial
<220> FEATURE:
<223> OTHER INFORMATION: flgII-28 peptide
```

```
<400> SEQUENCE: 15

Glu Ile Asn Asn Asn Leu Gln Arg Val Arg Glu Leu Ala Val Gln Ser
1               5                   10                  15

Ala Asn Ser Thr Asn Ser Gln Ser Asp Leu Asp Ser
            20                  25

<210> SEQ ID NO 16
<211> LENGTH: 143
<212> TYPE: PRT
<213> ORGANISM: solanum lycopersicum
<220> FEATURE:
<221> NAME/KEY: MISC_FEATURE
<222> LOCATION: (130)..(130)
<223> OTHER INFORMATION: Xaa at position 130 is Valine or Isoleucine

<400> SEQUENCE: 16

Pro Ser Leu Ala Asn Leu Ser Phe Leu Ile Glu Leu Asn Leu Ala Asn
1               5                   10                  15

Asn Asn Leu His Ser Glu Ile Pro Asp Gly Ile Gly Arg Leu Pro Arg
            20                  25                  30

Leu Arg Val Ile Asp Ile Gln Asn Asn Gln Leu His Gly Ser Ile Pro
        35                  40                  45

Thr Ser Leu Phe Gln His Gly Ser Val Gln Ile Ile Ser Leu Ala Phe
    50                  55                  60

Asn Lys Leu Gly Gly Glu Met Trp Asn Gly Thr Trp Tyr Val Pro Glu
65                  70                  75                  80

Leu Arg Val Leu Asn Leu Arg Asn Asn Thr Ile Thr Gly Val Ile Pro
                85                  90                  95

Pro Ser Ile Gly Asn Ala Thr Lys Leu Met Asn Phe Ser Leu Asn Gly
            100                 105                 110

Asn Arg Ile Asn Gly Asn Ile Pro Met Glu Ile Gly Asn Leu Ser Gln
        115                 120                 125

Leu Xaa Glu Leu Ser Leu Ser Arg Asn Gln Leu Thr Gly Ser Ile
    130                 135                 140

<210> SEQ ID NO 17
<211> LENGTH: 172
<212> TYPE: PRT
<213> ORGANISM: solanum lycopersicum

<400> SEQUENCE: 17

Pro Ser Thr Leu Phe Asn Ile Ser Ser Leu Leu Val Val Ser Leu Ala
1               5                   10                  15

Tyr Asn Ser Leu Ser Gly Pro Leu Phe Pro Asp Asp Arg Arg Asn Val
            20                  25                  30

Leu Ser Ser Asn Leu Glu His Ile Gly Val Ser Tyr Asn Gln Ile Thr
        35                  40                  45

Gly His Ile Pro Ser Asn Ile Cys Gln Phe Thr Ala Leu Arg Val Leu
    50                  55                  60

Ser Ile Ser Tyr Asn Asn Ile Thr Gly Glu Ile Pro Arg Asn Ile Gly
65                  70                  75                  80

Cys Leu Ala Lys Leu Glu Glu Phe Tyr Ile Gly Tyr Asn Ala Ile Asn
                85                  90                  95

Gly Thr Ile Pro Ala Ser Leu Gly Asn Ile Ser Thr Leu Gln Asn Leu
            100                 105                 110

His Cys Gly Ser Asn His Met Glu Gly Glu Leu Pro Pro Glu Leu Gly
        115                 120                 125
```

```
Lys Leu Ser Asn Leu Arg Gln Ile Asn Phe Glu Glu Asn Tyr Asn Leu
            130                 135                 140

Ile Gly Glu Ile Pro Asn Thr Ile Phe Asn Ile Ser Ser Leu Glu Phe
145                 150                 155                 160

Ile Ala Phe Thr Phe Asn Tyr Leu Ser Gly Arg Ile
                165                 170

<210> SEQ ID NO 18
<211> LENGTH: 145
<212> TYPE: PRT
<213> ORGANISM: solanum lycopersicum
<220> FEATURE:
<221> NAME/KEY: MISC_FEATURE
<222> LOCATION: (123)..(123)
<223> OTHER INFORMATION: Xaa at position 123 is Threonine or Alanine

<400> SEQUENCE: 18

Pro Asn Leu Leu His Leu Pro Asn Leu Ile Gln Leu Leu Ala Asn
1               5                   10                  15

Asn Gln Leu Glu Gly Glu Ile Pro Arg Tyr Ile Thr Asn Ala Thr Asn
            20                  25                  30

Leu Glu Leu Leu Glu Leu Ser Asp Asn Leu Leu Thr Gly Thr Ile Pro
        35                  40                  45

Asn Asp Leu Gly Asn Leu Arg Glu Leu Arg Asp Leu Phe Leu His His
    50                  55                  60

Asn Gln Leu Thr Glu Leu Gly Phe Phe Asp Ser Leu Val Lys Cys Arg
65                  70                  75                  80

Met Leu Arg Tyr Val Gln Val Gly Ser Asn Pro Leu Asn Asp Val Leu
                85                  90                  95

Pro Ser Ser Ile Gly Asn Leu Ser Ser Thr Val Glu Tyr Phe His Ile
            100                 105                 110

Gly Asp Ala Gln Ile Asn Gly Phe Ile Pro Xaa Ser Thr Gly Asn Met
        115                 120                 125

Thr Gly Leu Thr Thr Leu Val Phe Gln Asp Asn Ser Leu Thr Gly Asn
    130                 135                 140

Ile
145

<210> SEQ ID NO 19
<211> LENGTH: 192
<212> TYPE: PRT
<213> ORGANISM: solanum lycopersicum
<220> FEATURE:
<221> NAME/KEY: MISC_FEATURE
<222> LOCATION: (164)..(164)
<223> OTHER INFORMATION: Xaa at position 164 is Leucine or Phenylalanine

<400> SEQUENCE: 19

Pro Arg Glu Ile Arg Lys Leu Lys Gln Leu Gln Gly Leu Phe Leu Val
1               5                   10                  15

Asn Asn Gly Leu Gln Gly Asp Ile Ala Glu Val Val Cys Asp Leu Ser
            20                  25                  30

Asn Leu Val Arg Leu Ala Leu Ser Glu Asn Glu Leu Ser Gly Val Ile
        35                  40                  45

Pro Glu Cys Leu Gly Asn Leu Thr Met Leu Gln Gln Leu Phe Leu Gly
    50                  55                  60

Ser Asn Lys Phe Glu Ser Lys Leu Pro Leu Ser Phe Trp Lys Met Ser
65                  70                  75                  80

Ser Leu Leu Tyr Leu Asn Met Ser Arg Asn Ser Ile Lys Gly Glu Val
```

```
                    85                  90                  95
Pro Ser Asp Ile Gly Glu Leu Lys Ala Ile Ala Ile Asp Ile Ser
                100                 105                 110

Gly Asn His Phe Ser Gly Ser Ile Pro Ser Asn Leu Gly Glu Leu Gln
            115                 120                 125

Thr Leu Lys Leu Leu Ser Leu Ser Asn Asn Ser Phe Ser Gly Pro Ile
        130                 135                 140

Pro Phe Ser Phe Ser Asn Leu Lys Ser Leu Glu Phe Leu Asp Leu Ser
145                 150                 155                 160

Leu Asn Asn Xaa Ser Gly Thr Ile Pro Lys Ser Phe Glu Lys Leu Leu
                165                 170                 175

Tyr Leu Thr Ser Ile Asn Val Ser Phe Asn Val Leu Glu Gly Glu Ile
                180                 185                 190

<210> SEQ ID NO 20
<211> LENGTH: 22
<212> TYPE: PRT
<213> ORGANISM: solanum lycopersicum
<220> FEATURE:
<221> NAME/KEY: MISC_FEATURE
<222> LOCATION: (22)..(22)
<223> OTHER INFORMATION: Xaa at position 22 is Lysine or Glutamine

<400> SEQUENCE: 20

Gly Val Gly Gly Ser Gly Ser Val Tyr Lys Ala Thr Leu Ala Ser Gly
1               5                   10                  15

Ile Val Val Ala Ile Xaa
            20

<210> SEQ ID NO 21
<211> LENGTH: 16
<212> TYPE: PRT
<213> ORGANISM: solanum lycopersicum

<400> SEQUENCE: 21

Thr Pro Ile Val His Cys Asp Leu Lys Pro Ala Asn Val Leu Leu Asp
1               5                   10                  15

<210> SEQ ID NO 22
<211> LENGTH: 10
<212> TYPE: PRT
<213> ORGANISM: solanum lycopersicum
<220> FEATURE:
<221> NAME/KEY: MISC_FEATURE
<222> LOCATION: (2)..(2)
<223> OTHER INFORMATION: Xaa at position 2 is Threonine or Proline

<400> SEQUENCE: 22

Gly Xaa Leu Gly Tyr Ile Ala Pro Glu Tyr
1               5                   10
```

FLAGELLIN-SENSING 3 ('FLS3') PROTEIN AND METHODS OF USE

This application is a national stage application under 35 U.S.C. § 371 of PCT Application No. PCT/US2015/039520, filed Jul. 8, 2015, which claims priority benefit of U.S. Provisional Patent Application Ser. No. 62/021,995, filed Jul. 8, 2014, each of which is hereby incorporated by reference in its entirety.

This invention was made with government support under the following grant numbers: IOS-1025642 awarded by the National Science Foundation; R01-GM078021 awarded by the National Institutes of Health; and 2010-65108-20503 awarded by the United States Department of Agriculture/National Institute of Food and Agriculture. The government has certain rights in this invention.

FIELD OF THE INVENTION

The present invention relates generally to disease resistance in plants.

BACKGROUND OF THE INVENTION

Animals and plants rely on pattern recognition receptors ("PRRs") to detect conserved microbe-associated molecular patterns ("MAMPs") in potential pathogens (Zhang et al., "Plant Immunity Triggered by Microbial Molecular Signatures," *Mol Plant* 3:783-793 (2010)). Two well understood peptide MAMPs, flg22 and flgII-28, are derived from flagellin, which forms the 'tail' bacteria use for motility (see FIG. 1 of Gomez-Gomez et al., "Flagellin Perception: A Paradigm for Innate Immunity," *Trends Plant Sci* 7:251-256 (2002)). In humans, the Toll-like receptor 5 (TLRS) binds a flagellin-derived MAMP that involves a peptide region known as flgII-28 thereby activating innate immunity. In plants, the best-characterized PRR is FLS2 that binds flg22. FLS2, which is conserved in monocots and dicots, is a leucine-rich repeat ("LRR") receptor-like kinase ("RLK") that activates pattern-triggered immunity ("PTI") (Gomez-Gomez et al., "FLS2: An LRR Receptor-like Kinase Involved in the Perception of the Bacterial Elicitor Flagellin in *Arabidopsis*," *Mol Cell* 5:1003-1011 (2000)). Tomato and other species in the family Solanaceae, but not *Arabidopsis* and other plants, recognizes flgII-28 (Cai et al., "The Plant Pathogen *Pseudomonas syringae* pv. tomato is Genetically Monomorphic and Under Strong Selection to Evade Tomato Immunity," *PLoS Pathogens* 7:e1002130 (2011)). This finding is significant because some pathogens have a divergent flg22 region that allows them to evade detection by FLS2 (Sun et al., "Within-species Flagellin Polymorphism in *Xanthomonas campestris* pv. *campestris* and Its Impact on Elicitation of *Arabidopsis* FLAGELLIN SENSING2-dependent Defenses," *Plant Cell* 18:764-779 (2006), which is hereby incorporated by reference in its entirety). The existence of a PRR that recognizes flgII-28 may therefore allow tomato and other plant species to recognize a broader range of bacterial pathogens.

Importantly, PRRs can be transferred from one plant species to another and remain functional. For example, the *Arabidopsis* receptor EFR, which recognizes the bacterial MAMP elongation factor ("EF") Tu, was transformed into tomato and *N. benthamiana*, which are normally unable to detect EF-Tu. (Lacombe et al., "Interfamily Transfer of a Plant Pattern-Recognition Receptor Confers Broad-spectrum Bacterial Resistance," *Nat Biotechnol* 28:365-369 (2010)). It was shown that the EFR-expressing plants were resistant to previously virulent pathogens (Lacombe et al., "Interfamily Transfer of a Plant Pattern-Recognition Receptor Confers Broad-spectrum Bacterial Resistance," *Nat Biotechnol* 28:365-369 (2010)). Other recent examples include the transfer of the ReMAX PRR from *Arabidopsis* to tobacco and the expression of the tomato Ve1 gene in *Arabidopsis* (Jehle et al., "The Receptor-Like Protein ReMAX of *Arabidopsis* Detects the Microbe-Associated Molecular Pattern eMax from *Xanthomonas*" *Plant Cell* 25(6):2330-2340 (2013) and Fradin et al., "Interfamily Transfer of Tomato Ve1 Mediates *Verticillium* Resistance in *Arabidopsis*" *Plant Physiol* 156(4): 2255-2265 (2011)). In both cases, the genes provided new recognition specificity.

Significant agricultural benefits may arise from the identification of PRRs that occur in only some plant species. Such species-specific PRRs can be used to broaden and enhance disease resistance when transferred into economically important and taxonomically diverse plants that do not naturally express them (see Lacombe et al., "Interfamily Transfer of a Plant Pattern-Recognition Receptor Confers Broad-spectrum Bacterial Resistance," *Nat Biotechnol* 28:365-369 (2010)). Despite this potential, there are few cloned PRR genes available from plants and the majority of these are widely conserved, so they do not offer the possibility of interspecies transfer. Further, despite progress in understanding the genetic control of plant resistance to pathogens, little progress has been reported in the identification and analysis of key regulators of pathogen resistance. Characterization of such genes would allow for the genetic engineering of plants with a variety of desirable traits.

The present invention is directed to overcoming these and other deficiencies in the art.

SUMMARY OF THE INVENTION

One aspect of the present invention relates to a nucleic acid construct that includes a nucleic acid molecule that encodes a FLAGELLIN-SENSING 3 ("FLS3") protein; a 5' heterologous DNA promoter sequence; and a 3' terminator sequence, where the nucleic acid molecule, the DNA promoter sequence, and the terminator sequence are operatively coupled to permit transcription of the nucleic acid molecule.

Another aspect of the present invention relates to a method of expressing a nucleic acid molecule in a plant. This method involves providing a transgenic plant or plant seed transformed with a nucleic acid construct comprising a nucleic acid molecule that encodes an FLS3 protein; a 5' heterologous DNA promoter sequence; and a 3' terminator sequence, where the nucleic acid molecule, the DNA promoter sequence, and the terminator sequence are operatively coupled to permit transcription of the nucleic acid molecule. The method also involves growing the transgenic plant or a plant grown from the transgenic plant seed under conditions effective to express the nucleic acid molecule in said transgenic plant or said plant grown from the transgenic plant seed.

Yet another aspect of the present invention relates to a method of imparting disease resistance to a plant. This method involves transforming a plant or a plant seed with a nucleic acid molecule that increases expression of an FLS3 protein, where said transforming is effective in imparting disease resistance to the transformed plant or to a transgenic plant produced from the transformed plant seed.

A further aspect of the present invention relates to a method of imparting disease resistance to a plant. The method involves providing a plant having a gene encoding an FLS3 protein, and applying to the plant and/or area of cultivation of the plant a flgII-28 peptide or an FLS3-binding portion thereof, thereby imparting disease resistance to the plant.

A further aspect of the present invention relates to a method of identifying a candidate plant suitable for breeding that displays enhanced disease resistance. This method involves providing a candidate plant; analyzing the candidate plant for the presence, in its genome, of a gene encoding an FLS3 protein; identifying, based on said analyzing, a candidate plant suitable for breeding that includes in its genome, a gene encoding an FLS3 protein; and breeding the identified plant with at least one other plant.

Yet a further aspect of the present invention relates to a method for enhancing efficiency of transformation of a plant by *Agrobacterium*. This method involves transforming a plant or a plant seed with a nucleic acid construct effective to silence expression of a nucleic acid molecule that encodes an FLS3 protein, where said transforming is effective to reduce or eliminate expression of FLS3 protein in the plant and said nucleic acid construct. The nucleic acid construct includes a nucleic acid molecule configured to silence FLS3 protein expression; a 5' DNA promoter sequence; and a 3' terminator sequence, where the nucleic acid molecule, the promoter, and the terminator are operatively coupled to permit expression of the nucleic acid molecule.

Plants are able to detect the presence of foreign invading organisms through the perception of conserved MAMPs by cell surface PRRs. Extensive research has characterized the perception of the flagellin-derived MAMP flg22 by the PRR FLS2, and the subsequent intracellular signaling events which lead to induction of immune responses. Several other MAMPs have been isolated in recent years, but few plant PRR proteins have been characterized. Recently, an additional epitope from flagellin, termed flgII-28, was found to be detected specifically by tomato and other related solanaceous plants in an FLS2-independent manner (Clarke et al., "Allelic Variation in Two Distinct *Pseudomonas syringae* Flagellin Epitopes Modulates the Strength of Plant Immune Responses But Not Bacterial Motility," *New Phytol* 200: 847-860 (2013), which is hereby incorporated by reference in its entirety). As described herein, to identify the gene encoding the receptor responsible for this recognition, termed FLS3 (i.e., FLAGELLIN-SENSING 3, previously referred to as FlgII-28 Sensitivity 3 in U.S. Provisional Application No. 62/021,995), natural variation in tomato heirloom varieties and a mapping-by-sequencing approach was used. Expression of the wild type FLS3 gene in non-responsive plants confers recognition of flgII-28 and enhances immune responses. Photo-affinity labeling demonstrated specific binding of the MAMP by FLS3, indicating it is the flgII-28 receptor. FLS3 represents an orthogonal means for flagellin perception and therefore expression of this solanaceous-specific PRR in crop plants that are unable to detect flgII-28 could be deployed as a tactic to combat pathogens that have evolved to evade flg22 detection and offers a strategy of controlling bacterial diseases without the use of pesticides.

The importance of PRRs has been demonstrated recently when it was shown that they can be introduced into plants lacking such proteins to bolster disease resistance (Lacombe et al., "Interfamily Transfer of a Plant Pattern-Recognition Receptor Confers Broad-spectrum Bacterial Resistance," *Nat Biotechnol* 28:365-369 (2010), which is hereby incorporated by reference in its entirety); however, the identification of plant immune receptors has proven difficult, particularly in crop species. Thus, the findings described herein mark an important and significant step in understanding plant immunity and modulating (e.g., enhancing) disease resistance in plants. These findings add to the molecular and genetic toolbox available for research in crop plants, and highlight advantages of using natural variation to increase understanding about plant immunity. Perception of an additional element of flagellin likely allows tomato to recognize a broader range of bacterial pathogens. Therefore, significant agricultural benefits may be achieved by the introduction of FLS3 into other plants (e.g., crop plants).

BRIEF DESCRIPTION OF THE DRAWINGS

FIG. 1A shows an overview of the genetics approach used for identifying FLS3. *S. pimpinellifolium* LA1589 and *S. lycopersicum* cv. 'Yellow Pear' differ in their production of reactive oxygen species (ROS) in response to flgII-28, whereas production of ROS is a hallmark of MAMP-related responses in plants. In order to identify the responsible gene by bulked segregant analysis, segregating populations were generated by crossing flgII-28 sensitive (LA1589) and insensitive (Yellow Pear) accessions. The resulting F1 plants were responsive to flgII-28, suggesting the allele responsible for the sensitivity is dominant. Testing for the sensitivity of F2 plants to 100 nM flgII-28 treatment using the ROS assay revealed a segregation ratio of LA1589×Yellow Pear of 468:108. FIG. 1B is a schematic diagram of a bulked segregant analysis approach combined with next generation sequencing and FIG. 1C shows an overview of the next-generation sequencing approach used to identify FLS3 candidate genes. To identify the genomic region linked to flgII-28 insensitivity, DNA libraries for next-generation Illumina® sequencing were generated using flgII-28 non-responsive F2 plants described in FIG. 1A. Reads were filtered and trimmed for quality before being mapped onto the Yellow Pear genome (Strickler et al., "Comparative genomics and phylogenetic discordance of cultivated tomato and close wild relatives," *Peer J* 26:e793 (2015), which is hereby incorporated by reference in its entirety). SNP calling was performed between Yellow Pear and *S. pimpinellifolium* LA1589. FIG. 1D shows experimental results demonstrating that only chromosome 4 had a notable deviation from the expected 1:1 LA1589:Yellow Pear SNP ratio, with one region in particular having very few LA1589-specific SNPs. This region, spanning 2.619 to 5.486 Mb on chromosome 4, contains 322 annotated genes including 9 leucine-rich repeat, receptor-like kinases (LRR-RLKs). FIG. 1E is a diagram illustrating experimental results demonstrating how fine genetic mapping was used to narrow down the candidate list to a single gene on chromosome 4. The physical distance (in Mb) on chromosome 4 is indicated, and at each indicated location CAPS markers were used to differentiate between the two parents. The number of recombination events observed using 28 non-responding plants is shown.

FIGS. 2A-2F elucidate the FLS3 protein structure, its general similarity to FLS2, and FLS3 orthologs from other *Solanaceae* species. FIG. 2A is a schematic representation of the wild type FLS3 allele which encodes a class XII LRR RLK with 27 LRRs and an intracellular non-RD kinase domain (amino acid sequences shown with reference to SEQ ID NO:2, with identified segments shown separately in SEQ ID NOs: 16-22). Additional FLS3 variants are also indicated on the schematic representation, and activity data is demonstrated (FIG. 2B). These variations correspond to two additional FLS3 alleles that were isolated from different tomato accessions. The first, called fls3-1, has a frame shift mutation that causes an aberrant stop codon (V185stop, with reference to SEQ ID NO:2) and results in a truncated/nonfunctional FLS3 protein. The second variation, called fls3-2, encodes a full-length protein with four nonsynonymous amino acid changes, and these changes, specifically T1011P, results in 80% reduction of FLS3 activity. Additionally, an artificial version of FLS3 was generated that is functionally inactive (K877Q). FIGS. 2C-2D show experimental results demonstrating that FLS3 has overall similarity in domain architecture to FLS2. Comparative modeling was used to predict FLS3 structure based on the crystal structure of FLS2 (FIG. 2C). However, the proteins are only 35% identical at the amino acid level (FIG. 2D, showing amino acid sequence alignment of FLS2 (SEQ ID NO:6, top row) and FLS3 (SEQ ID NO:2, bottom row)). FIG. 2E shows experimental results where potential FLS3 orthologs were identified from sequenced accessions of potato and pepper (SEQ ID NOs:7-10), but not from *Nicotiana benthamiana* or *petunia*. Certain varieties of pepper and potato were previously shown to be sensitive to flgII-28 (Clarke et al., "Allelic Variation in Two Distinct *Pseudomonas syringae* Flagellin Epitopes Modulates the Strength of Plant Immune Responses But Not Bacterial Motility," New Phytol 200: 847-860 (2013), which is hereby incorporated by reference in its entirety), and it was found that the sequenced accessions were as well, whereas *Nicotiana benthamiana* and *petunia* were not. These observations suggest that the gene is likely to have arisen via a duplication event prior to the divergence of *Capsicum* from *Solanum*. FIG. 2F shows a sequence alignment (in plain text as well as shaded for amino acid similarity) between FLS3 from *Solanum lycopersicum* cv. 'Heinz 1706', *S. pimpinellifolium*, pepper (*Capsicum annum*), and potato (*S. tuberosum*) (SEQ ID NOs: 2, 4, 8, and 10), from which a conserved sequence of SEQ ID NO:11 (see below) is derived.

FIG. 3A shows experimental results demonstrating that expression of FLS3 in Yellow Pear protoplasts and subsequent treatment of 100 nM flgII-28 results in an increase of phosphorylated MAPKs similar to levels observed either with the control treatment 100 nM flg22, or with expression of the unrelated PRR EFR plus treatment with its cognate ligand 100 nM elf18. Activation via phosphorylation of these MAPKs is a hallmark of MAMP-related responses in plants. FIG. 3B shows experimental results demonstrating that transient expression of FLS3 in normally non-responsive *N. benthamiana* leaves followed by treatment with flgII-28 resulted in production of ROS; similar experiments using EFR and 100 nM elf18 functioned as controls. FIG. 3C shows experimental results demonstrating that plants silenced for BAK1 using VIGS have a reduced ROS response when expressing FLS3 and treated with 100 nM flgII-28 compared to control silenced plants; similar experiments using EFR and 100 nM elf18 functioned as controls. FIG. 3D shows experimental results demonstrating that FLS3 co-immunoprecipitated with BAK1 whereas the YFP control could not pull down FLS3, showing that FLS3 and BAK1 could physical associate in plant cells and indicating that FLS3 signaling occurs through a BAK1-dependent mechanism. FIG. 3E shows experimental results where LA1589 and F2 plants from the LA1589×Yellow Pear cross were infected with the bacterial pathogen *Pseudomonas cannabina* pv. *alisalensis* ES4326 (Pcal ES4326; formerly *P. syringae* pv. *maculicola*) at $3 \times 10^4$ CFU/mL and bacterial populations were measured 3 days after inoculation. Decreased bacterial growth was observed specifically in F2 plants that have a functional copy of FLS3 (FLS3/FLS3 or FLS3/fls3) similar to levels measured in LA1589 plants (FLS3/FLS3), suggesting that FLS3 confers increased resistance to bacterial infection.

FIGS. 4A-C illustrate the demonstration that FLS3 directly and specifically binds flgII-28. FIG. 4A shows an overview of the biochemical purification approach used to demonstrate binding. Modified peptides flg28* and flg22* were prepared that are decorated with an alkyne functional group and a trifluoromethyldiazirine photo-crosslinking moiety. Purified plasma membrane preparations from *N. benthamiana* leaves expressing FLS3-GFP were treated with flgII-28* or flg22* and subsequently UV-irradiated for photo-crosslinking. FLS3-GFP was then immunoprecipitated using the GFP tag and subsequently biotinylated via click chemistry. Binding was demonstrated using immunoblot analysis to detect biotin-labeled FLS3-flgII-28 complexes. FIG. 4B shows experimental results where only flgII-28*-treated, but not flg22*-treated, plasma membranes showed FLS3-GFP biotinylation. FIG. 4C shows experimental results demonstrating that co-treatment with a large excess (10-fold) of unmodified flgII-28 along with flgII-28* strongly reduced biotinylation of FLS3-GFP, indicating that unmodified flgII-28 and flgII-28* compete for the same binding site; however, addition of a 10-fold excess of flg22 along with flgII-28* did not prevent biotinylation of FLS3-GFP, indicating that flg22 does not compete with flgII-28* in binding to FLS3-GFP.

DETAILED DESCRIPTION OF THE INVENTION

Figure 1A:
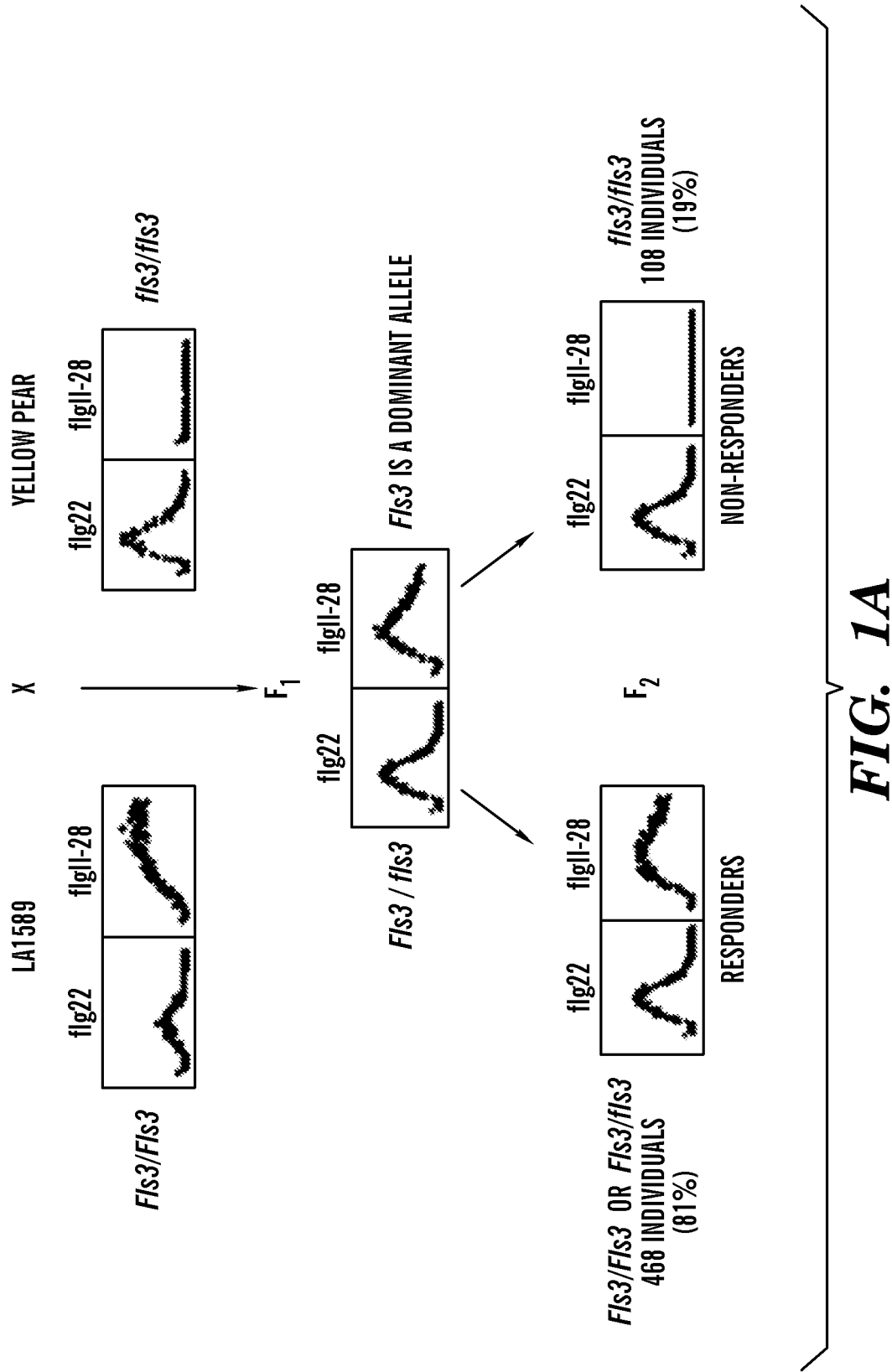
FIGS. 1A-1E illustrate the genetics approach used for identifying FLS3.

One aspect of the present invention relates to a nucleic acid construct that includes a nucleic acid molecule that encodes an FLS3 protein; a 5' heterologous DNA promoter sequence; and a 3' terminator sequence, where the nucleic acid molecule, the DNA promoter sequence, and the terminator sequence are operatively coupled to permit transcription of the nucleic acid molecule.

The nucleic acid molecule may (i) include the nucleotide sequence of SEQ ID NO:1, SEQ ID NO: 3, SEQ ID NO: 7, or SEQ ID NO: 9 and/or (ii) encode a polypeptide or protein having the amino acid sequence of SEQ ID NO:2, SEQ ID NO:4, SEQ ID NO:5, SEQ ID NO:8, or SEQ ID NO:10, as set forth below.

The coding sequence for FLS3 (Solyc04g009640, which is hereby incorporated by reference in its entirety) from *Solanum lycopersicum* cv. 'Heinz1706' (SEQ ID NO:1) is as follows:

```
ATGGAGAAACACATTTTCTTATTGATACTTGCTATCTTAGTTCAATTTT

ACTTTGTTTCTTCTATATCAGCTACTATTTCCTCAAATGAGACTGATCA

AGAAGCTCTACTAGCTTTTCGAAACCTTGTTACGAGTGATTCTAGTCAT

TTTTTAGCCAATAATTGGACAAAAAACACTTCATTTTGCTCTTGGTTTG

GTGTCACTTGTAGTCCAAAAAGGCAAAGGGTTGTAGCCTTGACTCTTCC

TAATTTGCAACTTCAAGGCACAATTTCGCCGTCTTTGGCCAATCTATCT

TTTCTCATAGAGCTAAATCTCGCAAACAACAACTTACACAGTGAAATCC

CTGATGGCATTGGCCGCTTGCCTCGTCTACGAGTGATTGATATTCAGAA
```

```
CAATCAGCTGCATGGAAGTATTCCAACAAGTCTATTTCAACACGGGAGT
GTTCAAATCATTTCATTGGCTTTCAATAAACTCGGTGGTGAAATGTGGA
ACGGTACATGGTATGTACCCGAACTCAGAGTCTTAAATCTCAGGAACAA
TACCATTACAGGTGTGATCCCTCCTTCTATTGGAAATGCCACAAAGTTG
ATGAACTTCAGTTTGAATGGGAATAGAATCAACGGCAACATTCCAATGG
AGATTGGTAATCTAAGCCAACTTGTTGAGTTGTCGTTGTCTCGTAATCA
ATTAACAGGTTCCATTCCTTCAACATTGTTTAATATCTCCTCCCTTCTC
GTCGTGTCTCTGGCATACAATAGCCTTTCAGGTCCTCTGTTTCCTGATG
ATCGACGTAACGTTCTTTCATCAAACCTCGAGCATATAGGTGTATCATA
CAATCAAATCACTGGTCACATTCCTTCCAACATCTGTCAATTCACAGCT
CTCAGAGTTCTGTCCATATCATACAACAACATAACTGGAGAAATACCGA
GAAATATTGGTTGTTTAGCCAAGCTCGAAGAGTTTTATATCGGTTATAA
TGCAATAAATGGAACAATTCCTGCTTCATTAGGCAATATTTCAACTCTT
CAAAATCTTCATTGCGGAAGCAATCACATGGAGGGAGAACTTCCTCCAG
AATTAGGAAAGCTATCAAACTTAAGACAAATCAATTTCGAAGAAAATTA
TAATCTTATTGGTGAAATTCCGAATACTATTTTCAACATATCTTCTTTG
GAGTTCATTGCTTTCACTTTCAACTACCTTTCAGGTAGAATTCCGAATC
TTCTTCACCTTCCAAATCTTATACAACTTCTCTTAGCAAACAATCAGCT
CGAAGGTGAAATTCCTCGGTACATCACAAATGCTACGAATCTTGAGCTG
TTAGAGCTATCAGATAACCTTCTCACAGGTACTATTCCTAATGATTTAG
GAAATCTTCGCGAGCTGCGAGATCTTTTCCTACATCATAATCAACTTAC
TGAGTTGGGATTCTTTGATTCTTTGGTGAAATGTAGGATGTTGAGATAT
GTACAAGTGGGATCGAATCCGTTGAATGATGTTCTGCCAAGTAGTATTG
GCAATCTTTCATCTACTGTTGAATACTTTCATATTGGAGATGCACAAAT
CAATGGATTCATTCCCACTAGTACAGGCAACATGACCGGTCTTACAACG
CTAGTTTTTCAAGATAACAGTTTGACAGGAAACATTCCTCGTGAGATCC
GTAAGCTTAAACAACTCCAAGGTTTATTTCTAGTTAACAATGGACTACA
GGGGGACATAGCAGAGGTAGTATGTGATTTATCGAATTTGGTTCGATTA
GCTCTGTCTGAAAATGAGCTCTCGGGGGTGATTCCGGAATGTTTAGGAA
ATCTTACCATGCTACAACAACTTTTTTAGGTTCTAACAAGTTTGAATC
AAAGCTACCTTTAAGCTTTTGGAAGATGAGTAGTCTTCTATATTTAAAC
ATGTCGCGTAATTCTATAAAGGGAGAAGTTCCATCAGATATCGGAGAAC
TTAAAGCTATTGTAGCAATCGATATCTCTGGTAACCATTTCTCGGGGTC
GATACCAAGCAATTTGGGGAACTTCAAACCTTGAAGTTACTTTCCTTA
TCGAACAATTCGTTTTCAGGTCCAATTCCATTTTCCTTTTCAAACTTGA
AAAGCTTGGAATTCTTGGATTTGTCTTTGAATAACTTGTCAGGTACTAT
TCCTAAGTCTTTCGAAAAGCTTTTGTACCTTACAAGCATCAACGTCTCG
TTTAATGTTTTAGAAGGTGAAATACCTAGTGGTGGTGTGTTTGCAAACT
CCACCCTGCAATCATTTAGTGGGAACAAAGGTCTATGTGGAAGGCAAAT
ATTGGAGGTTCCTGCTTGTGCTATCACTACTCCTGAACAACAACAATCA
AAATCGAAGAAGCTTGTGCTAAAAATTGTCACTCCGATGGTTATTTCAT
```
```
TCTTTCTGATATTCTTGTTGGTTGTCTCGATTTGGATAATGAAACGAAA
GAAGAAAGGGAAGTCCAAAGATGTTGAAAAGGTTCCGGAGATGAGGACT
TATCAATTGATTTCTTATCATGAGATTCAACGAGCAACTAACAATTTTG
ATGAATCCAATTTGATTGGCGTGGGAGGTTCTGGCTCTGTGTACAAAGC
CACATTAGCTAGTGGAATTGTGGTTGCAATTAAGGTACTGGATTTGGAA
AATGAGGAAGTATGCAAAGGTTTGATACTGAATGCGAAGTGATGAGAA
ATGTTAGACACAAAAACCTTGTTTCGGTGATCACTACGTGTTCTAGTGA
ACACATAAGAGCCTTTGTTCTGCAGTATATGCCCAACGGAAGTCTTGAC
AATTGGTTGTACAAAGAAGATCGCCACTTAAAACTTCGTCAAAGAGTCA
CCATAATGCTTGATGTAGCTATGGCAATTGAATATCTACATCATGGTAA
TGACACCCCAATAGTTCATTGTGACCTCAAGCCAGCCAACGTTCTTTTG
GATGAAGATATGGTGGCGTGTTGGTGATTTTGGCATCTCAAAGATTT
TAGCTGTAAGCAAATCCATGGCACATACAAAGACATTAGGCACTCTTGG
ATATATTGCACCAGAATATGGCTCGGAGGGAATAGTGTCCACTCGTGGT
GATGTTTACAGTTATGGCATCATGCTGATGGAGGTTTTGGCAAAAGAA
GGCCAACAGGTGAAGAGATATTCAACGAAAATCTTGGCTTGAGGGAGTG
GATAACGCGAGCATTTCCAAGAACTATGATGGAAGTTGTGGACGCGGAT
ATGTTTCATGATGGAGAAAAAATTACTTCCGAAAGTGAAATATGCATAC
TCTCCATGATAGAACTGGCTTTAGATTGCACAAAGGCAACACCAGAATC
AAGGATAACCATGAAAGATGTAGTCAAGAGGCTTAACAAAATAAAGAAC
ACATTTGGAAACATAGAAGTAAATTAG
```

The amino acid sequence for FLS3 from *S. lycopersicum* cv. 'Heinz1706' (SEQ ID NO:2) is as follows:

```
MEKHIFLLILAILVQFYFVSSISATISSNETDQEALLAFRNLVTSDSSHF
LANNWTKNTSFCSWFGVTCSPKRQRVVALTLPNLQLQGTISPSLANLSFL
IELNLANNNLHSEIPDGIGRLPRLRVIDIQNNQLHGSIPTSLFQHGSVQI
ISLAFNKLGGEMWNGTWYVPELRVLNLRNNTITGVIPPSIGNATKLMNFS
LNGNRINGNIPMEIGNLSQLVELSLSRNQLTGSIPSTLFNISSLLVVSLA
YNSLSGPLFPDDRRNVLSSNLEHIGVSYNQITGHIPSNICQFTALRVLSI
SYNNITGEIPRNIGCLAKLEEFYIGYNAINGTIPASLGNISTLQNLHCGS
NHMEGELPPELGKLSNLRQINFEENYNLIGEIPNTIFNISSLEFIAFTFN
YLSGRIPNLLHLPNLIQLLLANNQLEGEIPRYITNATNLELLELSDNLLT
GTIPNDLGNLRELRDLFLHHNQLTELGFFDSLVKCRMLRYVQVGSNPLND
VLPSSIGNLSSTVEYFHIGDAQINGFIPTSTGNMTGLTTLVFQDNSLTGN
IPREIRKLKQLQGLFLVNNGLQGDIAEVVCDLSNLVRLALSENELSGVIP
ECLGNLTMLQQLFLGSNKFESKLPLSFWKMSSLLYLNMSRNSIKGEVPSD
IGELKAIVAIDISGNHFSGSIPSNLGELQTLKLLSLSNNSFSGPIPFSFS
NLKSLEFLDLSLNNLSGTIPKSFEKLLYLTSINVSFNVLEGEIPSGGVFA
NSTLQSFSGNKGLCGRQILEVPACAITTPEQQQSKSKKLVLKIVTPMVIS
FFLIFLLVVSIWIMKRKKKGKSKDVEKVPEMRTYQLISYHEIQRATNNFD
```

ESNLIGVGGSGSVYKATLASGIVVAIKVLDLENEEVCKRFDTECEVMRNV

RHKNLVSVITICSSEHIRAFVLQYMPNGSLDNWLYKEDRHLKLRQRVTIM

LDVAMAIEYLHHGNDTPIVHCDLKPANVLLDEDMVARVGDFGISKILAVS

KSMAHTKTLGTLGYIAPEYGSEGIVSTRGDVYSYGIMLMEVLAKRRPTGE

EIFNENLGLREWITRAFPRTMMEVVDADMFHDGEKITSESEICILSMIEL

ALDCTKATPESRITMKDVVKRLNKIKNTFGNIEVN

The coding sequence for FLS3 from *S. pimpinellifolium* LA1589 (SEQ ID NO:3) is as follows:

ATGGAGAAACACATTTTCTTATTGATACTTGCTATCTTAGTTCAATTTTAC

TTTGTTTCTTCTATATCAGCTACTATTTCCTCAAATGAGACTGATCAAGAA

GCTCTACTAGCTTTTCGAAACCTTGTTACGAGTGATTCTAGTCATTTTTA

GCCAATAATTGGACAAAAAACACTTCATTTTGCTCTTGGTTTGGTGTCACT

TGTAGTCCAAAAAGGCAAAGGGTTGTAGCCTTGACTCTTCCTAATTTGCAA

CTTCAAGGCACAATTTCGCCGTCTTTGGCCAATCTATCTTTTCTCATAGGG

CTAAATCTCGCGAACAACAACTTACACAGTGAAATCCCTGATGGCATTGGC

CGCTTGCCTCGTCTACGAGTGATTGATATTCAGAACAATCAGCTGCATGA

AGTATTCCAACAAGTCTATTTCAACACGGGAGTGTTCAAATCATTTCATTG

GCTTTCAATAAACTCGGTGGTGAAATGTGGAACGGTACATGGTATGTACCC

GAACTCAGAGTCTTAAATCTCAGGAACAATACCATTACAGGTGTGATCCCT

CCTTCTATTGGAAATGCCACAAAGTTGATGAACTTCAGTTTGAATGGGAAT

AGAATCAACGGCAACATTCCAATGGAGATTGGTAATCTAAGCCAACTTGTT

GAGTTATCGTTGTCTCGTAATCAATTAACAGGTTCCATTCCTTCAACATTG

TTTAATATCTCCTCCCTTCTCGTCGTGTCTCTGGCATACAATAGCCTTTCA

GGTCCTCTGTTTCCTGATGATCGACGTAACGTTCTTTCATCAAACCTCGAG

CATATAGGTGTATCATACAATCAAATCACTGGTCACATTCCTTCCAACATC

TGTCAATTCACAGCTCTCAGAGTTCTGTCCATATCATACAACAACATAACT

GGAGAAATACCGAGAAATATTGGTTGTTTAGCCAAGCTCGAAGAGTTTTAT

ATCGGTTATAATGCAATAAATGGAACAATTCCTGCTTCATTAGGCAATATT

TCAACTCTTCAAAATCTTCATTGCGGAAGCAATCACATGGAGGGAGAACTT

CCTCCGGAATTAGGAAAGCTATCAAACTTAAGACAAATCAATTTCGAAGAA

AATTATAATCTTATTGGTGAAATTCCGAATACTATTTTCAACATATCTTCT

TTGGAGTTCATTGCTTTCACTTTCAACTACCTTTCAGGTAGAATTCCGAAT

CTTCTTCACCTTCCAAATCTTATACAACTTCTCTTAGCAAACAATCAGCTC

GAAGGTGAAATTCCTCGGTACATCACAAATGCTACGAATCTTGAGCTGTTA

GAGCTATCAGATAACCTTCTCACAGGTACTATTCCTAATGATTTAGGAAAT

CTTCGCGAGCTGCGAGATCTTTTCCTACATCATAATCAACTTACTGAGTTG

GGATTCTTTGATTCTTTGGTGAAATGTAGGATGTTGAGATATGTACAAGTG

GGATCGAATCCGTTGAATGATGTTCTGCCAAGTAGTATTGGCAATCTTTCA

TCTACTGTTGAATACTTTCATATTGGAGATGCACAAATCAATGGATTCATT

CCCACTAGTACAGGCAACATGACCGGTCTTACAACGCTAGTTTTTCAAGAT

AACAGTTTGACAGGAAACATTCCTCGTGAGATCGGTAAGCTTAAACAACTC

CAAGGTTTATTTCTAGTTAACAATGGACTACAGGGGGACATAGCAGAGGTA

GTATGTGATTTATCGAATTTGGTTCGATTAGCTCTGTCTGAAAATGAGCTC

TCGGGGGTGATTCCGGAATGTTTAGGAAATCTTACCATGCTACAACAACTT

TTTTTAGGTTCTAACAAGTTTGAATCAAAGCTACCTTTAAGCTTTTGGAAG

ATGAGTAGTCTTCTCTATTTAAACATGTCGCGTAATTCTATAAAGGGAGAA

GTTCCATCAGATATCGGAGAACTTAAAGCTATTGTAGCAATCGATATCTCT

GGTAACCATTTCTCGGGGTCGATACCAAGCAATTTGGGGGAACTTCAAACC

TTGAAGTTACTTTCCTTATCGAACAATTCGTTTTCAGGTCCAATTCCATTT

TCCTTTTCAAACTTGAAAAGCTTGGAATTCTTGGATTTGTCTTTGAATAAC

TTGTCAGGTACTATTCCTAAGTCTTTCGAAAAGCTTTTGTACCTTACAAGC

ATCAACGTCTCGTTTAATGTTTTAGAAGGTGAAATACCTAGTGGTGGTGTG

TTTGCAAACTCCACCCTGCAATCATTTAGTGGGAACAAAGGTCTATGTGGA

AGGCAAATATTGGAGGTTCCTGCTTGTGCTATCACTACTCCTGAACAACAA

CAATCAAAATCGAAGAAGCTTGTGCTAAAAATTGTCACTCCGATGGTTATT

TCATTCTTTCTGATATTCTTGTTGGTTGTCTCGATTTGGATAATGAAACGA

AAGAAGAAAGGGAAGTCCAAAGATGTTGAAAAGGTTCCGGAGATGAGGACT

TATCAATTGATTTCTTATCATGAGATTCAACGAGCAACTAACAATTTTGAT

GAATCCAATTTGATTGGCGTGGGAGGTTCTGGCTCTGTGTACAAAGCCACA

TTAGCTAGTGGAATTGTGGTTGCAATTAAGGTACTGGATTTGGAAAATGAG

GAAGTATGCAAAAGGTTTGATACTGAATGCGAAGTGATGAGAAATGTTAGA

CACAAAAACCTTGTTTCGGTGATCACTACGTGTTCTAGTGAACACATAAGA

GCCTTTGTTCTGCAGTATATGCCCAACGGAAGTCTTGACAATTGGTTGTAC

AAAGAAGATCGCCACTTAAAACTTCGTCAAAGAGTCACCATAATGCTTGAT

GTAGCTATGGCAATTGAATATCTACATCATGGTAATGACACCCCAATAGTT

CATTGTGACCTCAAGCCAGCCAACGTTCTTTTGGATGAAGATATGGTGGCG

CGTGTTGGTGATTTTGGCATCTCAAAGATTTTAGCTGTAAGCAAATCCATG

GCACATACAAAGACATTAGGCACTCTTGGATATATTGCACCAGGTATATAT

ACTACTATACTAGTCTCTTTCCATTTCATTTATGTATCGAAGACCTTTCGT

TATTGTTATATCAGATGAGTATTTGAGTAATACTTTTTTTCATTTTCGTTC

TTTTAAGAATATGGCTCGGAGGGAATAGTGTCCACTCGTGGTGATGTTTAC

AGTTATGGCATCATGCTGATGGAGGTTTTGGCAAAAAGAAGGCCAACAGGT

GAAGAGATATTCAACGAAAATCTTGGCTTGAGGGAGTGGATAACGCGAGCA

TTTCCAAGAACTATGATGGAAGTTGTGGACGCGGATATGTTTCATGATGGA

GAAAAAATTACTTCCGAAAGTGAAATATGCATACTCTCCATGATAGAACTG

GCTTTAGATTGCACAAAGGCAACACCAGAATCAAGGATAACCATGAAAGAT

GTAGTCAAGAGGCTTAACAAAATAAAGAACACATTTGGAAACATAGAAGTA

AATTAG

The amino acid sequence for FLS3 from *S. pimpinellifolium* LA1589 (SEQ ID NO:4) is as follows:

MEKHIFLLILAILVQFYFVSSISATISSNETDQEALLAFRNLVTSDSSHF
LANNWTKNTSFCSWFGVTCSPKRQRVVALTLPNLQLQGTISPSLANLSFL
IGLNLANNNLHSEIPDGIGRLPRLRVIDIQNNQLHGSIPTSLFQHGSVQI
ISLAFNKLGGEMWNGTWYVPELRVLNLRNNTITGVIPPSIGNATKLMNFS
LNGNRINGNIPMEIGNLSQLVELSLSRNQLTGSIPSTLFNISSLLVVSLA
YNSLSGPLFPDDRRNVLSSNLEHIGVSYNQITGHIPSNICQFTALRVLSI
SYNNITGEIPRNIGCLAKLEEFYIGYNAINGTIPASLGNISTLQNLHCGS
NHMEGELPPELGKLSNLRQINFEENYNLIGEIPNTIFNISSLEFIAFTFN
YLSGRIPNLLHLPNLIQLLLANNQLEGEIPRYITNATNLELLELSDNLLT
GTIPNDLGNLRELRDLFLHHNQLTELGFFDSLVKCRMLRYVQVGSNPLND
VLPSSIGNLSSTVEYFHIGDAQINGFIPTSTGNMTGLTTLVFQDNSLTGN
IPREIGKLKQLQGLFLVNNGLQGDIAEVVCDLSNLVRLALSENELSGVIP
ECLGNLTMLQQLFLGSNKFESKLPLSFWKMSSLLYLNMSRNSIKGEVPSD
IGELKAIVAIDISGNHFSGSIPSNLGELQTLKLLSLSNNSFSGPIPFSFS
NLKSLEFLDLSLNNLSGTIPKSFEKLLYLTSINVSFNVLEGEIPSGGVFA
NSTLQSFSGNKGLCGRQILEVPACAITTPEQQQSKSKKLVLKIVTPMVIS
FFLIFLLVVSIWIMKRKKKGKSKDVEKVPEMRTYQLISYHEIQRATNNFD
ESNLIGVGGSGSVYKATLASGIVVAIKVLDLENEEVCKRFDTECEVMRNV
RHKNLVSVITICSSEHIRAFVLQYMPNGSLDNWLYKEDRHLKLRQRVTIM
LDVAMAIEYLHHGNDTPIVHCDLKPANVLLDEDMVARVGDFGISKILAVS
KSMAHTKTLGTLGYIAPEYGSEGIVSTRGDVYSYGIMLMEVLAKRRPTGE
EIFNENLGLREWITRAFPRTMMEVVDADMFHDGEKIISESEICILSMIEL
ALDCTKATPESRITMKDVVKRLNKIKNTFGNIEVN*

A conserved amino acid sequence for FLS3 from *S. pimpinellifolium* and *S. lycopersicum* cv. 'Heinz 1706' (SEQ ID NO:5) is as follows:

MEKHIFLLILAILVQFYFVSSISATISSNETDQEALLAFRNLVTSDSSHF
LANNWTKNTSFCSWFGVICSPKRQRVVALTLPNLQLQGTISPSLANLSFL
I[E/G]LNLANNNLHSEIPDGIGRLPRLRVIDIQNNQLHGSIPTSLFQHG
SVQIISLAFNKLGGEMWNGTWYVPELRVLNLRNNTITGVIPPSIGNATKL
MNFSLNGNRINGNIPMEIGNLSQLVELSLSRNQLTGSIPSTLFNISSLLV
VSLAYNSLSGPLFPDDRRNVLSSNLEHIGVSYNQITGHIPSNICQFTALR
VLSISYNNITGEIPRNIGCLAKLEEFYIGYNAINGTIPASLGNISTLQNL
HCGSNHMEGELPPELGKLSNLRQINFEENYNLIGEIPNTIFNISSLEFIA
FTFNYLSGRIPNLLHLPNLIQLLLANNQLEGEIPRYITNATNLELLELSD
NLLTGTIPNDLGNLRELRDLFLHHNQLTELGFFDSLVKCRMLRYVQVGSN
PLNDVLPSSIGNLSSTVEYFHIGDAQINGFIPTSTGNMTGLTTLVFQDNS
LTGNIPREI[R/G]KLKQLQGLFLVNNGLQGDIAEVVCDLSNLVRLALSE
NELSGVIPECLGNLTMLQQLFLGSNKFESKLPLSFWKMSSLLYLNMSRNS
IKGEVPSDIGELKAIVAIDISGNHFSGSIPSNLGELQTLKLLSLSNNSFS
GPIPFSFSNLKSLEFLDLSLNNLSGTIPKSFEKLLYLTSINVSFNVLEGE
IPSGGVFANSTLQSFSGNKGLCGRQILEVPACAITTPEQQQSKSKKLVLK
IVTPMVISFFLIFLLVVSIWIMKRKKKGKSKDVEKVPEMRTYQLISYHEI
QRATNNFDESNLIGVGGSGSVYKATLASGIVVAIKVLDLENEEVCKRFDT
ECEVMRNVRHKNLVSVITTCSSEHIRAFVLQYMPNGSLDNWLYKEDRHLK
LRQRVTIMLDVAMAIEYLHHGNDTPIVHCDLKPANVLLDEDMVARVGDFG
ISKILAVSKSMAHTKTLGTLGYIAPEYGSEGIVSTRGDVYSYGIMLMEVL
AKRRPTGEEIFNENLGLREWITRAFPRTMMEVVDADMFHDGEKITSESEI
CILSMIELALDCTKATPESRITMKDVVKRLNKIKNTFGNIEVN

The coding sequence for FLS3 (CA05g03880, which is hereby incorporated by reference in its entirety) from pepper (*Capsicum annum*) (SEQ ID NO:7) is as follows:

ATGGAGAAACACATTTTCTTATTGATACTTCTCTTCCTAGTTCAAGTTTA
CGCTGTTGCGTCGATATTGGTTACTTCCTCTAATGAAACAGACCAAGAGG
CTCTACTAGCTTTTCGAAATCTTATTAGAAGTGATTCTAGTCATTTTTTG
GCTAATAATTGGACCAAGAATAGTACTTCATTTTGCTCTTGGTTCGGTGT
CACTTGTAGTCCCAGAAGGCAAAGGGTTGTGGCCTTGAATCTTCCGGATT
TGCAACTTCCAGGCACAATTTCGCCGTCCTTGGCCAATTTGTCCTTTCTC
AGGGAGCTCAATCTTGGAAACAACAGCTTCCACGGTAACATCCCTTATGG
CATAGGCAACTTGCCTCGCTTGCGAGTGATTGATATTCAAAACAACCAGC
TCCAAGGAAGTATTCCAGCAAGTCTATTTCAACACCAAAGAGTTCAAATC
ATTTCATTGGCTTTCAATAAACTCAGTGGTGAAATGTGGAACGGTACATG
GTATGTACCGGAACTCAGAGTCTTAAATCTCAGGAACAATACTCTCACCG
GGAGAATCCCTCCTTCTATTGGAAATGCCACAAAATTGATGAACTTCAGT
TTGCATGGGAATAGAATCAGTGGCAATATTCCAAAGGAAATTGGTAATCT
GAGCCAACTTGCAGAGCTGTTCTTGTCGCGTAACCAGTTGACAGGTTCCA
TTCCCACAACATTGTTTAATATCTCTTCCCTTCTTGTCGCGTCTCTGGCA
TTTAATAGCCTTTCTGGTCCTCTCTTGCTTGGTGAAGGCAATATTTTATC
AAATCTCGAGCATCTAGGTATGTCTTACAATAAATTTCTGGTCGCATTCC
TTCCAACATCTGTCAACTCAAAGAGCTCAAAGTTTTGTCCATATCTTTCA
ACAACATAACTGGGGAAATGCCCAGAAATGTTGGTTGTTTAACCAAGCTC
GAGGAGTTGTATATTGGTTATAATCCAATAAATGGTAGAATTCCTACCTC
ATTGGGCAATATTTCCACTCTGCAAAAACTTCATTGTGGAAATAATAGCA
TGATTGGGGAAATTCCTCCGGAATTGGGGAAGCTATCAAATTTAAGAGAA
ATAGATTTTTCAGAAAATTATAATCTTACAGGTGAGATTCCAAATTCTAT
TTTCAACATATCTTCGTTGGAATTTATTGTTTTCAGTTTCAACTACCTCT
CAGGTAGGATTCCGGTTCTTCTTCATTTTCCAAACCTTATACAACTTTTC
TTGGCAAACAATCAGCTCGAAGGGGAAATTCCTCGGTACATAACAAATGC
TACAAAGCTTGAGTCATTGGACCTATCAGTAAACCGTCTCACGGGCACCA

-continued

TTCCTAATAATTTAGGAAATCTTCGCAAGCTGAAACAACTGTTCCTTCAT
CATAATCAACTTATTGAGTTGGGATTCTTCGATTCTTTGGTGAATTGTAG
GATGTTGCAATATGTACAAGTGGGATCGAATCCATTGAATGGAGTTTTGC
CCAGTAGTATTGGAAATCTTTCGTCTAATGTTGAATACTTTCATATTGGA
GATGCACAAATCAGTGGATTCATTCCCACTAGTACAGGCAACATGAGCGG
TCTTACAACCTTAGTTTTTCAAGATAACAACTTGACCGGAAATATTCCTC
GTGAGATCGGTAGGCTTAAACAACTCCAAGGTCTATTTCTAATTAACAAT
GAACTACAGGGGGATATTACGGCCGGTAGTATGTGATTTATCTAATTTGGT
TCGATTAAGTCTATCTGATAATGAGCTCTCCGGGGTGATTCCAAATTGTA
TAGGGAATCTTAGCATGCTGCAACAACTTTTTTTGGGTTCTAACAATTTT
GGATCAGAGCTTCCTTTAAGCATTTGGAAGATGAGAGGTTTACTCTTTGT
AAACATTTCGCTAAATTCTCTAGAGGGAGAAGTTCCATCAGATATCGGAG
AACTTAAAGCCATTGTAGAGATCGATATTTCTGGTAACCACTTTTCAGGG
ATGATACCAAGCAATTTGGGTGAACTCCAAAATTTGCAGTTACTTTCCCT
ATCGAACAATTCATTTTCAGGTCCAATTCCATTATCCTTTTCAAACTTGA
TAAGCTTGGAGATCTTGGATTTGTCTTTAAATAACTTGTCAGGTACTATT
CCTAAGTCTTTTGAAAAGCTCTCATACCTTCAAAGCATCAATGTTTCGTT
TAATGCTTTAGAGGGTGAAATACCTAGTGGTGGTGTGTTTGCGAATTCCA
CTCTGCAATCATTTCTTGGGAACAAAGGTCTTTGTGGAAGGAACATATCG
GAGGTTCCTGCTTGTGCTATTACTAATCCTGAACAACAAGCAAAATCTAA
GAAGCTTGCACTGAAAATTGTTACTCTGGTAGTTATTTCATTCTTTCTGA
TATTGTTGTTGGTCATCTCAATTTGGATAAAGAAACGAAAGAAGAATGGG
AAGTCCAAAGATGTTGAAAAGGTTCCAGAGATGAGGACTTATCAATTGAT
TTCTTATCATGAGATTCAACGAGCAACAAATAATTTTGATGGATCCAATT
TAATTGGCGTGGGCGGTTCTGGCTCTGTGTACAAAGGCACATTGCCGAGC
GGAATTGTGGTTGCAATAAAGGTTCTGGATTTGCATCATGAGGAAGTATG
CAAAAGGTTTGACACTGAATGTGAAGTGATGAGAAATGTTAGACATAAAA
ATATTGTTTCGGTGATCACTACGTGCTCAAGCCAACACATACGAGCCTTT
GTTCTGCAATATATGCCCAATGGAAGTCTTGACAATTGGTTGTACAAAGA
AGATCGCCACTTAAACCTTCTTCAAAGAGTTACCATAATGCTTGACACAG
CCATGGCAATTGAATATCTACATCATGGTAATGACACCCAAATAGTTCAT
TGTGATCTAAAGCCAGCCAACGTTCTTTTGGATGATGATATGGTGGCTCA
TGTAGGTGATTTTGGCATCTCTAAGATTTTAGCAGTAAGCAAGTTCATGT
CACATACAAAGACATTGGGCACTCTTGGATATATTGCACCAGAATATGGC
TCGGAGGGAATAGTGTCTACTAGTGGTGATGTTTACAGTTATGGCATCAT
GTTGATGGAAGTTTTGGCAAAAAGAAGGCCAACAGATGAAGAGATATCCA
ATGAAAATCTTGGCTTGAGGGAGTGGATAACGCGAGCATTTCCAAGAACT
ATAATGGAAGTTGTGGATGCTGATATTTTTCATGATGAGGAAATATCGC
TTCGAAAAGTGAAATCTGCATACTTTCCATGATGAAGTGGCTTTGGATT
GCACAAAGGAAATGCCGGAATCTAGAATGACCATGAATGATGTAGTCAAG

-continued

AGGCTTTACAAAATTAAGAACACATTTATGGAAACGGAGAAGTTAGTGTGA

The amino acid sequence for FLS3 from pepper (*Capsicum annum*) (SEQ ID NO:8) is as follows:

MEKHIFLLILLFLVQVYAVASILVTSSNETDQEALLAFRNLIRSDSSHFL
ANNWTKNSTSFCSWFGVTCSPRRQRVVALNLPDLQLPGTISPSLANLSFL
RELNLGNNSFHGNIPYGIGNLPRLRVIDIQNNQLQGSIPASLFQHQRVQI
ISLAFNKLSGEMWNGTWYVPELRVLNLRNNTLTGRIPPSIGNATKLMNFS
LHGNRISGNIPKEIGNLSQLAELFLSRNQLTGSIPTTLFNISSLLVASLA
FNSLSGPLLLGEGNILSNLEHLGMSYNQISGRIPSNICQLKELKVLSISF
NNITGEMPRNVGCLTKLEELYIGYNPINGRIPTSLGNISTLQKLHCGNNS
MIGEIPPELGKLSNLREIDFSENYNLTGEIPNSIFNISSLEFIVFSFNYL
SGRIPVLLHFPNLIQLFLANNQLEGEIPRYITNATKLESLDLSVNRLTGT
IPNNLGNLRKLKQLFLHHNQLIELGFFDSLVNCRMLQYVQVGSNPLNGVL
PSSIGNLSSNVEYFHIGDAQISGFIPTSTGNMSGLTTLVFQDNNLTGNIP
REIGRLKQLQGLFLINNELQGDITAVVCDLSNLVRLSLSDNELSGVIPNC
IGNLSMLQQLFLGSNNFGSELPLSIWKMRGLLFVNISLNSLEGEVPSDIG
ELKAIVEIDISGNHFSGMIPSNLGELQNLQLLSLSNNSFSGPIPLSFSNL
ISLEILDLSLNNLSGTIPKSFEKLSYLQSINVSFNALEGEIPSGGVFANS
TLQSFLGNKGLCGRNISEVPACAITNPEQQAKSKKLALKIVTLVVISFFL
ILLLVISIWIKKRKKNGKSKDVEKVPEMRTYQLISYHEIQRATNNFDGSN
LIGVGGSGSVYKGTLPSGIVVAIKVLDLHHEEVCKRFDTECEVMRNVRHK
NIVSVITTCSSQHIRAFVLQYMPNGSLDNWLYKEDRHLNLLQRVTIMLDT
AMAIEYLHHGNDTQIVHCDLKPANVLLDDDMVAHVGDFGISKILAVSKFM
SHTKTLGTLGYIAPEYGSEGIVSTSGDVYSYGIMLMEVLAKRRPTDEEIS
NENLGLREWITRAFPRTIMEVVDADIFHDEENIASKSEICILSMIEVALD
CTKEMPESRMTMNDVVKRLYKIKNTFMETEKLV

The coding sequence for FLS3 (Sotub04g009590 or PGSC0003DMT400041350, each of which is hereby incorporated by reference in its entirety) from potato (*Solanum tuberosum* group phureja DM1-3) (SEQ ID NO:9) is as follows:

ATGGAGAAACACATTTTCTTATTGATACTTGCTATCTTAGTTCAATTTT
ACTTTGTTTCTTCTATATCAGCTACTATTTTCTCAAATGAGACTGATCA
AGAAGCTCTATTAGCTTTTCGAAATCTTGTACGAGTGATTCTAGTCAAT
TTTTAGCCAATAATTGGACCAAAAATACTTCATTTTGCTCTTGGTTTGG
TGTCACTTGTAGTCCAAAAAGGCAAAGGGTTGTAGCCTTGACTCTTCCT
AATTTGCAACTTCAAGGCACAATTTCGCCTTCTTTGGCCAATCTATCCT
TTCTCATAGAGCTAAATCTCACGAACAACAACTTCCATGGTAACATCCC
TTATGGCATTGGCCACTTGCCTCGTTTACGAGTGATTGATATTCAGAAC
AACCAGCTCCAAGGTAGTATTCCAACAAGTCTATTTCAACACCGGAGTG

-continued

```
TTCAAATCATTTCATTGGCTTTCAATAAACTCGGTGGTGAAATGTGGAA

CGGTACATGGTATGTACCGGAACTCAGAGTCTTAAATCTCAGGAACAAT

ACCATCACAGGTAGAATCCCTCCTTCTATTGGAAATGCCACAAAGTTGA

TGAACATCAGTTTGAATTGGAATAGAATCAACGGCAACATTCCAATGGA

GATCGGTAATCTAAGCCAACTTGTAGAGTTGTCGTTGTCTCGTAATCAA

TTAACAGGTTCCATTCCTTCAACATTGTTTAATATCTCCTCCCTTCTCG

TCGTGTCTCTGGCATACAATAGCCTTTCAGGTCCTCTGTTTCTTGATGA

TCGACGTAATGTTCTTTCATCAAACCTCGAGCATATAGGTGTATCATAC

AATCAAATCACTGGTCACATTTCTTCCAACATCTGCCAATTCAAAGCTC

TCAAAGTCTTGTCCATATCATACAACAACATAACTGGAGAAATACCGAG

AAATATTGGTTGTTTAGCCAAGCTCGAAGAGCTTTATATCGGTTATAAT

GCAATAGATGGAACAATTCCTACTTCATTAGGCAATATTTCCACTCTTC

AAAAACTTCATTGTGGAAACAATCACATGGAGGGAGAACTTCCTCCGGA

ATTAGGAAAGCTATCAAACTTAAGACAAATCAATTTCGAAGAAAATTAT

AATCTTATAGGTGAAATTCCAAATGCTATTTTCAACATATCTTCTTTGG

AATTCATTGCTTTCACTTTCAACTACCTCTCAGGTAGAATTCCAAATCT

TCTTCATCTTCCAAACCTTATACAACTTCTCTTAGCAAACAATCAGCTC

GAAGGTGAAATTCCTCGGTACATCACAAATGCTACCAATCTTGAGCTAT

TGGAACTATCAGATAACCTTCTCACAGGCAGTATTCCTTATGATTTAGG

AAATCTTCGCGAGCTGCAAGAACTTTTCCTACATCATAATCAACTTACT

GAGTTGGGATTCTTTGATTCTTTGGTGAAATGTAGGATGTTGAGATATG

TACAAGTGGGATCGAATCCGTTGAATGGTGTTCTGCCAAGTAGTATTGG

CAATCTTTCATCTACTGTTAATACTTTCATATTGGAGATGCACAAATC

AATGGATTCATTCCCACTAGTACAGGCAACATGAGTGGTCTTACAACGC

TAGTTCTTCAAGATAACAATTTGACAGGAAACATTCCTCGTGAGATCGG

TAAGCTTAAACAACTCCAAGGTTTATTTCTAGTTAACAATGAACTGCAG

GGGGATATAGCAGAGGTAGTATGTGATTTATCGAATTTGGTTCGATTAG

CTCTGTCTGAAAATGAGCTCTCGGGGGTGATTCCGGAATGTCTAGGAAG

TCTTACCATGCTACAACACCTTTTTTAGGTTCTAACAAGTTTGAATCA

AAGCTTCCTTTAAGCTTTTGGAAGATGAGTAGTCTTCTCTATGTAAACA

TGTCGCGTAATTCTATAGAGGGAGAAGTTCCATCAGATATCGGAGAACT

TAAAGCTATTGTAGCAATTGAAATCTCTGGTAACCACTTTTCGGGGATG

ATACCAAGCAATTTGGGGGAACTTCAAAACTTGAAGTTACTTTCCTTAT

CGAACAATTCGTTTTCAGGTCCAATTCCATTATCCTTTTCAAACTTGAA

AAGCTTGGAATTCTTGGATTTGTCTTTGAATAACTTGTCAGGTACTATT

CCTAAGTCTTTCGAAAAGCTTTTGTACCTTACAAGCATCAACGTCTCGT

TTAATGTTTAGAAGGTGAAATACCTAGTGGTGGTGTGTTTGCAAACTC

CACCCTGCAATCATTTCGCGGGAACAAAGGTCTATGTGGAAGGCAAATA

TTGGAGGTTCCTGCTTGTGCTGTCACTACTCCTGAACAACAACAACCAA

AATCGAAGAGGCTTGTGCTAAAAATTGTCACTCCGGTGGTTATTTCATT
```

-continued

```
CTTTCTGATATTCTTGTTGGTTGTCTCAATTTGGATAATGAAACGAAAG

AAGAAAGGAAAGTCCAAAGATATTGAAAAGGTTCCGGAGATGAGGACTT

ATCAATTGATTTCTTATCATGAGATTCAACGAGCAACAAACAATTTTGA

TGAATCCAATTTGATTGGCGTGGGAGGTTCTGGCTCTGTGTACAAAGCC

ACATTACCTAGTGGAATTGTGGTTGCAATAAAGGTACTGGATTTGGAAA

ATGAGGAAGTATGCAAAAGGTTTGATACTGAATGTGAAGTGGTGAGAAA

TGTTAGACACAGAAATCTTGTTTCGGTGATCACTACGTGTTCTAGTGAT

CACATAAGAGCCTTCGTTCTGCAATATATGCCCAACGGAAGTCTTGACA

ATTGGTTGTACAAAGAAGATCGCCACTTAAACCTTCGTCAAAGAGTCAC

CATAATGCTTGATGTAGCTATGGCAATTGAATATCTACATCATGGTAAT

GACACCCCTATAGTTCATTGTGACCTCAAGCCAGCCAACGTTCTTTTGG

ATGAAGATATGGTGGCGCGTGTTGGTGATTTTGGCATCTCAAAGATTTT

AGCTGTAAGCAAGTCTATGGCACATACAAAGACATTAGGCACTCTTGGA

TATATTGCACCAGAATATGGCTCGGAGGGAATAGTGTCCACTCGTGGTG

ATGTTTACAGTTATGGCATCATGTTGATGGAGGTTTTGGCAAAAAGAAG

GCCAACAGGTGAAGAGATATTCAACGAAAATCTTGGTTTGAGGGAGTGG

ATAACGCGAGCATTTCCAAGAACTATGATGGAAGTTGTGGACGCGGATA

TTTTTCATGATGGAGAAAAAATCACTTCCAAAAGTGAACTCTGCATACT

TTCCATGATAGAACTGGCTTTAGATTGCACAAAGGCAACACCAGAATCA

AGGATAACCATGAAAGATGTAGTCAAGAGGCTTAACAAAATTAAGAACA

CATTTTTGGAAACGTAGAAGTTAGTTAG
```

The amino acid sequence for FLS3 from potato (*Solanum tuberosum* group phureja DM1-3) (SEQ ID NO:10) is as follows:

```
MEKHIFLLILAILVQFYFVSSISATIFSNETDQEALLAFRNLVTSDSSQF

LANNWTKNTSFCSWFGVTCSPKRQRVVALTLPNLQLQGTISPSLANLSFL

IELNLTNNNFHGNIPYGIGHLPRLRVIDIQNNQLQGSIPTSLFQHRSVQI

ISLAFNKLGGEMWNGTWYVPELRVLNLRNNTITGRIPPSIGNATKLMNIS

LNWNRINGNIPMEIGNLSQLVELSLSRNQLTGSIPSTLFNISSLLVVSLA

YNSLSGPLFLDDRRNVLSSNLEHIGVSYNQITGHISSNICQFKALKVLSI

SYNNITGEIPRNIGCLAKLEELYIGYNAIDGTIPTSLGNISTLQKLHCGN

NHMEGELPPELGKLSNLRQINFEENYNLIGEIPNAIFNISSLEFIAFTFN

YLSGRIPNLLHLPNLIQLLLANNQLEGEIPRYITNATNLELLELSDNLLT

GSIPYDLGNLRELQELFLHHNQLTELGFFDSLVKCRMLRYVQVGSNPLNG

VLPSSIGNLSSTVEYFHIGDAQINGFIPTSTGNMSGLTTLVLQDNNLTGN

IPREIGKLKQLQGLFLVNNELQGDIAEVVCDLSNLVRLALSENELSGVIP

ECLGSLTMLQHLFLGSNKFESKLPLSFWKMSSLLYVNMSRNSIEGEVPSD

IGELKAIVAIEISGNHFSGMIPSNLGELQNLKLLSLSNNSFSGPIPLSFS

NLKSLEFLDLSLNNLSGTIPKSFEKLLYLTSINVSFNVLEGEIPSGGVFA

NSTLQSFRGNKGLCGRQILEVPACAVTTPEQQQPKSKRLVLKIVTPVVIS

FFLIFLLVVSIWIMKRKKKGKSKDIEKVPEMRTYQLISYHEIQRATNNFD
```

-continued

```
ESNLIGVGGSGSVYKATLPSGIVVAIKVLDLENEEVCKRFDTECEVVRNV

RHRNLVSVITTCSSDHIRAFVLQYMPNGSLDNWLYKEDRHLNLRQRVTIM

LDVAMAIEYLHHGNDTPIVHCDLKPANVLLDEDMVARVGDFGISKILAVS

KSMAHTKTLGTLGYIAPEYGSEGIVSTRGDVYSYGIMLMEVLAKRRPTGE

EIFNENLGLREWITRAFPRTMMEVVDADIFHDGEKIISKSELCILSMIEL

ALDCTKATPESRITMKDVVKRLNKIKNTFLET
```

A conserved amino acid sequence for FLS3 from *S. lycopersicum* cv. 'Heinz 1706', *S. pimpinellifolium*, pepper, and potato (SEQ ID NO:11) (see FIG. 2F, where "_" is shown below for gaps) is as follows:

```
MEKHIFLLIL[A/L][I/F]LVQ[F/V]Y[F/A]VSSI[S/L][A/V]

[T/_][/T][S/F]SNETDQEALLAFRNL[V/I][R/T]SDSS[H/Q]

FLANNWTKN[S/_]TSFCSWFGVTCSP[K/R]RQRVVAL[T/N]LP

[N/D]LQL[Q/P]GTISPSLANLSFL[I/R][E/G]LNL[A/G/T]NN

[N/S][L/F]H[S/G][E/N]IP[D/Y]GIG[R/N/H]RLPRLRVIDIQ

NNQL[H/Q]GSIP[T/A]SLFQH[G/Q/R][S/R]VQIISLAFNKL

[G/S]GEMWNGTWYVPELRVLNLRNNT[I/L]TG[V/R]IPPSIGNATK

LMN[F/I]SL[N/H][G/W]NRI[N/S]GNIP[M/K]EIGNLSQL

[V/A]EL[S/F]SRNQLTGSIP[/T]TLFNISSLLV[V/A]SLA

[Y/F]NSLSGPL[F/L][P/L][D/G][D/E][R/G][R/_][N/_]

[V/N][L/I][S/L]SNLEH[I/L]G[V/M]SYNQI[T/S]G[H/R]I

[P/S]SNICQ[F/L][T/K][A/E]L[R/K]VLSIS[Y/F]NNITGE

[I/M]PRN[I/V]GCL[A/T]KLEE[F/L]YIGYN[A/P]I[N/D]G

[T/R]IP[A/T]SLGNISTLQ[N/K]LHVG[S/N],[H/S]/[E/I]GE

[L/I]PPELGKLSNLR[Q/E]I[N/D]F[E/S]ENYNL[I/T]GEIPN

[T/S/A]IFNISSLEFI[A/V]F[T/S]FNYLSGRIP[N/V]LLH[L/F]

PNLIQL[L/F]LANNQLEGEIPRYITNAT[N/K]LE[L/S]L[E/D]LS

[D/V]N[L/R]LTG[T/S]IP[N/Y][D/N]LGNLR[E/K]L[R/K/Q]

[D/Q/E]LFLHHNQL[T/I]ELGFFDSLV[K/N]CRML[R/Q]YVQVGS

NPLN[D/G]VLPSSIGNLSS[T/N]VEYFHIGDAQI[N/S]GFIPTSTG

NM[T/S]GLTTLV[F/L]QDN[S/N]LTGNIPREI[R/G][K/R]LKQL

QGLFL[V/I]NN[G/E]LQGDI[A/T][E/A]VVCDLSNLVRL[A/S]

LS[E/D]NELSGVIP[E/N]C[L/I]G[N/S]L[T/S]MLQ[Q/H]LFL

GSN[K/N]F[E/G]S[K/E]LPLS[F/I]WKM[S/R][S/G]LL[Y/F]

[L/V]N[M/I]S[R/L]NS[I/L][K/E]GEVPSDIGELKAIV[A/E]I

[D/E]ISGNHFSG[S/M]IPSNLGELQ[T/N]L[K/Q]LLSLSNNSFSG

PIP[F/L]SFSNL[K/I]SLE[F/I]LDLSLNNLSGTIPKSFEKL[L/S]

YL[T/Q]SINVSFN[V/A]LEGEIPSGGVFANSTLQSF[S/L/R]GNKG

LCGR[Q/N]I[L/S]EVPACA[I/V]T[T/N]PEQQ[Q/_][S/A/P]

KSK[K/R]L[V/A]LKIVT[P/L][M/V]VISFFLI[F/L]LLV[V/I]

SIWI[M/K]KRKK[K/N]GKSKD[V/I]EKVPEMRTYQLISYHEIQRAT
```

-continued

```
NNFD[E/G]SNLIGVGGSGSVYK[A/G]TL[A/P]SGIVVAIKVLDL

[E/H][N/H]EEVCKRFDTECEV[M/V]RNVRH[K/R]N[L/I]VSVIT

TCSS[E/Q/D]HIRAFVLQYMPNGSLDNWLYKEDRHL[K/N]L[R/L]Q

RVTIMLD[V/T]AMAIEYLHHGNDT[P/Q]IVHCDLKPANVLLD[E/D]

DMVA[R/H]VGDFGISKILAVSK[S/F]M[A/S]HTKTLGTLGYIAPEY

GSEGIVST[R/S]GDVYSYGIMLMEVLAKRRPT[G/D]EEI[F/S]NEN

LGLREWITRAFPRT[M/I]MEVVDAD[M/I]FHD[G/E]E[K/N]I

[T/A]S[E/K]SE[I/L]CILSMIE[L/V]ALDCTK[A/E][T/M]PESR

[I/M]TM[K/N]DVVKRL[N/Y]KIKNTF[G/M/L][N/E][I/T]

[E/_][V/K_][N/L/_][V/_]
```

In one embodiment, the nucleic acid molecule may include the nucleotide sequence of SEQ ID NO:1 and/or encode a polypeptide or protein having the amino acid sequence of SEQ ID NO:2. In one embodiment, the nucleic acid molecule may include the nucleotide sequence of SEQ ID NO:3 and/or encode a polypeptide or protein having the amino acid sequence of SEQ ID NO:4. In another embodiment, the nucleic acid molecule may encode the conserved amino acid sequence of SEQ ID NO:5. In one embodiment, the nucleic acid molecule may include the nucleotide sequence of SEQ ID NO:7 and/or encode a polypeptide or protein having the amino acid sequence of SEQ ID NO:8. In one embodiment, the nucleic acid molecule may include the nucleotide sequence of SEQ ID NO:9 and/or encode a polypeptide or protein having the amino acid sequence of SEQ ID NO:10. In another embodiment, the nucleic acid molecule may encode the conserved amino acid sequence of SEQ ID NO:11.

While activity in particular polypeptide or protein sequences has been identified, variants of those polypeptides or proteins are also contemplated and may also be used as described herein (e.g., to impart or enhance disease resistance). In some embodiments, the polypeptides or proteins of the invention comprise one or more (e.g., 1, 2, 3, 4, 5 or more) amino acid insertions, deletions, or modifications (e.g., substitution of one amino acid for another) compared to SEQ ID NO:2, SEQ ID NO:4, SEQ ID NO:5, SEQ ID NO:8, SEQ ID NO:10, and/or SEQ ID NO:11 or are otherwise substantially identical (e.g., having a sequence at least 80%, 85%, 90%, 95%, 96%, 97%, 98%, 99% or more identical) with the entire sequence of SEQ ID NO:2, SEQ ID NO:4, SEQ ID NO:5, SEQ ID NO:8, SEQ ID NO:10, and/or SEQ ID NO:11. It is contemplated that such variants retain the function of, for example, SEQ ID NO:2, SEQ ID NO:4, SEQ ID NO:5, SEQ ID NO:8, SEQ ID NO:10, and/or SEQ ID NO:11 (e.g., in imparting or enhancing disease resistance and/or in binding to flgII-28). For example, polypeptides or proteins comprising or consisting of an amino acid sequence having one or more (e.g., 1, 2, 3, 4, 5, or more) conservative amino acid substitutions relative to SEQ ID NO:2, SEQ ID NO:4, SEQ ID NO:5, SEQ ID NO:8, SEQ ID NO:10, and/or SEQ ID NO:11, but retaining the function of SEQ ID NO:2, SEQ ID NO:4, SEQ ID NO:5, SEQ ID NO:8, SEQ ID NO:10, and/or SEQ ID NO:11 (e.g., in imparting or enhancing disease resistance and/or in binding to flgII-28) are encompassed. Further, nucleic acid molecules encoding such variants of the peptides of the present invention are also contemplated. Such nucleic acid molecules may have, for example, a nucleotide sequence at least 80%, 85%, 90%, 95%, 96%, 97%, 98%, 99% or more identical) with the entire sequence of SEQ ID NO:1, SEQ ID NO:3, SEQ ID NO:7, and/or SEQ ID NO:9.

The FLS3 nucleic acid molecules of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire FLS3 sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an FLS3 protein and which hybridize under stringent conditions to at least one of the FLS3 nucleic acid molecules disclosed herein, or to variants or fragments thereof, are encompassed by the present invention. Accordingly, the nucleic acid molecule and encoded protein according to the present invention may be an ortholog of FLS3 from *S. lycopersicum* cv. 'Heinz1706', from *S. pimpinellifolium* LA1589, from potato (*S. tuberosum*), and/or from pepper (*Capsicum annum*) referred to herein. Plants that are members of the *Solanaceae* family include, but not limited to, tomato, potato, pepper, tobacco, eggplant, tomatillo, and petunia.

Components of nucleic acid constructs according to the present invention may be heterologous. A polynucleotide sequence is "heterologous to" an organism or a second polynucleotide sequence if it is synthetic or originates from a foreign species, or, if from the same species, is modified from its original form. For example, a promoter operably linked to a heterologous coding sequence (or vice versa) refers to a coding sequence from a species different from that from which the promoter was derived, or, if from the same species, a coding sequence which is not naturally associated with the promoter (e.g., a genetically engineered coding sequence or an allele from a different ecotype or variety).

Methods of producing recombinant nucleic acids for purposes of, e.g., making transgenic plants are well-known. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y., Cold Spring Harbor Press (1989), and Ausubel et al., *Current Protocols in Molecular Biology*, New York, N.Y., John Wiley & Sons (1989), which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA ("T-DNA") is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase ("NOS") gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known by those of ordinary skill in the art (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters Used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the *Chrysanthemum* UEP1 Promoter and Comparative Expression in Florets and Leaves of *Dendranthema grandiflora*," *Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimeric Granule-Bound Starch Synthase-GUS Gene in Transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

Nucleic acid constructs of the present invention include an operable 3' regulatory region, selected from among those which are capable of providing correct transcription termination and polyadenylation of mRNA for expression in the host cell of choice, operably linked to a nucleic acid molecule configured to silence BBTV. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313 (6005):810-812 (1985), which is hereby incorporated by reference in its entirety). Virtually any 3' regulatory region known to be operable in plants would be suitable for use in conjunction with the present invention.

The different components described supra can be ligated together to produce the expression systems which contain the nucleic acid constructs of the present invention, using well known molecular cloning techniques as described in Sambrook et al., *Molecular Cloning: A Laboratory Manual*, Second Edition Cold Spring Harbor, N.Y., Cold Spring Harbor Press (1989), and Ausubel et al. *Current Protocols in Molecular Biology*, New York, N.Y., John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs of the present invention. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual,* Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 µm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of the present invention. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

Yet a further method for introduction is by use of known techniques for genome editing or alteration. Such techniques for targeted genomic insertion involve, for example, inducing a double stranded DNA break precisely at one or more targeted genetic loci followed by integration of a chosen transgene or nucleic acid molecule (or construct) during repair. Such techniques or systems include, for example, zinc finger nucleases ("ZFNs") (Urnov et al., "Genome Editing with Engineered Zinc Finger Nucleases," *Nat Rev Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat Rev Mol Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nat* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7): 397-405 (2013), each of which is hereby incorporated by reference in its entirety).

After transformation, the transformed plant cells must be regenerated. Plant regeneration from cultured protoplasts is described in Evans et al., *Handbook of Plant Cell Cultures*, Vol. 1, New York, N.Y., MacMillan Publishing Co. (1983); Vasil, ed., *Cell Culture and Somatic Cell Genetics of Plants*, Vol. I (1984) and Vol. III (1986), Orlando, Acad. Press; and Fitch et al., "Somatic Embryogenesis and Plant Regeneration from Immature Zygotic Embryos of *Papaya* (*Carica papaya* L.)," *Plant Cell Rep.* 9:320 (1990), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions:

β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y., Cold Spring Harbor Press (1989), which is hereby incorporated by reference in its entirety).

In one embodiment, the transgenic plant is transformed with a bacterial artificial chromosome ("BAC"). A BAC is a cloning vector derived from the naturally occurring F factor of *Escherichia coli*. BACs can accept large inserts of a DNA sequence. In maize, a number of BACs, each containing a large insert of maize genomic DNA, have been assembled into contigs (overlapping contiguous genetic fragments, or "contiguous DNA"). BACs have a propensity for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

Accordingly, one aspect of the present invention relates to a plant or plant seed transformed with one or more nucleic acid constructs described herein. The present invention also encompasses the whole plant, or a component part of a plant, including shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same.

Suitable plants for use in accordance with the present invention include both monocots and dicots. Suitable plants for use in accordance with the present invention also include both crop plants and ornamentals. For example, suitable plants include rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana*, *Saintpaulia*, petunia, pelargonium, poinsettia, chrysanthemum, carnation, crocus, marigold, daffodil, pine, *Medicago truncatula*, *Sandersonia aurantiaca*, and zinnia.

Another aspect of the present invention relates to a method of expressing a nucleic acid molecule in a plant. This method involves providing a transgenic plant or plant seed transformed with a nucleic acid construct comprising a nucleic acid molecule that encodes an FLS3 protein; a 5' heterologous DNA promoter sequence; and a 3' terminator sequence, where the nucleic acid molecule, the DNA promoter sequence, and the terminator sequence are operatively coupled to permit transcription of the nucleic acid molecule. The method also involves growing the transgenic plant or a plant grown from the transgenic plant seed under conditions effective to express the nucleic acid molecule in said transgenic plant or said plant grown from the transgenic plant seed.

Suitable nucleic acid molecules are described above.

In one embodiment a transgenic plant is provided. In another embodiment, a transgenic plant seed is provided.

In one embodiment, providing a transgenic plant or plant seed involves transforming a non-transgenic plant or a non-transgenic plant seed with the nucleic acid construct to yield the transgenic plant or plant seed. Transformation is described above and may include *Agrobacterium*-mediated transformation, whisker method transformation, vacuum infiltration, biolistic transformation, electroporation, microinjection, polyethylene-mediated transformation, or laser-beam transformation.

Yet another aspect of the present invention relates to a method of imparting disease resistance to a plant. This method involves transforming a plant or a plant seed with a nucleic acid molecule that increases expression of an FLS3 protein, where said transforming is effective in imparting disease resistance to the transformed plant or to a transgenic plant produced from the transformed plant seed.

In one embodiment, a plant is transformed. In another embodiment, a plant seed is transformed and the method also involves planting the transformed plant seed under conditions effective for a plant to grow from the planted plant seed. Suitable nucleic acid molecules and are described above.

Imparting disease resistance or enhancing disease resistance refers to an increase in the ability of a plant to prevent pathogen infection or pathogen-induced symptoms. Disease resistance may be increased compared to a control plant (for example, an unmodified or non-transgenic plant). In one embodiment, the level of resistance in a non-naturally occurring transgenic plant of the invention is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the resistance exhibited by a control plant. The level of resistance is measured using conventional methods. For example, the level of resistance to a pathogen may be determined by comparing physical features and characteristics (for example, plant height and weight) or by comparing disease symptoms (for example, delayed lesion development, reduced lesion size, leaf wilting and curling, water-soaked spots, amount of pathogen growth, and discoloration of cells) of the non-naturally occurring plant (e.g., a transgenic plant).

Disease resistance can be increased resistance relative to a particular pathogen species or genus or can be increased resistance to a broad range of pathogens (e.g., pattern-triggered immunity, systemic acquired resistance). In one embodiment, the pathogen is a bacterial plant pathogen. By way of example, bacterial pathogens may belong to *Acidovorax*, *Agrobacterium*, *Burkholderia*, *Candidatus Liberibacter*, *Clavibacter*, *Curtobacterium*, *Dickeya*, *Erwinia*, *Pantoea*, *Pectobacterium*, *Phytoplasma*, *Pseudomonas*, *Ralstonia*, *Spiroplasma*, *Streptomyces*, *Xanthomonas*, and *Xylella*. See PLANT PATHOGENIC BACTERIA: GENOMICS AND MOLECULAR BIOLOGY, Robert W. Jackson Ed., Norfolk, UK, Caister Academic Press (2009), which is hereby incorporated by reference in its entirety.

A further aspect of the present invention relates to a method of imparting disease resistance to a plant. The method involves providing a plant having a gene encoding an FLS3 protein, and applying to the plant and/or area of cultivation of the plant a flgII-28 peptide or an FLS3-binding portion thereof, thereby imparting disease resistance to the plant.

In one embodiment, the gene is a transgene. In one embodiment, providing the plant includes transforming a plant or a plant seed with a nucleic acid molecule that increases expression of an FLS3 protein. Suitable nucleic acid molecules are described above.

In one embodiment, the flgII-28 peptide comprises the amino acid sequence of SEQ ID NO:12, as follows: ESTNILQRMREL[A/V]VQ[S/F]RNDSNSATDR[E/D]A (Cai et al., "The Plant Pathogen *Pseudomonas syringae* pv. tomato is Genetically Monomorphic and Under Strong Selection to Evade Tomato Immunity," *PLoS Pathog.* 7(8): e1002130 (2011) and Clarke et al., "Allelic Variation in Two Distinct *Pseudomonas syringae* Flagellin Epitopes Modulates the Strength of Plant Immune Responses But Not Bacterial Motility," *New Phytol* 200:847-860 (2013), each of which is hereby incorporated by reference in its entirety). In another embodiment, the flgII-28 peptide comprises the amino acid sequence of SEQ ID NO:13, as follows: ES[T/V][N/S]ILQRMRELAVQSRNDSNS[A/S][T/E][D/G]R[E/D]A (Clarke et al., "Allelic Variation in Two Distinct *Pseudomonas syringae* Flagellin Epitopes Modulates the Strength of Plant Immune Responses But Not Bacterial Motility," *New Phytol* 200:847-860 (2013), which is hereby incorporated by reference in its entirety). In another embodiment, the flgII-28 peptide comprises the amino acid sequence of SEQ ID NO:14, as follows: EIGSNLQRIRELSVQSSNATNSASDRDA. In another embodiment, the flgII-28 peptide comprises the amino acid sequence of SEQ ID NO:15, as follows: EINNNLQRVRELAVQSANSTNSQSDLDS (Meng et al., "*Salmonella* colonization activates the plant immune system and benefits from association with plant pathogenic bacteria," *Environ Microbiol* 15(9): 2418-2430 (2013), which is hereby incorporated by reference in its entirety). Also contemplated are variants of SEQ ID NOs:12-15, which retain the function of binding FLS3 and/or causing pattern-triggered immunity in a plant. In some embodiments, such peptides comprise one or more (e.g., 1, 2, 3, 4, 5 or more) amino acid insertions, deletions, or modifications (e.g., substitution of one amino acid for another) compared to SEQ ID NOs:12-15 or are otherwise substantially identical (e.g., having a sequence at least 80%, 85%, 90%, 95%, 96%, 97%, 98%, 99% or more identical) with the entire sequence of SEQ ID NOs:12-15. Further, nucleic acid molecules encoding such variants of the peptides of SEQ ID NOs:12-15 are also contemplated. Such nucleic acid molecules may have, for example, a nucleotide sequence at least 80%, 85%, 90%, 95%, 96%, 97%, 98%, 99% or more identical) with the entire sequence of SEQ ID NOs:12-15. The flgII-28 peptide or variant as described herein may include a heterologous portion (e.g., fusion protein or peptide). For example, a fusion protein may include two or more flgII-28 peptides or variants optionally joined by a linker. A fusion protein may include one or more flgII-28 peptides or variants joined (optionally with a linker) to a further peptide capable of, e.g., eliciting PTI and/or hypersensitive response in a plant.

FlgII-28 peptides or fragments or variants thereof may be formulated (either together or separately) in a manner common for agrochemical formulations. Agricultural formulations of active substances are well known. Non-limiting examples include solutions, emulsions, suspensions, dusts, powders, pastes, and granules. The particular formulation chosen may vary depending on the particular intended application. In each case, it is typically advantageous to ensure a fine and even distribution of the active ingredient(s) in a liquid or solid carrier. Formulation methods are taught, e.g., in U.S. Pat. No. 3,060,084 to Littler and European Patent No. 0707445 to BASF AG (for liquid concentrates); Browning, "Agglomeration," Chemical Engineering pp. 147-48 (1967); Perry's Chemical Engineer's Handbook, 4th Ed., McGraw-Hill, New York, 1963; PCT Publication No. WO 91/13546 to E.I. Du Pont De Nemours and Co.; U.S. Pat. No. 4,172,714 to Albert; U.S. Pat. No. 4,144,050 to Frensch et al; U.S. Pat. No. 3,920,442 to Albert; U.S. Pat. No. 5,180,587 to Moore; U.S. Pat. No. 5,232,701 to Ogawa et al; U.S. Pat. No. 5,208,030 to Hoy et al, Great Britain Patent No. 2,095,558; U.S. Pat. No. 3,299,566 to Macmullen; Klingman, Weed Control as a Science, J. Wiley & Sons, New York, 1961; Hance et al, Weed Control Handbook, 8th Ed., Blackwell Scientific, Oxford, 1989; and Mollet and Grubemann, Formulation Technology, Wiley VCH Verlag, Weinheim, 2001, each of which is hereby incorporated by reference in its entirety.

The area of cultivation is any type of environment, soil, area, or material where the plant is growing or intended to grow. The composition comprising the flgII-28 peptide or fragment or variant thereof may be applied in the form of directly sprayable solutions, powders, suspensions, dispersions, emulsions, oil dispersions, pastes, dustable products, materials for spreading, or granules, by means of spraying, atomizing, dusting, spreading, brushing, immersing, or pouring. The application form depends on the intended purpose to ensure in each case the finest possible distribution of the active compound(s).

A further aspect of the present invention relates to a method of identifying a candidate plant suitable for breeding that displays enhanced disease resistance. This method involves providing a candidate plant; analyzing the candidate plant for the presence, in its genome, of a gene encoding an FLS3 protein; identifying, based on said analyzing, a candidate plant suitable for breeding that includes in its genome, a gene encoding an FLS3 protein; and breeding the identified plant with at least one other plant.

In one embodiment, analyzing the candidate plant for the presence, in its genome, of a gene encoding an FLS3 protein involves isolating genomic DNA from the plant, germplasm, pollen, or seed of the plant; analyzing genomic DNA from the plant, germplasm, pollen, or seed of the plant for the presence of the gene encoding the FLS3 protein; and detecting the gene encoding the FLS3 protein.

In one embodiment, the breeding involves crossing, making hybrids, backcrossing, self-crossing, double haploid breeding, and/or combinations thereof.

In one embodiment, a transgenic plant transformed with a nucleic acid molecule that encodes an FLS3 protein is provided as the candidate plant. In one embodiment, providing the transgenic plant involves transforming a plant or plant seed with a nucleic acid construct according to the present invention and growing the transgenic plant or a plant grown from the transgenic plant seed under conditions effective to express the nucleic acid molecule in the transgenic plant or said plant grown from the transgenic plant seed.

Yet a further aspect of the present invention relates to a method for enhancing efficiency of transformation of a plant by *Agrobacterium*. This method involves transforming a plant or a plant seed with a nucleic acid construct effective to silence expression of a nucleic acid molecule that encodes an FLS3 protein, where said transforming is effective to reduce or eliminate expression of FLS3 protein in the plant and said nucleic acid construct. The nucleic acid construct includes a nucleic acid molecule configured to silence FLS3 protein expression; a 5' DNA promoter sequence; and a 3' terminator sequence, where the nucleic acid molecule, the promoter, and the terminator are operatively coupled to permit expression of the nucleic acid molecule.

In one embodiment, this method involves simultaneous or sequential exposure of the plant cell to an *Agrobacterium* strain that transforms a plant variety with a nucleic acid molecule of interest.

In one embodiment, the bacterium is *A. tumefaciens* having a functional type IV secretion system.

The FLS3 protein may comprise the amino acid sequence of SEQ ID NO:2, SEQ ID NO:4, SEQ ID NO:5, SEQ ID NO: 8, SEQ ID NO:10, or SEQ ID NO:11 and/or may be encoded by the nucleotide sequence of SEQ ID NO:1, SEQ ID NO: 3, SEQ ID NO:7, or SEQ ID NO: 9.

In one embodiment, a plant is transformed. In another embodiment according to this aspect of the claimed invention, a plant seed is transformed and the method also involves planting the transformed plant seed under conditions effective for a plant to grow from the planted plant seed.

In another embodiment, the nucleic acid molecule is positioned in the nucleic acid construct to result in suppression or interference of endogenous mRNA encoding the FLS3 protein.

In one aspect of the present invention, the nucleic acid construct results in suppression or interference of FLS3 protein expression by the nucleic acid molecule of the construct containing a dominant negative mutation and encoding a non-functional FLS3 protein. Examples of such mutations are described with respect to FIGS. 2A and 2B above.

In another aspect of the present invention, the nucleic acid construct results in interference of FLS3 protein expression by sense or co-suppression in which the nucleic acid molecule of the construct (e.g., that encoding FLS3 or a fragment thereof) is in a sense (5'→3') orientation. Co-suppression has been observed and reported in many plant species and may be subject to a transgene dosage effect or, in another model, an interaction of endogenous and transgene transcripts that results in aberrant mRNAs (Senior, "Uses of Plant Gene Silencing," *Biotechnology and Genetic Engineering Reviews* 15:79-119 (1998); Waterhouse et al., "Exploring Plant Genomes by RNA-Induced Gene Silencing," *Nature Review: Genetics* 4: 29-38 (2003), which are hereby incorporated by reference in their entirety). A construct with the nucleic acid molecule (or fragment thereof) in the sense orientation may also give sequence specificity to RNA silencing when inserted into a vector along with a construct of both sense and antisense nucleic acid orientations as described infra (Wesley et al., "Construct Design for Efficient, Effective and High-Throughput Gene Silencing in Plants," *Plant Journal* 27(6) 581-590 (2001), which is hereby incorporated by reference in its entirety).

In another embodiment of the present invention, the nucleic acid construct results in interference of FLS3 expression by the use of antisense suppression in which the nucleic acid molecule of the construct (e.g., that encoding FLS3 or a fragment thereof) is an antisense (3'→5') orientation. The use of antisense RNA to down-regulate the expression of specific plant genes is well known (van der Krol et al., *Nature,* 333:866-869 (1988) and Smith et al., *Nature,* 334: 724-726 (1988), which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). In the target cell, the antisense nucleic acids hybridize to a target nucleic acid and interfere with transcription, and/or RNA processing, transport, translation, and/or stability. The overall effect of such interference with the target nucleic acid function is the disruption of protein expression (Baulcombe, "Mechanisms of Pathogen-Derived Resistance to Viruses in Transgenic Plants," *Plant Cell* 8:1833-44 (1996); Dougherty, et al., "Transgenes and Gene Suppression: Telling us Something New?," *Current Opinion in Cell Biology* 7:399-05 (1995); Lomonossoff, "Pathogen-Derived Resistance to Plant Viruses," *Ann. Rev. Phytopathol.* 33:323-43 (1995), which are hereby incorporated by reference in their entirety). Accordingly, one aspect of the present invention involves a nucleic acid construct which contains an antisense nucleic acid molecule to a nucleic acid molecule encoding an FLS3 protein (or fragment thereof).

Interference of FLS3 expression is also achieved in the present invention by the generation of double-stranded RNA ("dsRNA") through the use of inverted-repeats, segments of gene-specific sequences oriented in both sense and antisense orientations. In one embodiment of this aspect of the present invention, sequences in the sense and antisense orientations are linked by a third segment, and inserted into a suitable expression vector having the appropriate 5' and 3' regulatory nucleotide sequences operably linked for transcription. The expression vector having the modified nucleic acid molecule is then inserted into a suitable host cell or subject. In the present invention, the third segment linking the two segments of sense and antisense orientation may be any nucleotide sequence such as a fragment of the β-glucuronidase ("GUS") gene. In another embodiment of this aspect of the present invention, a functional (splicing) intron of the FLS3 gene may be used for the third (linking) segment, or, in yet another aspect of the present invention, other nucleotide sequences without complementary components in the FLS3 gene may be used to link the two segments of sense and antisense orientation (Chuang et al., "Specific and Heritable Genetic Interference by Double-Stranded RNA in *Arabidopsis thaliana,*" *Proc. Nat'l Academy of Sciences USA* 97(9): 4985-4990 (2000); Smith et al., "Total Silencing by Intron-Spliced Hairpin RNAs," *Nature* 407:319-320 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety). In any of the embodiments with inverted repeats of FLS3, the sense and antisense segments may be oriented either head-to-head or tail-to-tail in the construct.

Another aspect of the present invention involves using hairpin RNA ("hpRNA") which may also be characterized as dsRNA. This involves RNA hybridizing with itself to form a hairpin structure that comprises a single-stranded loop region and a base-paired stem. Though a linker may be used between the inverted repeat segments of sense and antisense sequences to generate hairpin or double-stranded RNA, the use of intron-free hpRNA can also be used to achieve silencing of FLS3 expression.

Alternatively, in another aspect of the present invention, a plant may be transformed with constructs encoding both sense and antisense orientation molecules having separate promoters and no third segment linking the sense and antisense sequences (Chuang et al., "Specific and Heritable Genetic Interference by Double-Stranded RNA in *Arabidop-* sis thaliana," *Proc. Nat'l Academy of Sciences USA* 97(9): 4985-4990 (2000); Waterhouse et al., "Exploring Plant Genomes by RNA-Induced Gene Silencing," *Nat Rev Genet.* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety).

Altering expression (e.g., inhibition of, or interference with, endogenous expression) of FLS3 can also be accomplished using known techniques for targeted alteration of genes, such as zinc finger nucleases ("ZFNs") (Urnov et al., "Genome Editing with Engineered Zinc Finger Nucleases," *Nat Rev Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat Rev Mol Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nat* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7):397-405 (2013), each of which is hereby incorporated by reference in its entirety).

EXAMPLES

The following examples are provided to illustrate embodiments of the present invention but are by no means intended to limit its scope.

Example 1—*Agrobacterium tumefaciens* Transient Assay in *Nicotiana benthamiana* and Tomato Materials:
Induction media (0.05 M MES, 0.5% D-glucose, 0.025% $NaH_2PO_4$, 0.1% $NH_4Cl$, 0.03% $MgSO_4$ $7H_2O$, 0.015% KCl, 0.00025% $FeSO_4$ $7H_2O$, 0.01% $CaCl_2$ $2H_2O$, pH 5.6); infiltration media (0.01 M MES, 0.01 M $MgCl_2$, pH 5.6); 200 mM acetosyringone (19.6 mg in 0.5 mL DMSO).

Procedure:
The *Agrobacterium* strains GV2260 or GV3101 containing constructs expressing genes of interest were streaked on Lysogeny Broth (LB) solid media with antibiotics and grown for 2 days at 30° C. Bacteria were suspended in induction media supplemented with antibiotics and 200 µM acetosyringone and incubated at room temperature with shaking for 5-6 hours. Bacterial cultures were washed twice with infiltration media and the bacterial pellet was resuspended in infiltration media. The $OD_{600}$ of the culture at 1:100 dilution was measured and a cell suspension made of the appropriate (i.e., 0.1-0.2) $OD_{600}$ in infiltration media supplemented with 200 µM acetosyringone. All constructs were mixed at equal concentrations with *Agrobacterium* containing a construct expressing the viral suppressor of silencing p19. Fully expanded leaves of *Nicotiana benthamiana* or tomato were used for infiltration. First, a hole was made in the leaf using a needle, and then the leaf was infiltrated with the solution containing the *Agrobacterium* using a needle-less syringe. Plants were kept for 24 hours before collecting samples for ROS analysis (see infra Example 3), or for 48 hours before collecting samples for immunoblot analysis (see infra Example 4).

Example 2—Virus-Induced Gene Silencing ("VIGS") Protocol for *Nicotiana benthamiana*

Materials:
LB solid media supplemented with antibiotics; infiltration buffer (10 mM MES, 10 mM MgCl2, pH 5.5; 200 mM acetosyringone (0.039 g dissolved in 1 mL DMSO).

Procedure:
The *Agrobacterium* strains GV2260 or GV3101 containing constructs expressing genes of interest were streaked on Lysogeny Broth (LB) solid media with antibiotics and grown for 2 days at 30° C. Bacteria were suspended in LB liquid media supplemented with antibiotics and 200 µM acetosyringone and incubated at 30° C. overnight with shaking. Bacterial cultures were washed twice with infiltration media and the bacterial pellet was suspended in infiltration media. The $OD_{600}$ of the culture at 1:100 dilution was measured and a cell suspension made of the appropriate (i.e., 0.1-0.2) $OD_{600}$ in infiltration media supplemented with 200 µM acetosyringone. The two constructs (i.e., TRV1 and TRV2 with the gene of interest) were mixed at equal concentrations. Leaves of 3-week-old *Nicotiana benthamiana* plants were used for infiltration. First, a hole was made in the leaf using a needle, then the leaf was infiltrated with the solution containing the *Agrobacterium* using a needle-less syringe. Plants were kept for 4-5 weeks before use.

Example 3—ROS Assay Protocol

Materials:
Luminol (17 mg/mL in DMSO); horseradish peroxidase type VI (10 mg/mL in $H_2O$; cork borer #1 or 2; 96-well microplates Procedure:
Leaf disks were obtained using the cork borer, and disks were floated on water in 96-well microplates, adaxial (upper) side facing up. After overnight incubation, the water was removed and replaced with 100 µL per well ROS assay solution (34 µg/mL luminol, 20 µg/mL horseradish peroxidase, with an appropriate concentration of the MAMP of interest). The resulting luminescence was measured using a plate reader (i.e., Biotek Synergy 2 with Gen5 1.10 software). The luminescence was measured over 45 minutes with a 27 millisecond interval for a total of 101 reads.

Example 4—Protocol for Demonstrating Binding of flgII-28 to FLS3

Procedure: Approximately 25 grams of *Nicotiana benthamiana* tissue overexpressing FLS3 with a c-terminal GFP tag fusion was ground in a mortar with a pestle in liquid nitrogen. 200 mL of extraction buffer (50 mM MOPS-KOH, pH7.5, 0.5 M sorbitol, 5 mM DTT, 5 mM EDTA, pH8.0, 1% PVPP, 1 mM PMSF) was then added to the ground tissue and the extract was filtered through Miracloth. The extract was centrifuged in 40 mL round-bottom tubes at 10,500 rpm for 25 minutes at 4° C. 40 mL of supernatant was transferred to each of 6 open-top tubes and centrifuged for 75 minutes at 23,600 rpm (100,000×g) at 4° C. Microsomal membranes were suspended in 10 mL of suspension buffer (25 mM Tris-HCl, pH7.5, 0.25 M sucrose, 10 mM potassium phosphate, pH7.5, 28.8 mM NaCl). Samples were then sonicated for 2×30 seconds at half power with samples kept in an ice bath. 9 mL of suspended microsomal membranes was then added in 27 g phase mixture (6% w/w dextran T-500, 6% w/w PEG 3350, 0.25 M sucrose, 10 mM potassium phosphate, pH7.5, 28.8 mM NaCl) and mixed by inverting 20 times. The mixture was then centrifuged at 1,000 rpm for 5 minutes at 4° C. and then the upper layer was transferred to a fresh tube containing 10 mL of dextran phase solution while adding 10 mL of PEG phase solution to lower layer (phase solutions were generated using 6% w/w dextran T-500, 6% w/w PEG 3350, 0.25 M sucrose, 10 mM potassium phosphate, pH7.5, 28.8 mM NaCl). This was mixed by inversion and centrifuged. Then the upper layer (from original upper layer) was transferred to a fresh tube with 10 mL of dextran phase solution, mixed by inversion, and centrifuged. The upper layers of mixtures from 2 tubes were then combined into 40 mL open-top tube and filled with suspension buffer. This was then centrifuged for 120 minutes at 23,600 rpm (100,000×g) at 4° C. The supernatant was removed and the plasma membranes suspended in 1 mL binding buffer (25 mM MES, pH6.0, 3 mM MgCl2, 10 mM NaCl). This suspension was then sonicated for 5 sec using a sonicating water bath. 5-10 µM MAMP peptide was added and the plasma membrane-enriched microsomes/peptide mixture incubated on ice in the dark cold room for 15 min with mixing every 5 min. Suspended membranes were transferred to a cold watch glass (65 mm OD×50 mm ID×10 mm depth). Membranes were irradiated with UV lamp for 15 min; the watch glass/lamp were moved every 5 min to keep cold. The suspended membranes were them transferred to 1.5 mL tube and 10 µL Triton X-100 (final conc. 1%) and 5 µL of 20% SDS (final conc. 0.1%) were added. Next 20 µL of anti-GFP-nanotrap slurry was used per sample. Resin was washed with 1 mL cold binding buffer supplemented with detergents (1% Triton X-100 and 0.1% SDS). Washed resin was transferred into 1.5 mL tube containing the MAMP treated and UV photo-crosslinked membranes, incubated at 4° C. (cold room) with rotating for 2 hr. Resin was washed twice with 1 mL of chilled PBS buffer. The resin was washed three times with 1 mL of chilled RIPA buffer (PBS pH 7.4, 1% Triton, 0.5% sodium deoxycholate, 0.1% SDS). After the third wash, the beads were suspended in 465 µL of RIPA buffer and 35 µL of click reaction mix (500 µM LTTP Ligand, 250 µM CuSO4-5H2O, 2 mM Na ascorbate, 100 µM N3-Biotin) was added. Click reactions were incubated with rotating at 4° C. overnight. Resin was washed 5 times with 1 mL of RIPA buffer. Upon removal of the final wash, the 20 µL pellet was suspended in 30 µL of freshly prepared 2× sample buffer+10% β-mercaptoethanol. Material was eluted by boiling for 6 min. Precast BioRad TGX 4-20% gradient gels, 1 mm thick with 10 wells, were used. Samples were loaded on to the gel, and the gel was run at 200 V for 90 min and then transferred to PVDF membrane at 100 V for 90 min. Blocking was carried out in 5% milk TBS for 1 hr at room temperature. The primary antibody anti-GFP was used at 1:4000, 4° C. overnight, in 1% milk TBS-Tween20. The secondary antibody anti-mouse-HRP was used at 1:20,000, 1 hr at room temp, in 1% milk TBS-Tween20. Alternatively, the conjugated primary antibody streptavidin-HRP was used at 1:5,000, 4° C. overnight, in 1% milk TBS-Tween20. Detection was carried out using an HRP substrate reagent.

Example 5—Identification of FLS3

Figure 1B:
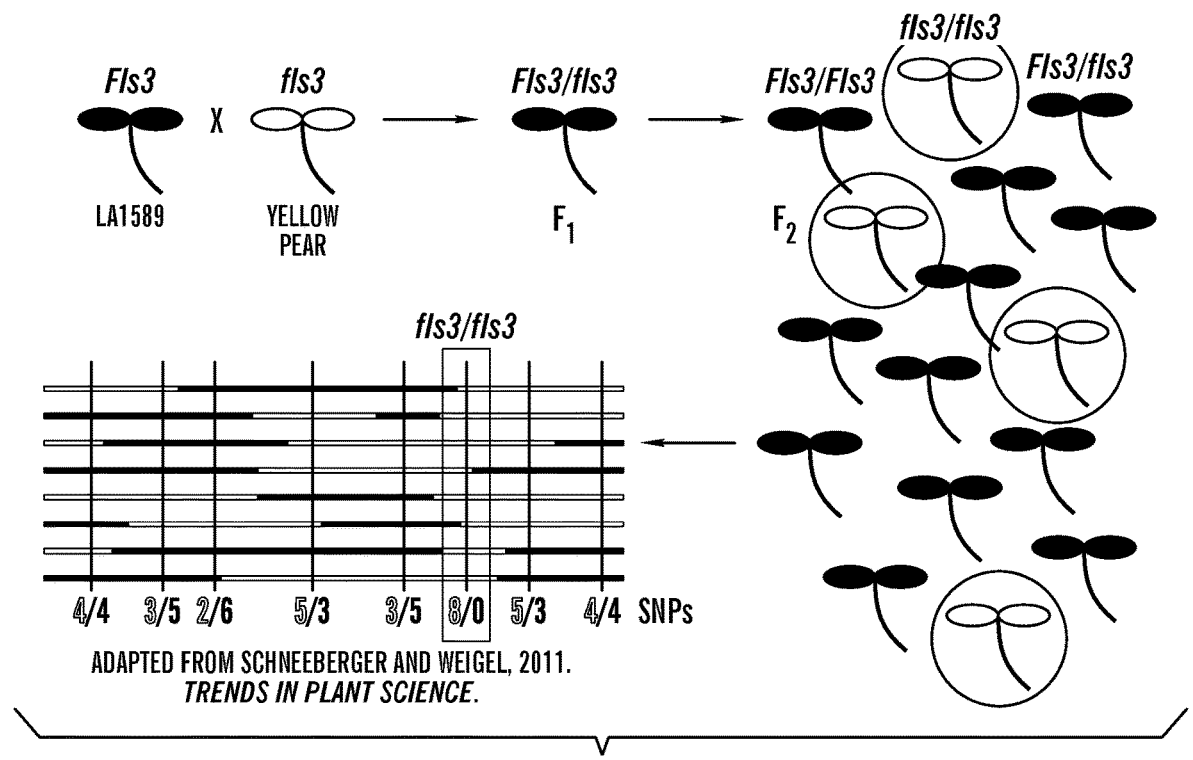
Figure 1C:
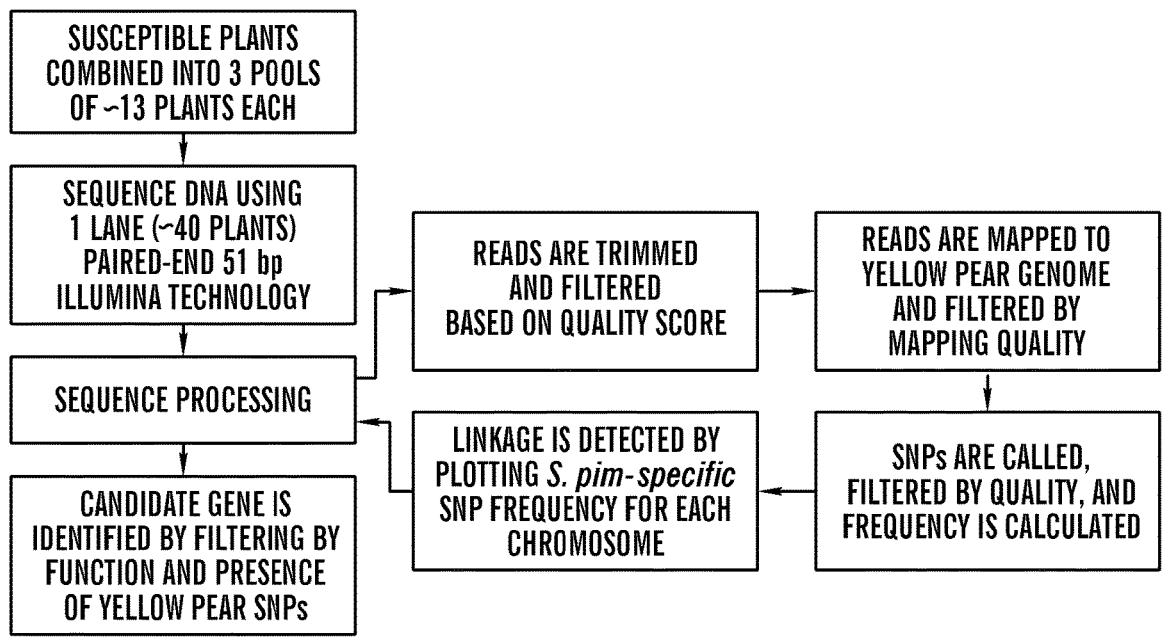
Figure 1D:
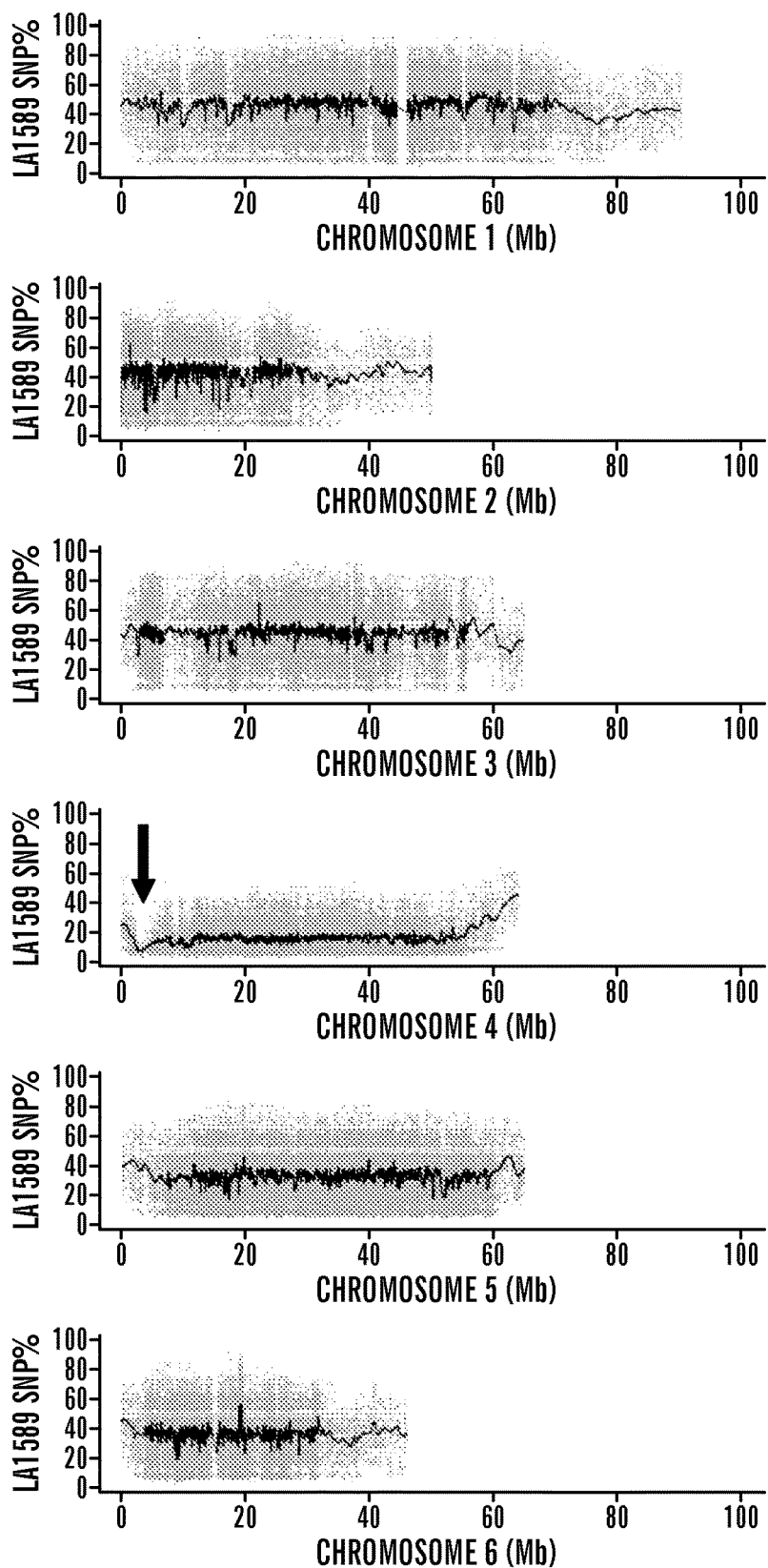
Figure 1D:
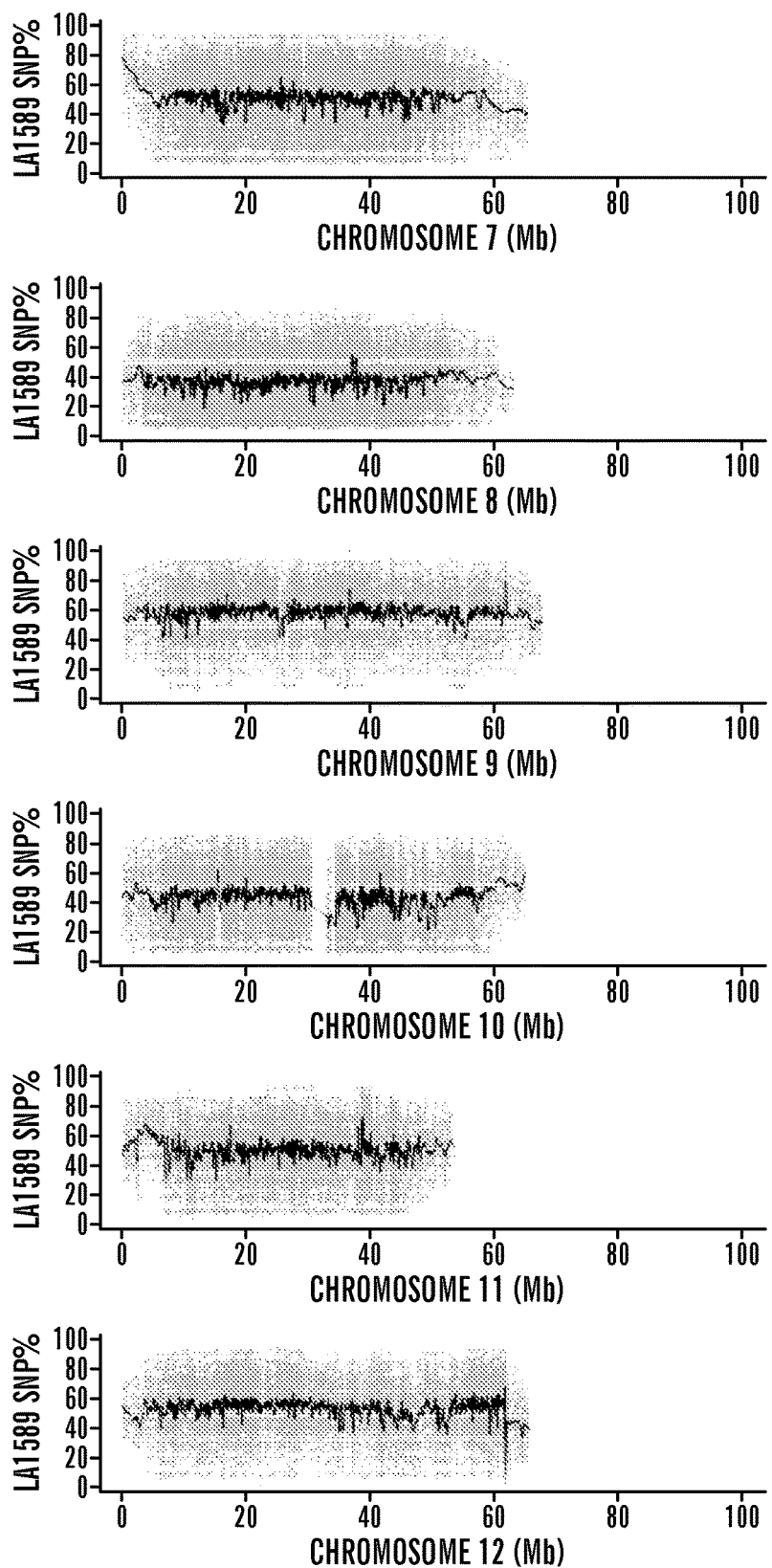
Figure 1E:
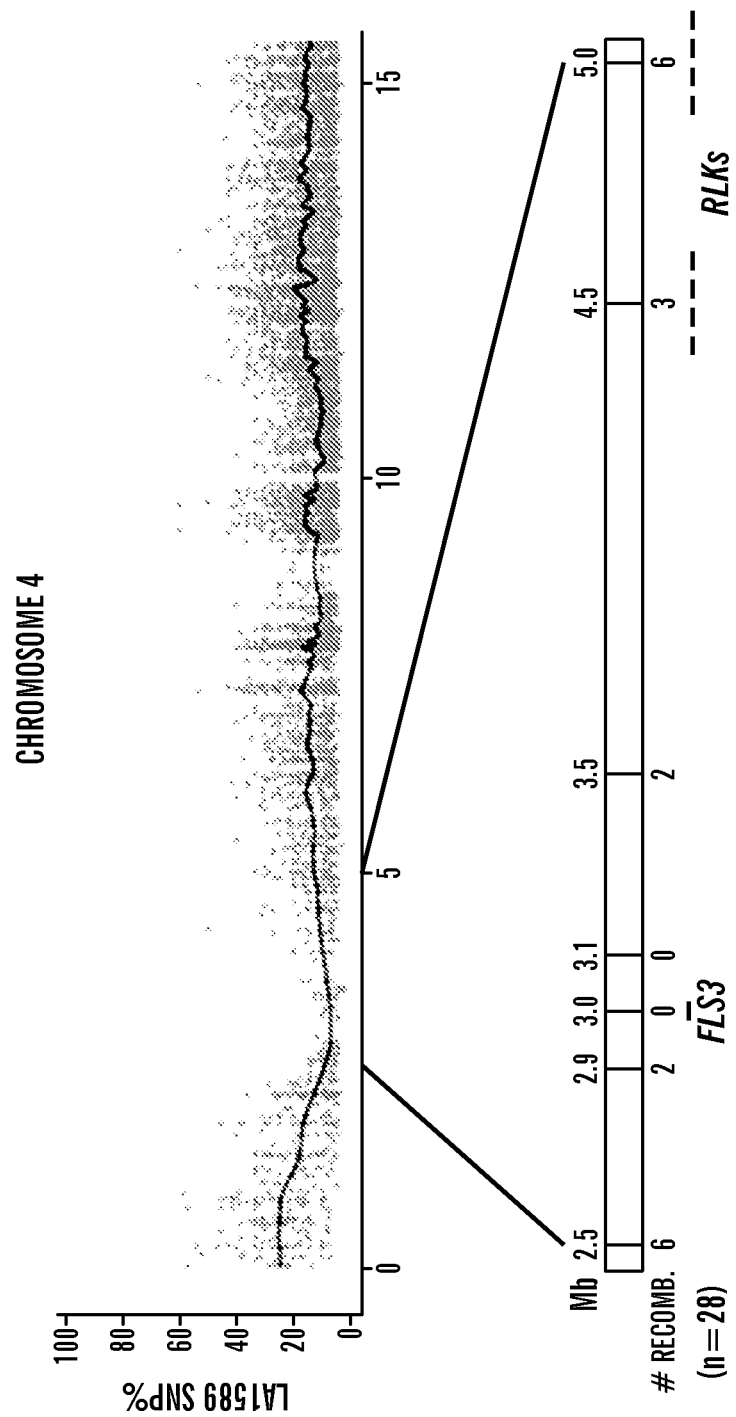

Using an F2 population, mapping-by-sequencing was performed followed by fine mapping to identify a gene encoding a RLK that is linked to flgII-28 responsiveness in tomato. In order to identify the responsible gene by bulked segregant analysis, segregating populations were generated by crossing flgII-28 sensitive (LA1589) and insensitive (Yellow Pear) accessions (FIGS. 1A-1B). Testing for the sensitivity of F2 plants to 100 nM flgII-28 treatment using the ROS assay revealed a segregation ratio of LA1589× Yellow Pear of 468:108. To identify the genomic region linked to flgII-28 insensitivity, DNA libraries for next-generation Illumina® sequencing were generated using flgII-28 non-responsive F2 plants, sent for sequencing, and mapped onto a Yellow Pear genome (FIGS. 1C-1D). Only chromosome 4 had a notable deviation from the expected 1:1 LA1589:Yellow Pear SNP ratio, with one region in particular having very few LA1589-specific SNPs (FIGS. 1D-1E). This region, spanning 2.619 to 5.486 Mb on chromosome 4, contains 322 annotated genes including 9 leucine-rich repeat, receptor-like kinases (LRR-RLKs). Fine genetic mapping was used to narrow down the candidate list to one gene on chromosome 4. The coding sequence for FLS3 from *S. pimpinellifolium* LA1589 was identified as SEQ ID NO:3, as set forth supra. The protein sequence for FLS3 from *S. pimpinellifolium* LA1589 was identified as SEQ ID NO:4, as set forth supra. The coding region then identified in Heinz 1706 is set forth above as SEQ ID NO:1 and the identified amino acid sequence is that of SEQ ID NO:2, as set forth supra.

Figure 2A:
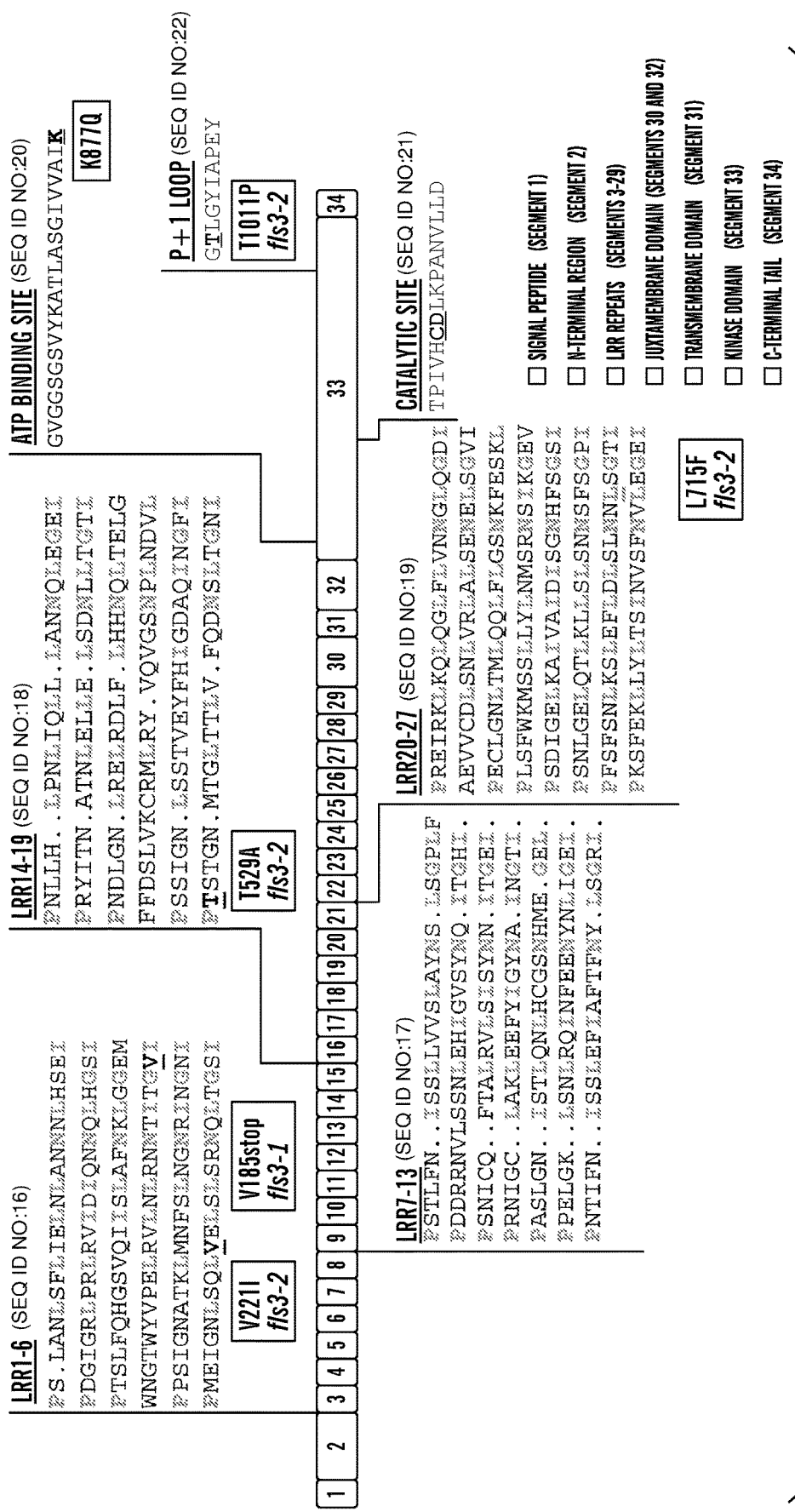
Figure 2B:
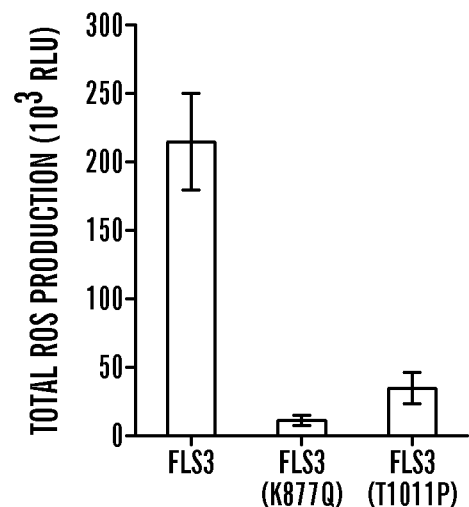
Figure 2C:
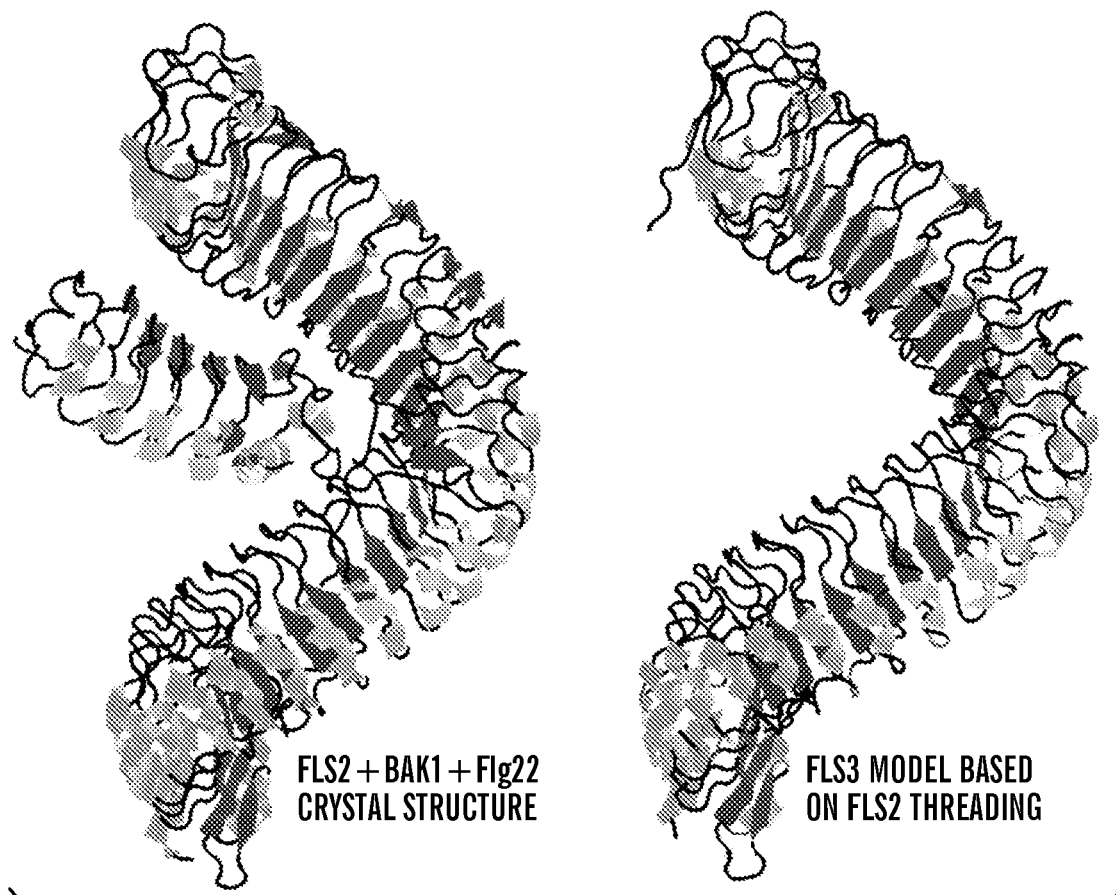
Figure 2E:
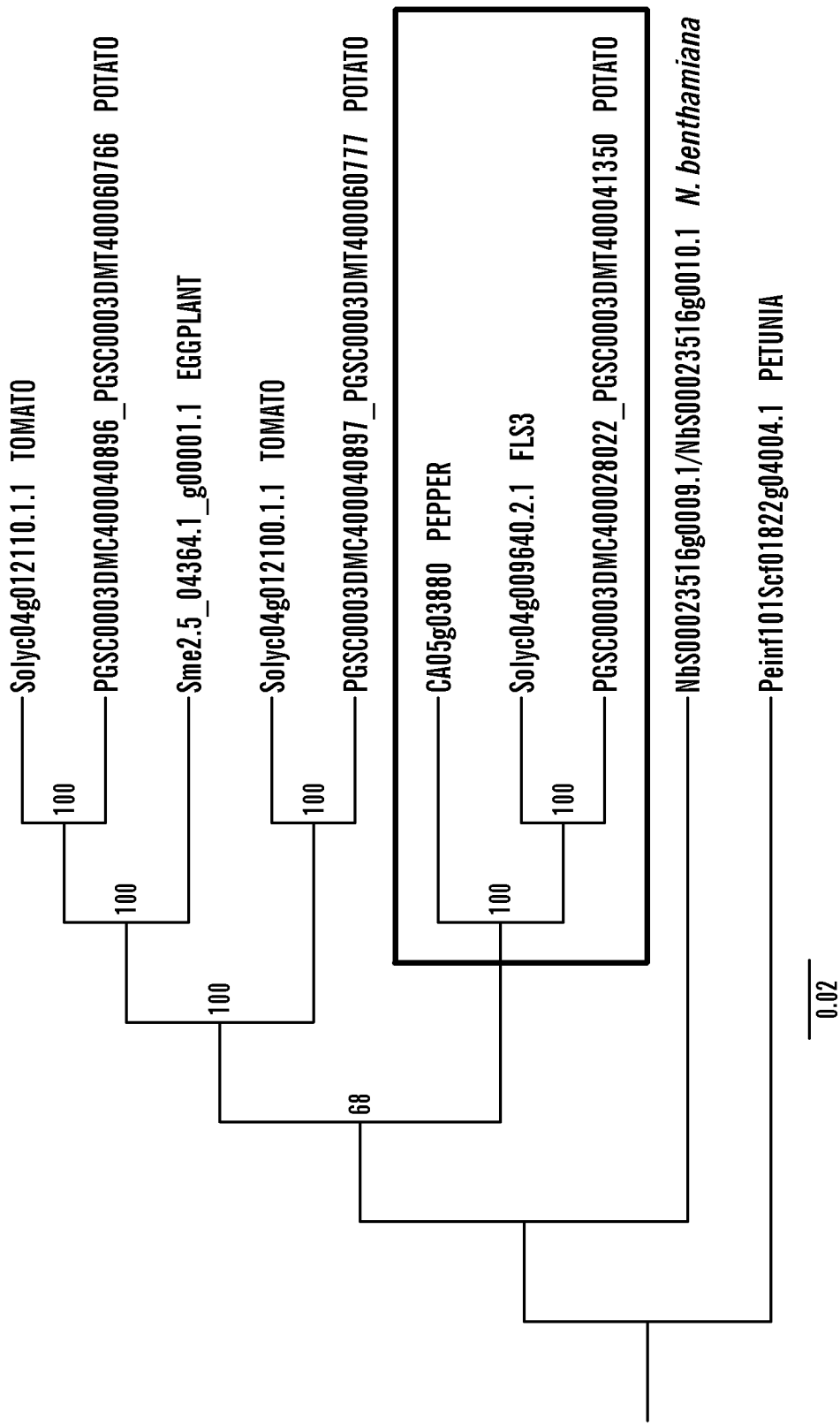

The FLS3 protein structure, its similarity to FLS2, and FLS3 orthologs from other *Solanaceae* species were elucidated. The wild type FLS3 allele encodes a class XII LRR RLK with 27 LRRs and an intracellular non-RD kinase domain (FIG. 2A). FLS3 variants and their corresponding activities were characterized (FIG. 2A-2B). FLS3 has overall similarity in domain architecture to FLS2 and comparative modeling was used to predict FLS3 structure based on the crystal structure of FLS2 (FIG. 2C), but the proteins are only 35% identical at the amino acid level (FIG. 2D). Potential FLS3 orthologs were identified from sequenced accessions of potato and pepper, but not from *Nicotiana benthamiana* or petunia (FIG. 2E). These observations suggest that the gene is likely to have arisen via a duplication event prior to the divergence of *Capsicum* from *Solanum*.

Example 6—Confirmation of FLS3 Identity

Figure 3A:
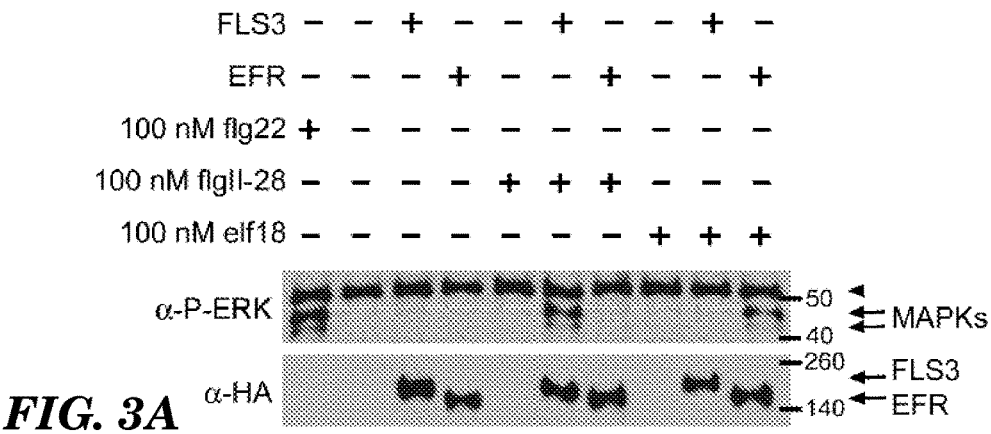
FIGS. 3A-3E illustrates that expression of FLS3 in insensitive plants confers flgII-28 responsiveness, that the signaling appears to be BAK1-dependent, and that the presence of FLS3 is associated with increased resistance to bacterial infection.
Figure 3B:
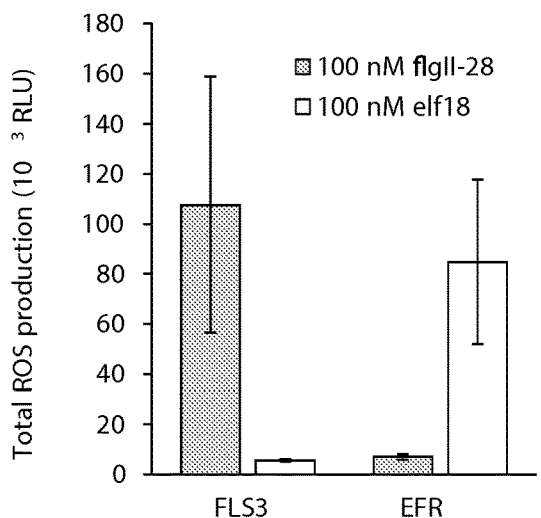

After identification of FLS3 using a genetics approach, the identity of FLS3 was confirmed using independent gain-of-function approaches. First, the activity of FLS3 in tomato protoplasts was tested. Leaf protoplasts were generated from the tomato cultivar 'Yellow Pear' that does not respond to flgII-28 treatment. Protoplasts expressing FLS3 and treated with flgII-28 showed an increase in MAPK activation (FIG. 3A), which indicates active signaling. Protoplasts that expressed the receptor EFR only showed increase in MAPK activation when treated with elf18, but not with flgII-28, demonstrating the specificity of the signaling. Next, FLS3 was transiently expressed in *Nicotiana benthamiana*, a tobacco relative which does not respond to flgII-28 treatments and so presumably does not have FLS3. Using the *N. benthamiana* plants that expressed FLS3, it was tested whether these plants could respond to flgII-28 treatment by measuring the reactive oxygen species ("ROS") production. ROS production is a hallmark output during the signaling response to MAMP treatment. It was observed that treatment of FLS3-expressing leaves resulted in a characteristic ROS burst profile when treated with flgII-28, but not when treated with elf18, an unrelated MAMP peptide (FIG. 3B). In order to demonstrate the specificity of this response, EFR (another PRR receptor not found in either tomato or *N. benthamiana*) was also transiently expressed in *N. bentha-* miana. A ROS burst was observed when these plants were treated with the EFR cognate peptide elf18, but not when EFR-expressing leaves were treated with flgII-28.

Figure 3C:
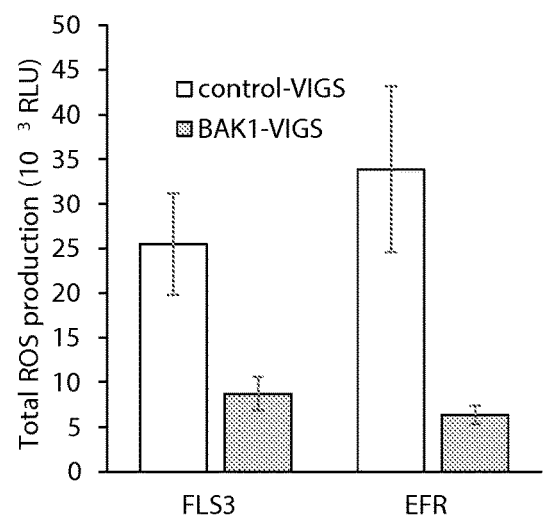
Figure 3D:
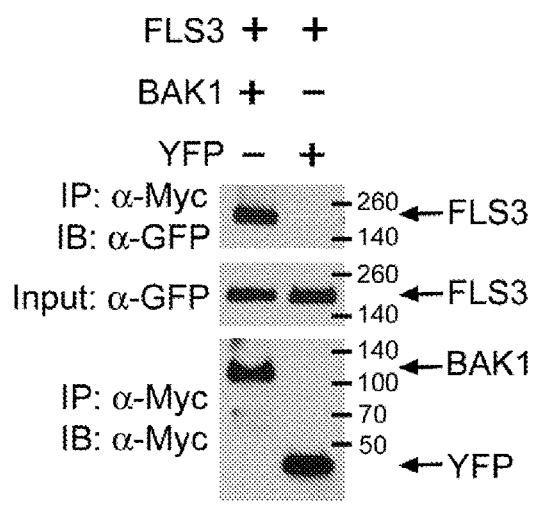

Next, FLS3 was expressed in *N. benthamiana* plants that lacked BAK1, a protein that functions as a co-receptor with many other PRRs. A decreased ROS burst was observed in bald-silenced plants compared to control plants (FIG. 3C), indicating that FLS3 functions in a BAK1-dependent manner. Additionally, FLS3 co-immunoprecipitated with BAK1 whereas the YFP control could not pull down FLS3 (FIG. 3D), showing that FLS3 and BAK1 could physical associate in plant cells and indicating that FLS3 signaling occurs through a BAK1-dependent mechanism.

Figure 3E:
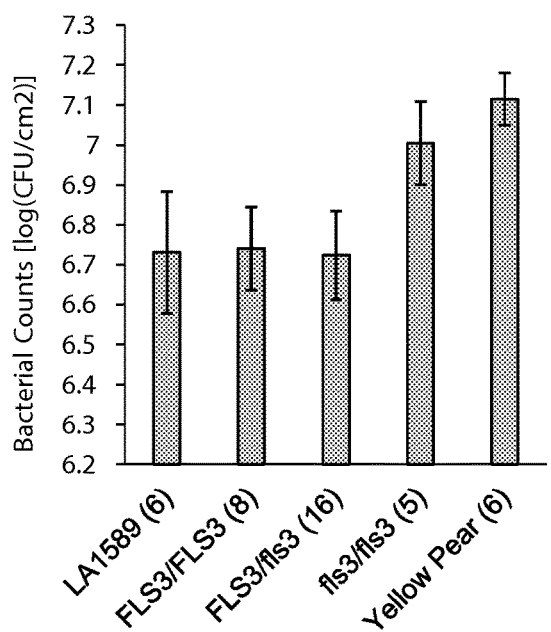

In order to confirm that FLS3 contributes to plant immunity, F2 plants from the LA1589×Yellow Pear cross were infected with a bacterial pathogen. Decreased bacterial growth was observed in LA1589 (FLS3/FLS3) and in F2 plants that have a functional copy of FLS3 (FLS3/FLS3 or FLS3/fls3) (FIG. 3E). Since the bacterial pathogen used in these experiments, Pcal ES4326, lacks a flg22 that can be detected by FLS2, it can be concluded that this increased resistance observed specifically in plants expressing FLS3 is due to the ability of these plants to perceive flagellin and mount an effective immune response against the pathogen.

Finally, using a novel photo-crosslinking and click chemistry approach (FIG. 4A), direct physical binding between FLS3 and flgII-28 was demonstrated. Plasma membrane preparations were generated from *N. benthamiana* leaves transiently expressing FLS3-GFP, and were incubated with either flgII-28* or flg22*, peptide MAMPs that have been decorated with an alkyne functional group and the trifluoromethyldiazirine photo-crosslinking moiety. These probes were generated for use in these particular experiments; however, these two chemical features have been used for other purposes elsewhere. Unmodified flgII-28 or flg22 peptides were added to some samples in order to demonstrate specificity of labeling. Samples were irradiated with UV light to stimulate photo-crosslinking of flgII-28* to FLS3 by way of the trifluoromethyldiazirine chemistry. Membrane proteins were immunoprecipitated on to GFP nanotrap resin, washed, and reacted with azide-biotin using click chemistry. This reaction resulted in the addition of biotin to the flgII-28* conjugated to FLS3-GFP. Proteins were released from the resin by boiling in Laemmli buffer and subjected to immunoblot analysis. Detection by anti-GFP antibodies demonstrated that FLS3-GFP protein was present in all immunoprecipitated samples. However, only FLS3 protein treated with flgII-28* demonstrated biotinylation when probed with Streptavidin-HRP (FIG. 4B). This biotinylation could be competed away with excess unmodified flgII-28, but not with excess flg22 (FIG. 4C). This result definitively demonstrated that FLS3 is the bona fide receptor for flgII-28.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A nucleic acid construct comprising:
a nucleic acid molecule that encodes a FLAGELLIN-SENSING 3 ("FLS3") protein, wherein said nucleic acid molecule encodes a polypeptide having the amino acid sequence of SEQ ID NO:2, SEQ ID NO:4, or SEQ ID NO: 5;
a 5' heterologous DNA promoter sequence; and
a 3' terminator sequence, wherein the nucleic acid molecule, the DNA promoter sequence, and the terminator sequence are operatively coupled to permit transcription of the nucleic acid molecule.

2. The nucleic acid construct according to claim 1, wherein the nucleic acid molecule comprises the nucleotide sequence of SEQ ID NO:1.

3. The nucleic acid construct according to claim 1, wherein the DNA promoter sequence is a constitutive, inducible, tissue-specific, or organ-specific plant promoter.

4. An expression vector comprising the nucleic acid construct according to claim 1.

5. A host cell transformed with the nucleic acid construct according to claim 1.

6. The host cell according to claim 5, wherein the host cell is a bacterial cell or a plant cell.

7. A plant transformed with the nucleic acid construct according to claim 1.

8. The plant according to claim 7, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca*, and *zinnia*.

9. A component part of the plant according to claim 7.

10. A fruit of the plant according to claim 7.

11. A plant seed produced from the plant according to claim 7.

12. A plant seed transformed with the nucleic acid construct according to claim 1.

13. A method of expressing a nucleic acid molecule in a plant, said method comprising:
providing a transgenic plant or transgenic plant cell transformed with a nucleic acid construct comprising:
a nucleic acid molecule that encodes a FLAGELLIN-SENSING 3 ("FLS3") protein, wherein said nucleic acid molecule encodes a polypeptide having the amino acid sequence of SEQ ID NO:2, SEQ ID NO:4, or SEQ ID NO: 5;
a 5' heterologous DNA promoter sequence; and
a 3' terminator sequence, wherein the nucleic acid molecule, the DNA promoter sequence, and the terminator sequence are operatively coupled to permit transcription of the nucleic acid molecule, and
growing the transgenic plant or a plant grown from the transgenic plant cell under conditions effective to express the nucleic acid molecule in said transgenic plant or said plant grown from the transgenic plant cell.

14. The method according to claim 13, wherein the nucleic acid molecule comprises the nucleotide sequence of SEQ ID NO:1.

15. The method according to claim 13, wherein the DNA promoter sequence is a constitutive, inducible, tissue-specific, or organ-specific plant promoter.

16. The method according to claim 13, wherein the transgenic plant is provided.

17. The method according to claim 13, wherein the transgenic plant cell is provided.

18. The method according to claim 13, wherein a transgenic plant seed comprising the transgenic plant cell is provided.

19. The method according to claim 13, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca*, and *zinnia*.

20. The method according to claim 13, wherein said providing comprises transforming a non-transgenic plant or a non-transgenic plant cell with the nucleic acid construct to yield said transgenic plant or transgenic plant cell.

21. The method according to claim 13, wherein the nucleic acid molecule comprises the nucleotide sequence of SEQ ID NO:3.

22. The method according to claim 13, wherein the nucleic acid molecule encodes a polypeptide having the amino acid sequence of SEQ ID NO:2.

23. The method according to claim 13, wherein the nucleic acid molecule encodes a polypeptide having the amino acid sequence of SEQ ID NO:4.

24. The method according to claim 13, wherein the nucleic acid molecule encodes a polypeptide having the amino acid sequence of SEQ ID NO:5.

25. The nucleic acid construct according to claim 1, wherein the nucleic acid molecule comprises the nucleotide sequence of SEQ ID NO:3.

26. The nucleic acid construct according to claim 1, wherein the nucleic acid molecule encodes a polypeptide having the amino acid sequence of SEQ ID NO:2.

27. The nucleic acid construct according to claim 1, wherein the nucleic acid molecule encodes a polypeptide having the amino acid sequence of SEQ ID NO:4.

28. The nucleic acid construct according to claim 1, wherein the nucleic acid molecule encodes a polypeptide having the amino acid sequence of SEQ ID NO:5.

* * * * *